United States Patent [19]

Cook et al.

[11] Patent Number: 5,543,507

[45] Date of Patent: Aug. 6, 1996

[54] COVALENTLY CROSS-LINKED OLIGONUCLEOTIDES

[75] Inventors: Phillip D. Cook; Muthiah Manoharan; Thomas Bruice, all of Carlsbad, Calif.

[73] Assignee: ISIS Pharmaceuticals, Inc., Carlsbad, Calif.

[21] Appl. No.: 205,507

[22] Filed: Mar. 2, 1994

Related U.S. Application Data

[63] Continuation-in-part of Ser. No. 846,376, filed as PCT/US93/02059, Mar. 5, 1992, abandoned.

[51] Int. Cl.$^6$ .................... C07H 21/00; C07H 21/02; C07H 21/04

[52] U.S. Cl. .............. 536/23.1; 536/24.1; 536/24.3; 536/24.31; 536/24.32; 536/24.33; 536/25.2; 536/25.3; 435/91.1; 435/91.4; 435/91.21; 435/91.5

[58] Field of Search .................. 514/44; 536/23.1, 536/24.1, 24.2, 24.3, 24.31, 24.32, 24.33, 25.3, 25.2; 435/90, 91.1, 91.4, 91.21, 91.5

[56] References Cited

U.S. PATENT DOCUMENTS

| | | | |
|---|---|---|---|
| 4,123,610 | 10/1978 | Summerton et al. | 536/25.3 |
| 4,868,103 | 9/1989 | Stavrianopoulos | 435/5 |
| 5,082,934 | 1/1992 | Saba et al. | 536/17.6 |
| 5,223,618 | 6/1993 | Cook et al. | 544/276 |
| 5,296,350 | 3/1994 | Rokita et al. | 435/6 |
| 5,367,066 | 11/1994 | Urdea et al. | 536/24.3 |
| 5,378,825 | 1/1995 | Cook et al. | 536/25.34 |

OTHER PUBLICATIONS

*Webster's II New Riverside University Dictionary*, 1984, Houghton Mifflin Co., Boston, MA, pp. 819 and 979.

Stryer, L., 1978, in: *Biochemistry*, W. H. Freeman and Company, San Francisco, CA pp. 528–529.

Grineva, N. I. and Karpova, G. G., "Complementarily Addressed Modification of rRNA with p–(Chloroethylamino) Benzylidene Hexanucleotides", *FEBS.*, 32, (1973), 351–355.

Sumerton and Bartlett [see: Summerton, J. and Bartlett, P. A.], "Sequence–specific Crosslinking Agents for Nucleic Acids", *J. Mol. Biol.* 122, (1978), 145–162.

Summerton, J., "Sequence–specific Crosslinking Agents for Nucleic Acids: Design and Functional Group Testing", *J. Theor. Biology*, 78, (1979), 61–75.

Meyer et al., "Efficient, Specific Cross–Linking and Cleavage of DNA by Stable, Synthetic Complementary Oligodeoxynucleotides, *J. Am. Chem. Soc.*, 111", (1989), 8517–8519.

Webb., T. R. and Matteucci, M. D., "Hybridization Triggered Cross–Linking of Deoxyoligonucleotides, Nucleic Acids", Res., 14, (1986), 7661–7674.

Matteucci et al., "Synthesis and Crosslinking Properties of a Deoxyoligonucleotide Containing $N_6$, $N_6$–Ethano–Deoxyadenosine", *Tetrahedron Ltrs.*, 28, (1987), 2469–2472.

Ferentz, A. E. and Verdine, G. L., "Disulfide Cross–Linked Oligonucleotides", *J. Am. Chem. Soc.*, 113, (1991), 4000–4002.

Lee, B. L. et al., "Interaction of Psoralen–Derivatized Oligodeoxyribonucleoside Methylphosphonates with Single–Stranded DNA", *Biochemistry*, 27, (1988), 3197–3203.

Manoharan et al., "Coexistence of Conformations in a DNA Heteroduplex Revealed by Site Specific Labeling with $_{13}$C–Labeled Nucleotides", *J. Am. Chem. Soc.*, 109, (1987), 7217–7219.

Manoharan, M. et al., "Mechanism of UV Endonuclease V Cleavage of Abasic Sites in DNA Determined by $_{13}$C Labeling", *J. Am. Chem. Soc.*, 110, (1988), 2690–2691.

Vasseur, J.–J. et al., "Apurnic DNA: Modelisation and Reactivity Towards 9–Aminoellipticine and Related Amines", *Nucleosides & Nucleotides*, 8, (1989), 863–866.

Bertrand et al., "Synthesis, Thermal Stability and Reactivity Towards 9–Aminoellipticine of Double–Stranded Oligonucleotides Containing a True Abasic Site", *Nucleic Acids Research*, 17, (1989), 10307–10319.

P. Iyer et al., "Abasic Oligodeoxyribonucleoside Phosphorothioates Synthesis and Evaluation as Anti–HIV–1 Agents", *Nucleic Acids Research*, 18, (1990), 2855–2859.

Groebke, K. and Leumann, C., "A Method for Preparing Oligodeoxynucleotides Containing an Apurinic Site", *Helvetica Chimica Acta*, 73, (1990), 608–617.

Peoc'h, D. et al., "Efficient Chemical Synthesis of Oligodeoxynucleotides Containing a True Abasic Site", *Tetrahedron Letters*, 32, (1991), 207–210.

"Nucleic Acids In Chemistry And Biology", Edited by G. Michael Blackburn and Michael J. Gait, Oxford University Press, New York, (1991), 52–58.

Pfitzner, K. E. and Moffat, J. G., "Sulfoxide–Carbodiimide Reactions. I. A Facile Oxidation of Alcohols", *J. Am. Chem. Soc.*, 87, (1965), 5661–5670.

Lemaitre et al., "Specific Antiviral Activity of a poly(L–l–ysine)–Conjugated Oligodeoxyribonucleotide Sequence Complementary to Vesicular Stromatitis Virus N Protein mRNA Initiation Site", *Proc. Natl. Acad. Sci. USA*, 84, (1987), 648–652.

Chang et al., "Periodate–Oxidized AMP as a Substrate, an Inhibitor and an Affinity Label of Human Placental Alkaline Phosphatase", *Biochem. J.*, 199, (1981), 281–287.

Easterbrook–Smith et al., "Pyruvate Carboxylase: Affinity Labelling of the Magnesium Adenosine Tri–phosphate Binding Site", *Eur. J. Biochem.*, 62, (1976), 125–130.

(List continued on next page.)

*Primary Examiner*—Christopher S. F. Low
*Attorney, Agent, or Firm*—Woodcock Washburn Kurtz Mackiewicz & Norris

[57] ABSTRACT

Covalent cross-linkages for two oligonucleotide strands or for first and second regions of a single oligonucleotide strand connect sugar moieties of nucleotides on the respective strands or the regions of the single strand. The cross-linkages are connected to at least one strand or region via a space-spanning group. The cross-linkage also can be connected to the other strand or other region via a space-spanning group or via an abasic site located on the other strand or other region.

77 Claims, No Drawings

OTHER PUBLICATIONS

Akiyama et al., "The Selective Protection of Uridine with a p-Methoxybenzyl Chloride: A Synthesis of 2'-O-Methyluridine", *Notes Bull. Chem. Soc. Jpn.*, 63, (1990), 3356–3357.

Sproat et al., "New Synthetic Routes to Protected Purine 2'-O-methylriboside-3'-O-phosphoramidites Using a Novel Alkylation Procedure", *Nucleic Acid Res.*, 18, (1990), 41–49.

Sproat, B. S. et al., "New Synthetic Routes to Synthons Suitable for 2'-O-allyloligoribonucleotide Assembly", *Nucleic Acids Research*, 19, (1991), 733–738.

McArthur, C. R. et al., "Amino Group Blocking. Improved Method for N-Phthaloylation Using N-(Ethoxycarbonyl) Phthalimide", *Synth. Commun.* 13, (1983), 311–318.

Divakar, K. J. et al., "Approaches to the Synthesis of 2'-Thio Analogues of Pyrimidine Ribosides", *J. Chem. Soc. Perkin Trans.* 1, (1990), 969–974.

Butke, G. et al., "Facile Synthesis of 2'-Amino-2'-Deoxyadenosine, J. Carbohydrates", *Nucleosides, Nucleotides*, 7, (1988), 63–75.

Fiandor, J. and Tam, S. Y., "Synthesis of 3'-Deoxy-3'-(2-Propynyl)Thymidine and 3'-Cyanomethyl-3'-Deoxythymidine, Analogs of AZT", *Tetrahedron Letters*, 31, (1990), 597–600.

Hall, R. H. and Fleysher, M. H., "Synthetic Procedures in Nucleic Acid Chemistry", W. W. Zorbach and R. S. Tipson, Editors, vol. 1, John Wiley & Sons, (1968).

Hansske, F. et al., "2' and 3'-Ketonucleosides and Their Arabino and Xylo Reduction Products", *Tetrahedron*, 40, (1984) 125–135.

Francois, P. et al., "Flexible Aglycone Residues in Duplex DNA", *Tetrahedron Letters*, 31, (1990), 6347–6350.

Lindahl, T. et al., "DNA N-Glycosidases: Properties of Uracil-DNA Glycosidase From *Escherichia Coli*", *J. Biol. Chem.*, 252, (1977), 3286–3294.

Horn, T. et al., "Controlled Chemical Cleavage of Synthetic DNA at Specific Sites", *Nucleosides & Nucleotides*, 10, (1991), 299–302.

Knorre et al., "Nucleotide and Oligonucleotide Derivates As Enzyme and Nucleic Acid Targeted Irreversible Inhibitors, Chemical Aspects", *G. Weber (Ed.), Advance Press, Oxford,* (1986), 277–299.

Ratner, "Can The Antisense Message Be Delivered", *Biotechnology*, 7, (1989), 207.

Stein, et al., "Antisense Oligonucleotides as Therapeutic Agents —Is the Bullet Really Magical?", *Science*, 261, (1993) 1004–1012.

Farahani, et al., "Hydroxyl Radical Induced Cross-Linking Between Phenylalanine and 2-Deoxyribose", *Biochemistry*, 27, No. 13 (1988) 4695–4698.

Cowart, et al., "A Novel Combined Chemical-Enzymatic Synthesis of Cross-Linked DNA Using a Nucleosside Triphosphate Analogue", *Biochemistry*, 30, No. 3, (1991), 788–796.

Manoharan, et al., "Introduction of a Lipophilic Thioether Tether in the Minor Groove of Nucleic Acids for Antisense Applications", *Biorganic & Medicinal Chemistry Letters*, 3, No. 12, (1993), 2765–2770.

Heaphy, et al., "HIV-1 Regulator of Virion Expression (Rev) Protein Binds to an RNA Stem–Loop Structure Located within the Rev Response Element Region", *Cell*, 60, (1990), 685–693.

Bartel, et al., "HIV-1 Rev Regulation Involves Recognition of Non–Watson–Crick Base Pairs in Viral RNA", *Cell*, 67, (1991), 529–536.

Hegde, et al., "Crystal Structure at 1..7 A of the Bovine Papillomavirus-1 E2 DNA–Binding Domain Bound to its DNA Target", *Nature*, 359, (1992), 505–512.

Dartmann, et al., "The Nucleotide Sequence and Genome Organization of Human Papilloma Virus Type 11", *Virology*, 151, (1986), 124–130.

Horne et al., 1990, *J. Am. Chem. Soc.* 112, 2435–2437.

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 1:

CGCAGUCAGC C          11

( 2 ) INFORMATION FOR SEQ ID NO: 2:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 2:

CGCAGDCAGC C          11

( 2 ) INFORMATION FOR SEQ ID NO: 3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 3:

GACAGAGGUA GGAGAAGUGA          20

( 2 ) INFORMATION FOR SEQ ID NO: 4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 4:

GACAGAGGDA GGAGAAGDGA          20

( 2 ) INFORMATION FOR SEQ ID NO: 5:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 5:

GGCTGACTGC G                                   11

( 2 ) INFORMATION FOR SEQ ID NO: 6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 6:

CTGTCTCCAT CCTCTTCACT                           20

( 2 ) INFORMATION FOR SEQ ID NO: 7:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 7:

GGCTGUCTGC G                                   11

( 2 ) INFORMATION FOR SEQ ID NO: 8:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 8:

AGCCAGAUCU GAGCCUGGGA GCUCUCUGGC U            31

( 2 ) INFORMATION FOR SEQ ID NO: 9:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 9:

GGCTGDCTGC G                                   11

( 2 ) INFORMATION FOR SEQ ID NO: 10:

( i ) SEQUENCE CHARACTERISTICS:
        ( A ) LENGTH: 10

(B) TYPE: nucleic acid
(C) STRANDEDNESS: single
(D) TOPOLOGY: linear (iv) ANTI-SENSE: no (xi) SEQUENCE DESCRIPTION: SEQ ID NO: 10:

CUCUCUGGUC    10

(2) INFORMATION FOR SEQ ID NO: 11:

(i) SEQUENCE CHARACTERISTICS:
(A) LENGTH: 13
(B) TYPE: nucleic acid
(C) STRANDEDNESS: single
(D) TOPOLOGY: linear (iv) ANTI-SENSE: no (xi) SEQUENCE DESCRIPTION: SEQ ID NO: 11:

GACCAGAUCU GAG    13

(2) INFORMATION FOR SEQ ID NO: 12:

(i) SEQUENCE CHARACTERISTICS:
(A) LENGTH: 33
(B) TYPE: nucleic acid
(C) STRANDEDNESS: single
(D) TOPOLOGY: linear (iv) ANTI-SENSE: no (xi) SEQUENCE DESCRIPTION: SEQ ID NO: 12:

UAGCCAGAUC UGAGCCUGGG AGCUCUCUGG CUA    33

(2) INFORMATION FOR SEQ ID NO: 13:

(i) SEQUENCE CHARACTERISTICS:
(A) LENGTH: 33
(B) TYPE: nucleic acid
(C) STRANDEDNESS: single
(D) TOPOLOGY: linear (iv) ANTI-SENSE: no (xi) SEQUENCE DESCRIPTION: SEQ ID NO: 13:

TAGCCAGATC TGAGCCTGGG AGCTCTCTGG CUA    33

(2) INFORMATION FOR SEQ ID NO: 14:

(i) SEQUENCE CHARACTERISTICS:
(A) LENGTH: 31
(B) TYPE: nucleic acid
(C) STRANDEDNESS: single
(D) TOPOLOGY: linear (iv) ANTI-SENSE: no (xi) SEQUENCE DESCRIPTION: SEQ ID NO: 14:

GACUAGAUCU GAGCCUGGGA GCUCUCUAGU C    31

(2) INFORMATION FOR SEQ ID NO: 15:

(i) SEQUENCE CHARACTERISTICS:
(A) LENGTH: 31
(B) TYPE: nucleic acid
(C) STRANDEDNESS: single
(D) TOPOLOGY: linear (iv) ANTI-SENSE: no (x i) SEQUENCE DESCRIPTION: SEQ ID NO: 15:

UACCAGAUCU GAGCCUGGGA GCUCUCUGGU A                                                             31

(2) INFORMATION FOR SEQ ID NO: 16:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: no (x i) SEQUENCE DESCRIPTION: SEQ ID NO: 16:

CCGAACCGAC GTCGGTUCGC                                                                          20

(2) INFORMATION FOR SEQ ID NO: 17:

(i) SEQUENCE CHARACTERISTICS:
        (A) LENGTH: 30
        (B) TYPE: nucleic acid
        (C) STRANDEDNESS: single
        (D) TOPOLOGY: linear (i v) ANTI-SENSE: no (x i) SEQUENCE DESCRIPTION: SEQ ID NO: 17:

GGUGGGCGCA GCUUCGGCUG ACGGUACACC                                                               30

COVALENTLY CROSS-LINKED OLIGONUCLEOTIDES

CROSS REFERENCE TO RELATED APPLICATIONS

This application is a continuation-in-part of PCT/US93/02059, filed Mar. 5, 1993, which is a continuation-in-part of U.S. Ser. No. 846,376, now U.S. Ser. No. 295,743, fled Aug. 30, 1994, filed Mar. 5, 1992, now abandoned. Each of these patent applications are assigned to the assignee of this application and are incorporated by reference herein.

FIELD OF THE INVENTION

This invention is directed to covalent cross-linkages for oligonucleotides. The cross-linkages connect either two oligonucleotide strands or different regions of a single oligonucleotide strand via a space-spanning group that extends from a sugar moiety on a nucleotide of the first strand or strand region to a nucleotide on the other strand or strand region.

BACKGROUND OF THE INVENTION

Several examples have been reported of cross-linking between complementary oligonucleotides. The purpose of such cross-linking often has been to disrupt the function of a nucleic acid, primarily by cleavage of the target. It is known to cross-link nucleic acids in a positionally uncontrolled manner with UV exposure. However, Grineva, and Karpova, *FEBS.*, 1973, 32, 351–355, appear to have been the first to covalently cross-link complementary strands of oligonucleotides at a specific site utilizing controlled chemistry. A nitrogen mustard was attached to the 3' terminal ribose unit of an oligonucleotide via an acetal linkage or to the 5' end of an oligonucleotide via a phosphoramide linkage. On hybridization, the reactive mustards covalently cross-linked to the complementary strand via alkylation of the ternary heteroaromatic nitrogen atom at the 7-position of guanine or adenine. However, the alkylated base thus formed is a quaternary charged species that is subject to rapid chemical degradation via imidazole ring opening followed by cleavage of the targeted strand.

Enzymes are known to remove alkylated bases from nucleic acids. Indeed, such enzymatic removal is implicated in DNA repair mechanisms. The destruction of a targeted alkylated nucleic acid theoretically could be utilized for antimicrobial or antitumor therapy. However, cross-linking alkylation reactions and subsequent degradations are not desirable where host cell viability is necessary.

Summerton and Bartlett have proposed another type of alkylated oligonucleotide wherein an α-bromomethylketone attached to the 4-position of a cytidine nucleotide spans the major groove and alkylates the 7-position of a complementary guanine residue in a targeted strand. [See, *J. Mol. Biol.*, 1978, 122, 145–162; *J. Theor. Biology*, 1979, 78, 61–75; and U.S. Pat. No. 4,123,610]. As with the nitrogen mustards noted above, this alkylation yields a charged species that effects cleavage of the targeted nucleic acid strand following alkylation.

A further example of a covalent cross-linkage to the 7-position nitrogen of guanine is described by Meyer et. al., *J. Am. Chem. Soc.*, 1989, 111, 8517. The authors attached an iodoacetamidopropyl moiety to the 5-position of a thymidine nucleotide of DNA. The iodoacetamidopropyl moiety subsequently alkylated the 7-position of a guanine nucleotide at a position two base pairs down the complementary strand. Cleavage of the targeted strand was observed at various times and temperatures.

Matteucci and Webb have described a hybridization triggered cross-linking process where an N6,N6-ethano-adenine or N4,N4-ethanocytosine alkylates an appropriately positioned nucleophile in a complementary strand. [See, *Nucleic Acids Res.*, 1986, 14, 7661; *Tetrahedron Letters*, 1987, 28, 2469–2472.] This process has been designed to inactivate the normal function of the targeted DNA either by forming a stable adduct or by hydrolytic or enzymatic cleavage.

A cross-linkage similar to the above-noted N6,N6-ethano linkage was described by Ferentz, et al., *J. Am. Chem. Soc.*, 1991, 113, 4000, who utilized either an ethyl disulfide or a propyl disulfide linkage to connect the N6-positions of adenine residues on a self-complementary oligonucleotide.

Lee, et al., *Biochemistry*, 1988, 27, 3197–3203, described the interaction of psoralen-derivatized methyl phosphonate oligonucleotides with single-stranded DNA. According to this method, irradiation effects cross-linking which, in turn, inactivates DNA. Psoralen cross-linkages occur only between pyrimidine bases to join single-stranded or, more commonly, double-stranded structures.

The generation of an abasic site on a nucleic acid has been implicated in the above-noted enzymatic removal of alkylated bases from nucleic acids. Manoharan, et al., *J. Am. Chem. Soc.*, 1987, 109, 7217 and Manoharan, et al., *J. Am. Chem. Soc.*, 1988, 110, 2690, have characterized abasic sites in oligonucleotides utilizing $^{13}$C NMR spectroscopy. Abasic sites also have been created on nucleic acids to attach the intercalator 9-aminoellipticine to nucleic acids. Vasseur, et al., *Nucleosides & Nucleotides*, 1989, 8, 863–866, reported that the trimer Tp(Ap)Pt, where (Ap) is an apurinic site yielded a mixture of products when reacted with the intercalator 9-aminoellipticine. The reaction produced a desired Schiff's base adduct between the apurinic site and the 9-aminoellipticine, but also resulted in cleavage of the phosphate backbone. This work was extended by Bertrand, et al., *Nucleic Acids Research*, 1989, 17, 10307, to the interaction of 9-aminoellipticine and a 13-mer oligonucleotide. The 13-mer oligonucleotide contained only a single purine nucleotide. Acid treatment resulted in loss of the purine base to yield an unstable abasic site. The 9-aminoellipticine was successfully linked to the abasic site in the oligonucleotide by reducing the Schiff's base adduct during the reaction. Using an oligonucleotide having a single purine site, the authors were able to study the coupling of the intercalator 9-aminoellipticine to the oligonucleotide. It is unlikely, however, that oligonucleotides which bind to sequences of biological significance contain only a single purinic site.

Other abasic site-containing oligonucleotides have been assembled by synthetically incorporating abasic nucleoside precursors into an oligonucleotide. For example, Philippe, et al., *Tetrahedron Letters*, 1990, 31, 6347–6350, incorporated a 2-deoxy-D-ribose having a primary amide function attached via a pentamethylene chain to its 1'-position. 1,2-Dideoxy-D-ribofuranose and butane 1,3-diol likewise have been incorporated into oligonucleotides. [See, P. Iyer, et al., *Nucleic Acids Research*, 1990, 18, 2855.]

Groehke, et al., *Helvetica Chimica Acta*, 1990, 73, 608, reported the preparation of a (tert-butyl)dimethylsilyl-protected deoxy-D-ribose and its incorporation into oligonucleotides utilizing solid state techniques. Reoc'h et al., *Tetrahedron Letters*, 1991, 32, 207, used 1-(o-nitrobenzyl)-2-deoxy-D-ribofuranose in the synthesis of other oligonucleotides. None of these chemically generated abasic sites have been utilized to effect cross-linking.

Application PCT/US91/01822, filed Mar. 19, 1991 and entitled Reagents And Methods For Modulating Gene Expression Through RNA Mimicry, discloses effective use of oligonucleotides that mimic RNA structure. The entire disclosure Application PCT/US91/01822, which is assigned to the assignee of this application, is herein incorporated by reference. The oligonucleotides disclosed in PCT/US91/01822 are selected to mimic a portion of an RNA encoded by a gene. The RNA-mimicking oligonucleotides interfere with or modulate gene expression by interfering with protein-RNA interactions.

In order to mimic an RNA, an oligonucleotide must assume and retain the RNA's secondary and tertiary structure. Although the physical and chemical forces that normally retain the RNA in its secondary and tertiary structure are non-covalent in nature, one way to fix an RNA mimic in the necessary secondary and tertiary structure would be to covalently cross-link the mimic. However, presently-known techniques for cross-linking nucleic acid strands either lead to strand cleavage, disruption of structure or Watson/Crick hydrogen bonding, or are only useful for limited, specific sequences or at specific locations in a sequence.

Cross-linkages between two oligonucleotide strands or between regions of a single strand would be undesirable where the cross-linkages could destroy the strands or strand or could unduly modify the conformational structure of the oligonucleotide. Cross-linkages also would be undesirable where they do not allow the cross-linked product to approximate the conformation of natural nucleic acids. Heretofore, there has be no suggestions in the art of cross-linkages or methods of cross-linking that do not destroy the strands, that allow suitable conformations, that are useful on various sequences and at various positions within the sequences, and that allow normal ranges of features such as the "tilt" and "propeller twist" features found in naturally occurring nucleic acid duplexes. Accordingly there remains a long-felt need for nucleic acid cross-linkages and methods of cross-linking nucleic acids.

OBJECTS OF THE INVENTION

It is a primary object of this invention to provide improved covalently cross-linked nucleic acids and methods of forming the same.

It is a further object of this invention to provide individual oligonucleotide strands that are covalently bonded to one another at one or more sites on the strands.

It is an even further object of this invention to provide a single oligonucleotide strand that is covalently bonded to itself at one or more sites on the strand.

It is an even further object of this invention to provide RNA mimics that are fixed in specific spatial conformations via cross-linking covalent bonds.

It is an additional object of this invention to provide covalently cross-linked oligonucleotides that have the same sequence as known nuclease-resistant mimics of binding receptors for nucleic acid-binding proteins.

These and other objects of this invention will become apparent to those skilled in the art from a review of this specification and the claims appended hereto.

BRIEF DESCRIPTION OF THE INVENTION

In accordance with this invention there are provided sequence-specific, covalently cross-linked nucleic acids comprising a first nucleotide located either on a first strand of complementary oligonucleotide strands or on a single oligonucleotide strand. The cross-linked nucleic acids further comprise a second nucleotide located on a further strand of the complementary strands or on the single strand at a site distal to the first nucleotide. A first bond means is located on a sugar moiety of the first nucleotide and a second bond means is located on a sugar moiety of the second nucleotide. A covalent cross-linkage connects the first and the second bond means and, in doing so, cross-links the strand or strands.

In one embodiment of the invention, the first and the second nucleotides are located within first and second nucleotide sequences, respectively, on a single oligonucleotide strand. In a first preferred embodiment, the second nucleotide sequence is separated from the first nucleotide sequence by a distance that allows the oligonucleotide strand to assume a conformation wherein the first and second nucleotide sequences are specifically hybridizable with one another. In a further preferred embodiment, the first and the second nucleotides are located in non-hybridizable positions but are in sufficient proximity to allow cross-linking between the first and second nucleotides.

In a preferred embodiment of the invention, the first bond means includes an abasic site and the second bond means includes a space-spanning-group that, in turn, includes an active functional group that is capable of covalently bonding with the abasic site.

Further in accordance with the invention there are provided sequence-specific, cross-linked oligonucleotides that include a first nucleotide located on a first complementary oligonucleotide strand, a second nucleotide located on a second complementary strand, a first bond precursor located on a sugar moiety of the first nucleotide, a second bond precursor located on a sugar moiety of the second nucleotide, and a covalent cross-linkage connecting the first and the second bond precursors to cross-link the first and the second strands. In a preferred embodiment of the invention, the first nucleotide is located in a first nucleotide sequence, the second nucleotide is located in a second nucleotide sequence, and the second nucleotide sequence is complementary to and specifically hybridizable with the first nucleotide sequence.

Additionally in accordance with this invention there are provided sequence-specific, cross-linked oligonucleotides that include a first nucleotide located on an oligonucleotide strand and a second nucleotide located on the same oligonucleotide strand. The first and second nucleotides are separated by a distance that allows the nucleotides to specifically hybridize with one another. A first bond precursor is located on a sugar moiety of the first nucleotide and a second bond precursor is located on a sugar moiety of the second nucleotide. A covalent cross-linkage connects the first and the second bond precursors, cross-linking the first and second nucleotides. In a preferred embodiment, the first nucleotide is located in a first nucleotide sequence, the second specific nucleotide is located in a second nucleotide sequence, and the second nucleotide sequence is complementary to and hybridizable with the first nucleotide sequence. In a further preferred embodiment, the first and second nucleotides are located in nonhybridizable positions but are in sufficient proximity that a cross-linkage can be formed between them.

Also in accordance with this invention there are provided cross-linked oligonucleotides comprising a first sequence region that includes an abasic site and a second sequence region that includes a space-spanning group. An active functional group is located on the space-spanning group and is covalently coupled with the abasic site. In a first preferred embodiment, the first sequence region and the second sequence region are on the same oligonucleotide strand. In a further preferred embodiment, the first sequence region and the second sequence region are on different oligonucleotide strands. In these preferred embodiments, the first sequence region and the second sequence region are complementary to and specifically hybridizable with one another. Preferably, the active functional group is an amine, hydrazine, hydroxylamine, semicarbazide, thiosemicarbazide, hydrazide, thiol or alcohol, and the abasic site includes an aldehydic functionality.

Space-spanning groups according to the invention comprise elongated chains from about 1 to about 50 atoms in length. Space-spanning groups preferably comprise elongated chains from about 4 to about 20 atoms in length, more preferably chains from about 8 to about 13 atoms in length.

Further in accordance with this invention there are provided cross-linked oligonucleotides that include a first sequence region, a second sequence region, and a covalently bonded linker of the structure:

$$X_1 - L_1 - Y - L_2 - X_2$$

wherein $X_1$ is covalently connected to the first sequence region and $X_2$ is covalently connected to the second sequence region and where:

(i) $X_1$ and $X_2$, independently, are O, S, NH, $CH_2$ or CO;

$L_1$ and $L_2$, independently, are $C_1$–$C_{20}$ straight chain alkyl, $C_1$–$C_{20}$ straight chain substituted alkyl, $C_2$–$C_{50}$ branched chain alkyl, $C_2$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne: $C_3$–$C_{50}$ branched chain alkyne, $C_3$–$C_{50}$ branched chain substituted alkyne, polyamine, polyamide, polyester, polyethylene glycol, polyether, aryl, aralkyl or heterocyclic; and Y is an imine, amine, oxime, hydroxylamine, hydrazine, hydrazone, azine, hydrazide-hydrazone, amide, hydrazide, semicarbazide, semicarbazone, thiosemicarbazide, thiocarbazone, disulfide, hemiacetal, thiohemiacetal, α-keto-alkylthioalkyl or α-keto-alkylaminoalkyl; or (ii) $X_1$ and $X_2$, independently, are O or NH; and $L_1$—Y—$L_2$ together are NH—LB—NH or NH—NH—LB—NH—NH; and $L_3$ is $C_1$–$C_{20}$ straight chain alkyl, $C_1$–$C_{20}$ straight chain substituted alkyl, $C_2$–$C_{50}$ branched chain alkyl, $C_2$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne, $C_3$–$C_{50}$ branched chain alkyne, $C_3$–$C_{50}$ branched chain substituted alkyne, polyamine, polyamide, polyester, polyethylene glycol, polyether, aryl, aralkyl or heterocyclic; or (iii) $X_1$ and $X_2$, independently, are O, S, NH, $CH_2$ or CO;

$L_1$ and $L_2$, independently, are $C_1$–$C_{20}$ straight chain alkylamino, $C_1$–$C_{20}$ straight chain substituted alkylamino, $C_2$–$C_{50}$ branched chain alkylamino, $C_2$–$C_{50}$ branched chain substituted alkylamino, $C_2$–$C_{20}$ straight chain alkenylamino, $C_2$–$C_{20}$ straight chain substituted alkenylamino, $C_3$–$C_{50}$ branched chain alkenylamino, $C_3$–$C_{50}$ branched chain substituted alkenylamino, $C_2$–$C_{20}$ straight chain alkynylamino, $C_2$–$C_{20}$ straight chain substituted alkynylamino, $C_3$–$C_{50}$ branched chain alkynylamino, $C_3$–$C_{50}$ branched chain substituted alkynylamino, $C_1$–$C_{20}$ straight chain alkylthio, $C_1$–$C_{20}$ straight chain substituted alkylthio, $C_2$–$C_{50}$ branched chain alkylthio, $C_2$–$C_{50}$ branched chain substituted alkylthio, $C_2$–$C_{20}$ straight chain alkenylthio, $C_2$–$C_{20}$ straight chain substituted alkenylthio, $C_3$–$C_{50}$ branched chain alkenylthio, $C_3$–$C_{50}$ branched chain substituted alkenylthio, $C_2$–$C_{20}$ straight chain alkynylthio, $C_2$–$C_{20}$ straight chain substituted alkynylthio, $C_3$–$C_{50}$ branched chain alkynylthio or $C_3$–$C_{50}$ branched chain substituted alkynylthio; and Y is a heterobifunctional or homobifunctional cross-linking reagent;

where said substituent of said substituted alkyl, substituted alkenyl and substituted alkyne moieties is an intercalator, a conjugate, polyamine, polyamide, polyethylene glycol, a group that enhances the pharmacodynamic properties of oligonucleotides or a group that enhances the pharmacokinetic properties of oligonucleotides.

Further in accordance with this invention there are provided cross-linked oligonucleotides that individually include a first sequence region, a second sequence region, a first space-spanning group connected to a 2'-position of a nucleotide located in the first sequence region, a second space-spanning group connected to a 2'-position of a nucleotide in the second sequence region, and a linking moiety covalently connecting the first and second space-spanning groups. In preferred embodiments the linking moiety is:

—N=CH—, —N(R)—, —N(R)—CH₂—N (R)—, —O—N=CH—, —O—N(R)—, —N(R)—N(R)—, —N(R)—N=CH—, —HC=N—N=CH—, —C(O)—N(R)—N=CH—, —C(O)N(R)—, —C(O)—N(R)—N(R)—, —N(R)—C(O)—N(R)—N(R)—, —N(R)—C(O)—N(R)—N (R)=CH—, —N(R)—C(S)—N(R)—N(R)—, —N(R)—C(S)—N(R)—N(R)=CH—, —CH(OH)—O—CH₂—, —CH(OH)—S—CH₂—, —CH₂—S—CH₂—C(O)—CH₂—, —CH₂—NH—CH₂—C(O)—CH₂— or —S—S—;

wherein R is H, alkyl, alkenyl, aralkyl, an intercalator, a conjugate, polyamine, polyamide, polyethylene glycol, a group that enhances the pharmacodynamic properties of oligonucleotides or a group that enhances the pharmacokinetic properties of oligonucleotides.

Further in accordance with this invention there are provided methods for fixing a sequence-specific oligonucleotide in a set configuration. Such methods include selecting a first site in the oligonucleotide, said first site having a first nucleotide sequence. The methods further include selecting a second site in the oligonucleotide, said second site having a second nucleotide sequence. A first bond precursor is attached to a sugar moiety of a first nucleotide of the first site, while a second bond precursor is attached to a sugar moiety of a second nucleotide of the second site. A covalent cross-linkage is formed between the first and the second bond precursors. In a preferred embodiment, the first bond precursor is attached to the first site by reacting a first nucleotide precursor with a reagent for introducing the first bond precursor on a sugar moiety of the first nucleotide precursor. The first nucleotide precursor is derivatized to a protected and activated form and is synthetically incorporated into the first specific nucleotide sequence. The second nucleotide sequence can be complementary to and hybridizable with the first nucleotide sequence.

In one embodiment of this method, the first bond precursor is an abasic nucleotide and the second bond precursor is attached to a 2'-position of the second nucleotide. In this embodiment, the second bond precursor is reacted with the abasic site to form an imine, oxime, hydrazone, hydrazide-hydrozone, semicarbazone, thiosemicarbazone, hemiacetal or thiohemiacetal linkage between the first nucleotide sequence and the second nucleotide sequence. Certain of these linkages can be reduced to amine, hydroxylamine, hydrazine, hydrazide, semicarbazide or thiosemicarbazide linkages.

In a further embodiment of the method, the first bond precursor is attached to a 2'-position of the first nucleotide and the second bond precursor is attached to a 2'-position of the second nucleotide. Preferred linkages for this embodiment include:

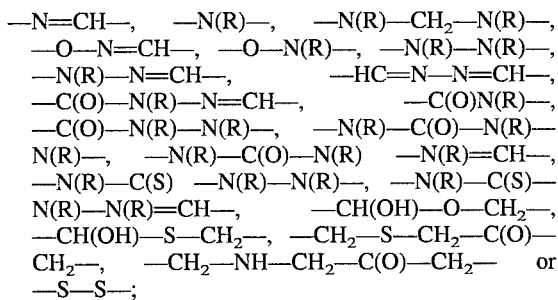

wherein R is H, alkyl, alkenyl, aralkyl, an intercalator, a conjugate, polyamine, polyamide, polyethylene glycol, a group that enhances the pharmacodynamic properties of oligonucleotides or a group that enhances the pharmacokinetic properties of oligonucleotides.

Further in accordance with this invention there are provided methods for cross-linking a single sequence-specific oligonucleotide strand. These methods include selecting first and second nucleotide sequences in the oligonucleotide, incorporating an abasic nucleotide within the first nucleotide sequence, attaching a bond precursor to one of the nucleotides of the second sequence, and forming a covalent cross-linkage between the abasic site and the bond precursor. In one embodiment of this method, the bond precursor is attached to a sugar moiety of the nucleotide of the second sequence, preferably at the 2'-position. In preferred embodiments, the abasic site includes an aldehydic functional group and the bond precursor includes a functional group capable of forming an oxime, imine, hydrazone, hydrazide-hydrazone, semicarbazone, thiosemicarbazone, hemiacetal or thiohemiacetal linkage with the aldehydic functional group. The second nucleotide sequence preferably is selected to be complementary to and specifically hybridizable with the first nucleotide sequence.

Further methods for cross-linking a single, sequence-specific oligonucleotide include selecting a first nucleotide sequence and a second nucleotide sequence in the oligonucleotide. A first bond precursor is attached to a sugar moiety of a nucleotide of the first nucleotide sequence and a second bond precursor is attached to a sugar moiety of a nucleotide of the second nucleotide sequence. A covalent cross-linkage is formed between the first and the second precursors. In preferred embodiments, the cross-linkage is an imine, amine, amino-alkylamine, oxime, hydroxylamine, hydrazine, hydrazone, azine, hydrazide-hydrazone, amide, hydrazide, semicarbazide, semicarbazone, thiosemicarbazide, thiocarbazone, disulfide, hemiacetal, thiohemiacetal, α-keto-alkylthioalkyl or α-keto-alkylaminoalkyl cross-linkage. In other preferred embodiments the second nucleotide sequence is complementary to and hybridizable with the first nucleotide sequence.

Further in accordance with this invention there are provided methods for cross-linking first and second strands of oligonucleotides, comprising the steps of selecting a first nucleotide sequence in a first oligonucleotide strand and selecting a second nucleotide sequence in a second oligonucleotide strand. The methods further include incorporating an abasic nucleotide within the first nucleotide sequence, attaching a bond precursor to a nucleotide of the second sequence, and forming a covalent cross-linkage between the abasic site and the bond precursor. In preferred embodiments, the second nucleotide sequence is complementary to and hybridizable with the first nucleotide sequence.

Further, in accordance with this invention there are provided methods for cross-linking first and second strands of oligonucleotides comprising the steps of selecting a first nucleotide sequence in a first oligonucleotide strand, selecting a second nucleotide sequence in a second oligonucleotide strand, attaching a first bond precursor to a sugar moiety of a nucleotide of the first sequence, locating a second covalent precursor on a sugar moiety of a nucleotide of the second sequence, and forming a covalent cross-linkage between the first and the second bond precursors. In preferred embodiments, the second nucleotide sequence is complementary to and hybridizable with the first nucleotide sequence.

DETAILED DESCRIPTION OF THE INVENTION

In accordance with the objects of this invention novel, covalently cross-linked oligonucleotide strands are disclosed. Preferably such strands are "duplexed" or "complementary" along at least a portion of their length. In the context of this invention the terminology "duplex strands" or "complementary strands" or like terminology refers in a first instance to two separate strands wherein at least one nucleotide or nucleotide sequence on one of the strands is complementary to and specifically hybridizable with an opposing nucleotide or nucleotide sequence on the other strand. In a second instance, this terminology refers to two sections or sequence regions of a single strand that are spaced from one another by a distance sufficient for the strand to fold onto itself and permit hybridization of complementary nucleotides in the respective sequence regions. Folded, self-hybridizing, single strands form hairpin loop, stem loop, interior loop or bulge type structures as a result of such hybridization.

Further in the context of this invention, the term "oligonucleotide" refers to polynucleotides formed from a plurality of joined nucleotide units. In certain instances, the nucleotides are formed from naturally occurring bases and pentofuranosyl sugars groups and are joined together via native inter-nucleoside phosphodiester linkages. The term "oligonucleotide" thus effectively includes naturally occurring or synthetic species formed from naturally occurring subunits. The term "oligonucleotide" also includes structures formed from modified or non-naturally occurring nucleotide subunits. Modifications can occur on the base portion of a nucleotide, on a sugar portion of a nucleotide or on the linkage joining one nucleotide to the next. In addition, modifications can be made wherein nucleoside units are joined together with connecting groups that substitute for the inter-nucleoside phosphate linkages. Inter-nucleoside connecting groups, which are to be distinguished from the cross-linkages of the invention, include —O—CH$_2$—CH$_2$—O— linkages and other novel linkages disclosed in U.S. Pat. No. 5,223,618, issued Jun. 29, 1993, and U.S. Pat. No. 5,378,825, issued Jan. 3, 1995, both assigned to the assignee of this invention. Other modifications can be made to the sugar, to the base, or to the phosphate group of the nucleotide. Exemplary modifications are disclosed in the following U.S. patent applications: Ser. No. 463,358, filed Jan. 11, 1990, entitled Compositions And Methods For Detecting And Modulating RNA Activity, now abandoned; Ser. No. 566,977, filed Aug. 13, 1990, entitled Sugar Modified Oligonucleotides That Detect And Modulate Gene Expression, now abandoned; U.S. Pat. No. 5,138,045, issued Aug. 11, 1992, Ser. No. 400,541, filed Mar. 8, 1995, entitled Nuclease Resistant Pyrimidine Modified Oligonucleotides That Detect And Modulate Gene Expression and serial number PCT/US91/00243, filed Jan. 11, 1991, published Jul. 25, 1991, as WO 91/10671 and entitled Compositions and Methods For Detecting And Modulating RNA Activity, all assigned to the assignee of this invention. The disclosures of all of the above-noted patent applications are herein incorporated by reference.

The term oligonucleotides, as used in connection with this invention, refers to structures including modified portions such as modified sugar moieties, modified base moieties or modified sugar linking moieties. These modified portions function in a manner similar to natural bases, natural sugars and natural phosphodiester linkages. Thus, in the context of this invention, oligonucleotides may have altered base moieties, altered sugar moieties or altered inter-sugar linkages. Exemplary among these are: phosphorothioate, phosphorodithioate, methyl phosphonate, phosphotriester or phosphoramidate inter-nucleoside linkages used in place of phosphodiester inter-nucleoside linkages; deaza or aza purines and pyrimidines used in place of natural purine and pyrimidine bases; pyrimidine bases having substituent groups at the 5- or 6-positions; purine bases having altered or replacement substituent groups at the 2-, 6- or 8- positions; or sugars having substituent groups at their 2'-position, substitutions for one or more of the hydrogen atoms of the sugar, or carbocyclic or acyclic sugars. Oligonucleotides may also comprise other modifications consistent with the spirit of this invention. Such oligonucleotides are best described as being functionally interchangeable with yet structurally distinct from natural oligonucleotides. All such oligonucleotides are comprehended by this invention so long as they effectively mimic the function of a desired RNA or DNA strand.

Further in the context of this invention, it will be recognized that the terms "cross-linkage," "cross-link" or "cross-linking" specifically exclude those portions of the oligonucleotide structure that linearly connect individual nucleoside subunits or nucleoside-like, modified subunits, i.e., those portions that connect the nucleoside units in the sequence that defines the primary structure of the oligonucleotide. Thus, "cross-linkage," "cross-link" or "cross-linking" exclude native phosphodiester linkages that connect nucleosides, as well as analogous, non-native internucleoside linkages such as phosphorothioate, phosphorodithioate methyl phosphonate, phosphotriester, phosphoramidate, and —O—CH$_2$CH$_2$—O— linkages used in place of phosphodiester inter-nucleoside linkages. The terms "cross-linkage," "cross-link" or "cross-linking" as used in the context of this invention refer to "additional" linkages created across a single oligonucleotide strand or several oligonucleotide strands to hold the strand or strands in secondary or other, higher-ordered structures. Primary, secondary, and higher-order structures are as defined in standard reference texts such as *Nucleic Acids In Chemistry And Biology*, edited by G. Michael Blackburn and Michael J. Gait, Oxford University Press, New York, 1991.

Cross-linking is employed in accordance with the present invention to fix separate oligonucleotide strands in duplex structures or to fix a single oligonucleotide strand in a hairpin loop, stem loop, interior loop, bulge or other similar higher-order structure. Such fixation is believed to confer nuclease resistance to oligonucleotides and to optimize structure-dependent function. Fixing a strand or strands in a duplex structure also can disrupt the normal function of single-strand nucleic acid-binding proteins by forming nuclease-resistant mimics of the proteins' binding receptors. Fixing a strand or strands in set secondary structures also makes it possible to mimic the RNA secondary structures found in diseased cells, particularly cells infected with viruses and retroviruses. A detailed delineation of such RNA mimicry is disclosed in Application PCT/US91/01822, filed Mar. 19, 1991, entitled Reagents and Methods For Modulating Gene Expression Through RNA Mimicry, assigned to the same assignee as this application. The entire contents of Application PCT/US91/01822 is herein incorporated by reference.

The "fixing" of multiple oligonucleotide strands or a single oligonucleotide strand in defined secondary or other higher-order structure is achieved in accordance with this invention by cross-linking the oligonucleotide strands or oligonucleotide. In one preferred embodiment, novel cross-linkages connect a nucleotide or nucleoside pentofuranosyl moiety on one strand with a nucleotide or nucleoside pentofuranosyl moiety on another strand. In another preferred embodiment, novel cross-linkages connect a nucleotide or nucleoside pentofuranosyl moiety on a first region of a single strand with a nucleotide or nucleoside pentofuranosyl moiety on a further region of the same strand. It is believed that such "sugar to sugar" cross-linkages were heretofore unknown. In a further embodiment of the invention, novel cross-linkages connect an abasic site on one oligonucleotide strand to a further site on another strand. Also, novel cross-linkages can connect an abasic site on a first region of a single strand with another site on another region of the single strand. It is believed that use of an abasic site as the attachment site for a oligonucleotide cross-linkage was also heretofore unknown.

In a further embodiment of the invention, novel cross-linkages of the invention connect a terminal sugar on one oligonucleotide strand or a first region of a single strand with a further site on a further strand or to a further region of a single strand.

One preferred cross-linkage of the invention connects the 2'-position of a ribose sugar on one oligonucleotide strand (or a first region of a single strand) to the 2'-position of a ribose sugar on another strand (or a further region of a single strand). This cross-linkage can be considered a 2'-ribose to 2'-ribose cross-linkage. A second preferred cross-linkage connects a 2'-ribose position on one oligonucleotide strand (or a first region of a single strand) to a C1'-ribose position (an abasic site) on another strand (or a further region of a single strand). This linkage can be considered a 2'-ribose to C1'-ribose cross-linkage. A third preferred cross-linkage connects a 2'-ribose position on one strand (or a first region of a single strand) to a seco-ribose on the 3'-terminal end of another strand (or a further region of a single strand). This linkage can be considered a 2'-ribose to seco-ribose linkage. A fourth preferred cross-linkage connects a 2'-ribose position on one strand (or a first region of a single strand) to 2' and 3' hydroxyls of a nucleoside sugar on the 3'-terminal end of another strand (or a further region of a single strand). This linkage can be considered a 2'-ribose to 2',3'-OH-ribose linkage.

For 2'-ribose to 2'-ribose cross-linkages, presently preferred are: cross-linkages between the 2'-hydroxyl groups (or other 2' substituent groups) of the nucleotide sugar moieties of a Watson/Crick nucleotide base pair; a cross-linkage between a 2'-hydroxyl group (or other 2' substituent group) of a nucleotide sugar moiety and a 2'-hydroxyl (or other 2' substituent group) of a nucleotide sugar moiety one base removed (in the 5'-direction) of the opposite strand; a cross-linkage between nucleotides one helical loop removed; or cross-linkage between nucleotides that are separated from each other along the strand or strands but that are located proximal or adjacent to each other in the higher-ordered structure. Molecular models and computer modeling indicate that the 2'hydroxyls of RNA-RNA duplexes are exposed in the minor groove or minor side. Thus, direct covalent cross-linkage of the 2'-hydroxyls with a linker of appropriate length should not disturb the natural conformation of the duplexes.

As per the teachings of this invention, RNA-RNA, DNA-DNA or DNA-RNA type duplexes can be covalently cross-linked via a space-spanning group attached to nucleotide units at desired attachment sites. The length of the space-spanning group on each strand or region of a single strand can be between 1 to about 25 atoms. Thus, when two space-spanning groups are cross-linked together, the total length of the space-spanning groups, the cross-linker, and any other connecting atoms should be less than about 50 atoms in length.

The space-spanning groups are composed of carbon atoms or of carbon atoms plus one or more heteroatoms such as nitrogen, sulfur or oxygen. It is preferred that the space-spanning group on an individual strand or on a sequence region of a single strand be about 20 atoms or less in length. More preferably, the cross-linking group is from 8 to 13 atoms in length.

For 2'-ribose to C1'-ribose cross-linkages, a cross-linkage is formed between a 2'-position of a nucleotide sugar moiety on one strand (or on a first region of a single strand) and an abasic 1'-site on another strand (or on a further region of a single strand). The cross-linking group preferably is from 8 to 13 atoms in length.

For 2'-ribose to seco-ribose cross-linkages, a cross-linkage is formed between a 3'-terminal ribofuranosyl nucleoside of a first strand and a reactive functionality on a space-spanning group attached to the sugar moiety of a nucleotide on another strand (or on a further region of the first strand). Preferably, such cross-linkage is made through 2' and 3' hydroxyl groups of the 3'-terminal nucleoside. The 2' and 3' hydroxyl groups are first converted to a 2',3'-dialdehyde structure with periodate. A cross-linkage is formed upon hybridization with a complementary strand that has a connecting or space-spanning group bearing a functional group capable of reacting with the aldehydic functionality. If a 2'-aminoalkoxy connecting or space-spanning group is provided on the 2'-ribose strand, reaction of the aldehydic functionality of the seco-ribose strand should form a Schiff's base. Reduction of this Schiff's base with sodium cyanoborohydride affords a stable cross-linkage.

For 2'-ribose to 2',3'-OH-ribose cross-linkages, a cross-linkage is formed between 2' and 3' hydroxyls of a 3'-terminal ribofuranosyl nucleoside of a first strand and an aldehyde functionality on a space-spanning group attached to a nucleotide sugar moiety on another strand (or on a further region of the first strand). On hybridization of the strands (or strand), the aldehyde functionality on the space-spanning group reacts with the 2',3'-hydroxyls to form an acetal linkage.

Oligonucleotides in accordance with this invention preferably comprise from about 3 to about 100 subunits. It is preferred that such oligonucleotides comprise greater than about 6 subunits, more preferably from about 8 to about 60 subunits. Oligonucleotides having from about 10 to about 30 subunits are still more preferred. It will be recognized that a subunit comprises a base moiety linked to a sugar moiety. A subunit typically is bound to adjacent subunits through internucleoside bonds.

As indicated in the above-referenced United States patent applications, oligonucleotides have diagnostic, therapeutic, and prophylactic applications and also can be used as research reagents. For therapeutic use, cross-linked oligonucleotide analogs can be administered to animals, including humans, suffering from a disease state that it is desirous to treat.

It is generally preferred to apply a therapeutic agent of the invention internally such as orally, intravenously or intramuscularly with or without pharmacologically acceptable carriers. Other forms of administration, such as transdermal, topical or intralesional administration, may also be useful. Cross-linked oligonucleotides also can be included in suppositories.

The crosslinked oligonucleotides of the invention can be used to identify the presence of certain protein. These proteins include, among others, envelope proteins and transcription factors. Identification of the proteins via interactions with the crosslinked oligonucleotides of the invention thus can be used as an identification of the source of those proteins, e.g. virus. Thus the crosslinked oligonucleotides of the invention are used for diagnostic reagents for the identification of viral agents and other targets of interest.

One such virus that can be identified via its proteins is the HIV virus. Identification of HIV proteins thus serves to identify the presence of the HIV virus in the sample. HIV has two regulatory proteins that are involved in the early phases of transcription. One of these is tat, the other is rev. Tat binds to TAR RNA. Rev is dependent on a particular RNA identified as the rev response element (RRE) (see Heaphy, et. al., *Cell*, 1990, 60:685–693). Since the rev element is long, a functional rev binding RNA variant, analogous to RRE but much shorter in length, was selected (via a combinatorial technique) and assayed against rev (see Barrel, et. al., *Cell*, 1991, 67:529–536). This analogue is identified as RBE3. A crosslinked species of the RBE3 RRE variant can be used to identify the presence of rev protein in a biological sample. The presence of rev thus indicates the presence of HIV.

In a like manner tat can be identified. A crosslinked oligonucleotide of the invention having the TAR sequence is used to identify the tat protein. A tat-TAR conjugate having an appropriate reporter group thereon, e.g. biotin, fluorescein or digoxigenin, is isolated and identified via the properties of the reporter group. This same technique is general in nature and can be used for the isolation and identification of other proteins. Sensitivity of the assay can be increased by using substitution on the oligonucleotides of the invention that improve the binding of the oligonucleotide to the protein. One such group is the 2'-fluoro group.

In addition to the above envelope proteins, the crosslinked oligonucleotide of the invention can be constructed to target transcription factors including, but not limited to, E2 protein of HPV, NFkβ, p53, and fos/jun.

In certain embodiments, a space-spanning group bearing an active functional group is located on one strand of a pair of duplexed oligonucleotide strands. Preferably, the space-spanning group is attached to a 2'-position of a nucleotide on the strand. The functional group is positioned on the space-spanning group at a point distal from the point at which the space-spanning group connects to the nucleotide. The space-spanning group is connected to the 2'-position via one or more connecting atoms. Preferably, the connecting atoms includes O, S, NH, $CH_2$ or CO.

The space-spanning group is preferably a linear or straight chain group. In one embodiment of the invention, the space-spanning group comprises a methylene chain from 1 to about 20 carbon atoms in length. Where the connecting atoms are methylene groups, the connecting group and the space-spanning group together form an alkyl chain. In other embodiments, one or more unsaturated sites are located in the space-spanning group, resulting in alkenyl or alkynyl chains. In these embodiments the alkenyl or alkynyl space-spanning groups have from 2 to about 20 carbon atoms.

In other embodiments the space-spanning group further includes branched chains and substituent groups that extend from a backbone or primary straight chain. Branched chains can be selected from branched alkyl, branched alkenyl or branched alkyne space-spanning groups. The branched chains, in addition to the carbon atoms of the main chain, have from 1 to about 30 carbon atoms. Further substituent atoms or substituent groups can also extend from the backbone or from any branched chains. Thus, the space-spanning group can include $C_1$–$C_{20}$ straight chain alkyl, $C_1$–$C_{20}$ straight chain substituted alkyl, $C_2$–$C_{50}$ branched chain alkyl, $C_2$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne, $C_3$–$C_{50}$ branched chain alkyne and $C_3$–$C_{50}$ branched chain substituted alkyne groups. Other space-spanning groups include aryl, aralkyl and heterocyclic groups.

Representative examples of the space-spanning groups include but are not limited to methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl straight chained alkyl groups; 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl branched or substituted groups; allyl, crotyl, propargyl, 2-pentenyl unsaturated groups; 4-methylenebenzyl, 1,4-naphthyl, 2,7-anthracyl and 2,6-phenanthryl aryl or aralkyl groups.

Other space-spanning groups include polyamine, polyamide, polyester, polyethylene glycol and polyether, (polyalkoxyalkyl) groups. Polyamines include compounds of the structure [amine functionality-(linker)$_m$]$_n$. Normally the linker is a methylene chain. The amine functionalities can be primary amines, hydrazines, semicarbazides, thiosemicarbazides or similar nitrogenous species. The number of individual units of the polyamine (n) is selected in conjunction with the number of linker atoms (m) such that the total number of atoms is preferably 20 or less. Thus, if [—$HN(CH_2)_m$—]$_n$ is selected as the polyamine backbone, n could be from 1 to 10 depending on m. For example, if m is 1, n can range up to 10, and if m is 2, n can range up to 5. If larger nitrogenous species such as hydrazine or semicarbazide are utilized, n and m would be correspondingly smaller to reflect the increased number of atoms contributed by the nitrogenous species.

Polyamides, polyesters and polyethylene glycols according to the invention have structures analogous to the above-described polyamines, except that an amide, ester or alcohol functionality is substituted for the nitrogenous species of the polyamine. Polyether groups also have analogous structures, except that one or more ether oxygen atoms are interspersed in the carbon chains.

Aryl, aralkyl and heterocyclic space-spanning groups are similar to the above-described alkyl, alkenyl and alkynyl groups, except that appropriate aromatic, mixed alkyl-aromatic or heterocyclic groups are selected. Such space-spanning groups preferably are less than about 20 atoms in length, excluding atoms that are not directly in the space-spanning group chain but are within the structure of the aromatic or heterocyclic ring. Aryl, aralkyl, and heterocyclic space-spanning groups can include up to about 50 atoms.

Substituent groups can be present on the above-described alkyl, alkenyl, alkyne, polyamine, polyamide, polyester, polyethylene glycol, polyether, aryl, aralkyl and heterocyclic space-spanning groups. Substituent groups include but are not limited to halogen, hydroxyl, keto, carboxy, nitrates, nitrites, nitro, nitroso, nitrile, trifluoromethyl, O-alkyl, S-alkyl, NH-alkyl, amino, azido, sulfoxide, sulfone, sulfide, silyl, intercalators, conjugates, polyamines, polyamides, polyethylene glycols, polyethers, groups that enhance the pharmacodynamic properties of oligonucleotides and groups that enhance the pharmacokinetic properties of oligonucleotides. Typical intercalators and conjugates include cholesterols, phospholipids, biotin, phenanthroline, phenazine, phenanthridine, anthraquinone, acridine, fluoresceins, rhodamines, coumarins, and dyes. Halogens include fluorine, chlorine, bromine and iodine. Groups that enhance pharmacodynamic properties, in the context of this invention, include groups that improve oligonucleotide uptake, enhance oligonucleotide resistance to degradation, and/or strengthen sequence-specific hybridization with RNA. Groups that enhance pharmacokinetic properties, in the context of this invention, include groups that improve oligonucleotide uptake, distribution, metabolism or excretion.

Nucleotides incorporating a connecting atom, a space-spanning group and a functional group on the end of the space-spanning group are generally synthesized as per the methods and syntheses disclosed in U.S. patent application Ser. Nos. 463,358, 566,977 and PCT/US91/00243. To introduce amine-functionalized space-spanning groups on a nucleotide within desired oligonucleotide sequences, 5'-dimethoxytrityl-2'-O, 2'-S or 2'-NH-(space-spanning group-N-phthalimido) nucleoside phosphoramidites are synthesized. The N-phthalimido amine protecting group is removed with concentrated $NH_4OH$. N-phthalimido compounds thus provide an amine-functionalized space-spanning group attached to the 2'-position of nucleotide components of an oligonucleotide.

The following compounds for forming compounds having amine-functionalized space-spanning groups are commercially available from Aldrich Chemical Co., Inc., Milwaukee, Wis.: N-(2-bromoethyl)phthalimide, N-(3-bromopropyl)phthalimide and N-(4-bromobutyl)phthalimide. Other phthalimide-protected amine compounds can be conveniently synthesized from appropriate alkyl, aralkyl or aryl halides and phthalimide. Representative compounds include N-(7-bromoheptyl)phthalimide; N-(8-bromooctyl)phthalimide; N-(9-bromononyl)phthalimide; N-(10-bromododecyl)phthalimide; N-(11-bromoundecyl)phthalimide; N-(12-bromodocecyl)phthalimide; N-(13-bromotridecyl)phthalimide; N-(14-bromotetradecyl)phthalimide; N-(15-bromopentadecyl)phthalimide; N-(16-bromohexadecyl)-phthalimide; N-( 17-bromoheptadecyl)phthalimide; N-(18-bromooctadecyl)phthalimide; N-(19-bromononadecyl)phthalimide; N-(3-bromo-2-methylpropyl)phthalimide; N-(4-bromo-2-methyl-3-ethylbutyl)phthalimide; N-(3-bromo-2,2-diethylpropyl)phthalimide; N-(4-bromo-3-propylbutyl)phthalimide; N-(10-bromo-2,8-dibutyldecyl)phthalimide; N-(8-bromo-6,6-dimethyloctyl)phthalimide; N-(8-bromo-6-propyl-6-butyloctyl)phthalimide; N-(4-bromo-2-methylbutyl)phthalimide; N-(5-bromo-2-methylpentyl)phthalimide; N-(5-bromo-3-methylpentyl)phthalimide; N-(6-bromo-2-ethylhexyl)phthalimide; N-( 5-bromo-3-penten-2-one)phthalimide; N-(4-bromo-3-methyl-2-butanol)phthalimide; N-(8-bromo-3-amino-4-chloro-2-cyanooctyl)phthalimide; N-(7-bromo-3-methoxy-4-heptanal)phthalimide; N-(4-bromo-2-iodo-3-nitrobutyl)phthalimide; N-(12-bromo-4-isopropoxydodecyl)phthalimide; N-(10-bromo-4-azido-2-nitrodecyl)phthalimide; N-(9-bromo-5-mercaptononyl)phthal-imide; N-(5-bromo-4-aminopentenyl) phthalimide; N-(5-bromopenten-2-yl)phthalimide; N-(3-bromoallyl)phthalimide; N-(4-bromocrotyl)phthalimide; N-(3-bromopropargyl)phthalimide; N-(1-bromonaphth-4-yl)phthalimide; N-(2-bromoanthrac-7-yl)phthalimide; and N-(2-bromophenanthr-6-yl)phthalimide. Such halide compounds are then reacted with an appropriate 2'-oxygen, 2'-sulfur or 2'-amine nucleoside.

In addition to amines (—NH$_2$), further preferred reactive moieties suitable for the functional groups of the invention include hydrazines (—NH—NH—), hydroxylamines (—NH—OH), semicarbazides (—NH—C(O)—NH—NH$_2$), thiosemicarbazides (—NH—C(S)—NH—NH$_2$), hydrazones (—N=NH) , hydrazides (—C(O)—NH—NH$_2$), alcohols (—OH), thiols (—SH), and aldehydes (—CH=O).

To introduce a nucleotide having a hydrazine-functionalized space-spanning group at its 2'-position into desired oligonucleotide sequences, 5'-dimethoxytrityl-2'-O-, -2'-S- or -2'-NH-(space-spanning group-N-benzylcarbazide) nucleoside phosphoramidites are synthesized. Once an oligonucleotide incorporating these nucleotides is synthesized, the hydrazine functionality is generated by reduction of the carbazide with palladium on charcoal.

To introduce a nucleotide having a hydroxylamine-functionalized space-spanning group at its 2'-position within desired oligonucleotide sequences, 5'-dimethoxytrityl-2'-O-, -2'-S- or -2'-NH-(space-spanning group-O-phthalimide-)nucleoside phosphoramidites are synthesized. Once an oligonucleotide incorporating these nucleotides is synthesized, the hydroxylamine functionality is generated by treatment of the oligonucleotide with methylhydrazine. Semicarbazide and thiosemicarbazide functionalities on space-spanning groups can be introduced directly without protective groups. 5'-Dimethoxytrityl-2'-O-, 2'-S- or 2'-NH-(alkylsemicarbazide)-nucleoside phosphoramidites are synthesized and incorporated into desired oligonucleotides to provide a semicarbazide functionalized space-spanning group attached to the 2'-position of a component nucleotide of an oligonucleotide.

Hydrazide functionalities are formed on space-spanning groups via reaction of hydrazine with an nucleotide bearing a 2'-O-alkylester. Alcohol functionalities can be formed on space-spanning groups via $\Omega$-bromo alcohols. The alcohol hydroxyl group is protected with a tetrahydropyran (THP) blocking group. The THP-protected compound is then reacted with an activated nucleoside to attach the THP-protected compound at the 2'-position of the nucleoside. After oligonucleotide synthesis, the THP blocking group is removed to expose the alcoholic functionality. Thiol functionalities can be directly formed via ring opening of a 2,2'-anhydro pyrimidine nucleoside using $\alpha,\Omega$-dithiol compounds. Alternatively, the thiol functionality of space-spanning compounds can be protected with S-trityl protecting groups. After oligonucleotide synthesis, the S-trityl protecting groups are removed with silver nitrate.

Aldehydes used as active functional groups in the formation of cross-linkages can be "masked" as protected aldehydes or aldehyde precursors during initial oligonucleotide synthesis. The aldehyde is generated prior to cross-linking from the protected aldehyde or aldehyde precursor and is utilized as one of the reactants for the formation of a covalent cross-linkage. Representative protected aldehydes are C-formyl, o-methylaminobenzenethio, aryl substituted imidazolidino moieties such as di-phenylimidazolidino, dithianes, bis(p-nitrophenoxy) and acetals. Particularly preferred acetals are di-aralkyl acetals such as bis(o-nitrobenzyl) acetals that are removed via catalytic hydrogenolysis. The diphenylimidazolidino group, which is removed via hydrazine hydrate/sodium cyanoborohydride treatment, is also particularly preferred. Aldehyde precursors include nitriles, alcohols and esters. Nitriles and esters are reduced to their corresponding aldehydes, while alcohols are oxidized to their corresponding aldehydes. Nitriles can be treated with hydrazine, followed by reduction with sodium cyanoborohydride. Esters can be reduced with lithium aluminum hydride. Alcohols can be oxidized under mild oxidation conditions such as Pfitzner-Moffat conditions. See, *J. Am. Chem. Soc.*, 1965, 87, 5661. Such conditions have been used by Hansske, et al., *Tetrahedron*, 1984, 40, 125, to oxidize 2' or 3' hydroxyl groups of various nucleosides using both a chromic acid oxidation reagent as well as a DMSO/Ac$_2$O oxidation reagent.

Aldehyde precursors and protected aldehydes can be used both at the nucleoside/nucleotide level and at the oligonucleotide level. Individual nucleotides (or their nucleoside precursors) incorporating an aldehyde precursor or protected aldehyde can be directly incorporated into an oligonucleotide. Alternately, an aldehyde precursor can be converted to a protected aldehyde, as with C-formyl protected aldehydes, and then directly incorporated into an oligonucleotide. Upon synthesis of the oligonucleotide, the aldehyde is regenerated from the protected aldehyde or generated from the aldehyde precursor and the oligonucleotide strand is cross-linked with a further oligonucleotide strand or with a further region of the same oligonucleotide strand. Use of aldehyde precursors is suggested for certain oligonucleotides, such as mimics of pyrimidine tract sequences located upstream from gene splice junctions. One such pyrimidine tract sequence includes the sequence CCC CTC CCC. Since such tracts only contain pyrimidine nucleotides, acidic oxidation conditions used for conversion of alcohols to aldehydes will not result in acidic de-purination or acidic strand cleavage of the oligonucleotide.

As will be recognized, hydrazine, hydroxylamine, semicarbazide, thiosemicarbazide, hydrazone, hydrazide, alcohol or thiol functional groups on one space-spanning group can be reacted with an aldehydic group (a —CH=O group) on a further space-spanning group as, for example, in the above-described embodiment wherein a 2'-ribose to 2'-ribose linkage is formed. These functional groups also can be reacted with an aldehydic group at the C1'-position of an abasic site to form a 2'-ribose to C1'-ribose linkage. Alternatively, these functional groups can be reacted with one of the aldehydic groups of a 2',3'-dialdehyde 3'-terminal nucleoside to form a 2'-ribose to a seco-ribose linkage, or to form imine (—C=N—), hydrazone (—C=N—NH—), oxime (—O—N=CH—), semicarbazone (NH—C (O)—NH—N=C—), thiosemicarbazone (NH—C(S)—NH—N=C—), azine(—HC=N—N=CH—), hydrazide-hydrazone (—C(O)—NH—N=C—), hemiacetal(—CH (OH)—O—CH$_2$—) or thiohemiacetal (—CH(OH) S—CH$_2$—) cross-linkages.

When an aldehyde on a first strand reacts with an alcohol or a thioacetal on another strand or on a further region of the first strand, the resulting hemiacetal or thiohemiacetal theoretically can react with a further alcohol or thiol group. However, such reaction generally is not kinetically (entropically) favorable, as it usually occurs in a water solution or under other conditions in which the concentration of the further alcohol or thiol group is low.

In those embodiments of the invention wherein a cross-linkage is formed between a 2'-ribose on a first strand (or a first region of a single strand) and a 2'-ribose on another strand (or a further region of the single strand), space-spanning groups and reactive functionalities are attached to each of the strands (or regions of a single strand). The space-spanning groups and reactive functionalities are attached to the 2'-position of each of the strands (or regions of a single strand), as above, utilizing connecting atoms. The strand or strands are then cross-linked by reaction of the reactive functionalities. Accordingly, the reactive functionalities can each be considered "bond precursors" or "bond means" since they together form a covalent bond.

Depending upon the reactive functionality on each of the strands (or regions of a single strand), a covalent bond will be formed as an integral part of the cross-linkage. When a thiol group is the active functionality on each of the strands, oxidization results in a disulfide cross-linkage. When an aldehyde is the functional group on one strand (or a first region on a single strand) and an amine is the functional group on the further strand (or further region on a single strand), an imine (—N=CH—, Schiff's base) cross-linkage results. The imine cross-linkage can be reduced to an amine (—NH—CH$_2$—) using a reducing agent such as sodium cyanoborohydride.

Reaction of a hydrazine (—NH—NH—) with an aldehyde yields a hydrazone (—HC=N—NH—) cross-linkage, while reaction of a hydroxylamine (HO—N—) with an aldehyde yields an oxime (—O—N=CH—) cross-linkage. Reaction of an aldehyde with a hydrazide (—C(O)—NH—NH$_2$) yields a hydrazide-hydrazone (—C(O)—NH—N=CH—) cross-linkage, reaction of an aldehyde with a semicarbazide (—NH—C(O)—NH—NH$_2$) yields a semicarbazone (—NH—C(O)—NH—N=C—) cross-linkage, and reaction of an aldehyde with a thiosemicarbazide (—NH—C(S)—NH—NH$_2$) yields a thiosemicarbazone (—NH—C(S)—NH—N=C—) cross-linkage. The hydrazone, oxime, hydrazide-hydrazone, semicarbazone and thiosemicarbazone linkages can be reduced to corresponding hydrazine, hydroxylamine, hydrazide-hydrazine, semicarbazide and thiosemicarbazide, respectively, if desired.

The active functional groups on the space-spanning moieties can be reacted with both heterobifunctional and homobifunctional groups. As will be recognized, formaldehyde is a homobifunctional group when it is reacted with two amines. Reaction of formaldehyde with amine functional groups that are attached to each of two strands (or regions of a single strand) yields an aminoalkylamine (—NH—CH$_2$—NH—) linkage.

Hydrazine also can be used as a bifunctional group to join strands that each have a space-spanning group terminated with an aldehyde. The hydrazine adds to a first aldehyde group to form an aldehyde-hydrazone that, in turn, reacts with the second aldehyde to yield an azine (—CH=N—N=CH—) cross-linkage.

Heterobifunctional groups allow the use of one active functionality on one strand (or a region of a single strand) and the use of a different active functionality on another strand (or another region of a single strand). Thus, one strand could have an amine functionality on an end of its space-spanning group and another strand could have a thiol functionality on the end of its space-spanning group.

Space-spanning groups on one of the strands (or region of a single strand) may not be necessary where hetero-bifunctional groups or certain of the above-noted active functionalities are employed. An attaching group, for example a 2'-amino or 2'-thio of a 2'-substituted-2'-deoxy-erythro-pentofuranosyl moiety, could be used directly as an active functionality. The space-spanning group and its active functionality from the other strand could react directly with this 2'-positioned active functionality. For example a 2'-deoxy-2'-thio-erythro-pentofuranosyl sugar could be utilized as the sugar moiety of a selected nucleotide on one strand. An omega thiol group on the space-spanning group of a complementary duplex strand can then be coupled to the first 2'-thio group via a disulfide linkage. Other 2' groups suitable for this type of cross-linkage include 2'-amino groups. A 2'-keto group also could be reacted with a suitable hydrazine or other reactive functionality.

A variety of heterobifunctional coupling reagents are available from commercial sources including Pierce (Rockford, Ill.). These reagents include 1-ethyl-3-(3-dimethylaminopropyl)carbodiimide (a water soluble DCC type coupling reagent), bifunctional imidoesters such as dimethyl adipimidate dihydrochloride, dimethyl pimelimidate dihydrochloride, and dimethyl 3,3'-dithiobispropionimidate dihydrochloride (for coupling amine groups), and 2-iminothiolane (for coupling amines thiols). Coupling reagents also include compounds having N-hydroxysuccinimide moieties that react with amines, compounds having internal disulfide bonds that can be released to expose an active thiol moiety that can be further coupled via a disulfide bond with a further thiol functionality, and compounds having sulfosuccinimidyl groups (e.g., N-hydroxysulfosuccinimide) that have different reactivity toward amines than N-hydroxysuccinimides. Coupling reagents further include pyridyl-disulfides that exchange with free thiol moieties, active halogen species such as β-carbonyl alkylhalides, e.g. iodo acetamide, maleimide moieties and photoreactive aryl azides such as phenyl azide. Also, thioisocyanates can be used to couple with active functionalities on space-spanning groups.

The various functional groups of the bifunctional cross-linkers are joined together with suitable linking atoms. Representative, commercially available bifunctional compounds include sulfosuccinimidyl 4-(N-maleimidoethyl)cyclohexane-1-carboxylate, N-succinimidyl 3-(2-pyridyldithio)propionate, N-sulfosuccinimidyl(4-iodoacetyl)aminobenzoate, sulfosuccinimidyl-4-(p- maleimidophenyl)butyrate, m-maleimido-benzoyl-N-hydroxysulfosuccinimide ester, succinimidyl 4-(N-maleimidomethyl)cyclohexane-1-carboxylate, bismaleimidohexane, disulfosuccinimidyl tartrate, ethylene glycolbis(succinimidylsuccinate), dithiobis(succinimidylpropionate), disuccinimidyl suberate, N-hydroxysuccinimidyl-4-azidosalicylic acid, N-5-azido-2-nitrobenzoyloxysuccinimideandsulfonsuccinimidyl 2-(m-azido-o-nitrobenzamido)-ethyl-1,3'-dithiopropionate. Each of these bifunctional groups are reacted with an appropriate active functionality on the space-spanning group. Thus, oligonucleotide strands (or regions of a single strand) bearing the space-spanning groups are cross-linked through the bifunctional group.

The 6-bromo-5,5-dimethoxyhexanohydrazide and N-hydroxysuccinimidyl iodoacetate reagents disclosed by Summerton, et al. and Meyer, et al., respectively, in the references cited above can also be used as heterobifunctional cross-linking reagents. The hydrazine moiety of the Summerton reagent and the succinimidyl moiety of the Meyer reagent can be linked to one strand of duplex strands and the other strand can be linked to the bromoketone or the iodoacetamido portions of these reagents. For instance, the hydrazine functionality of the Summerton reagent would first be reacted with an aldehydic functionality on one strand, the α-haloketal functionality of the reagent would be activated to an α-haloketone via pH adjustment, and the α-haloketone would then be further reacted with an amine or thiol functionality on the other strand. The active succinimide functionality of the Meyer reagent would be linked to a first amine functionality on a first strand and the resulting iodoacetamidoalkyl functionality would be linked to a further amine or thiol functionality on the other strand.

Since both the Summerton and Meyer reagents can be used to join two amine functionalities (two hydrazine functionalities in the case of the Summerton reagent), they can also be considered homobifunctional linking reagents. Neither the Summerton reagent nor the Meyer reagent are used in accordance with the invention to couple duplex strands via the 7-position of a purine ring. Thus, no charged (i.e., chemically unstable) species are formed but, rather uncharged, chemically stable cross-linkages of the structures —CH$_2$—S—CH$_2$—C(O)—CH$_2$— and —CH$_2$—NH—CH$_2$—C(O)—CH$_2$—.

By terminating a first oligonucleotide strand at its 3' end with a terminal ribofuranosyl nucleoside, cross-linking to a further oligonucleotide strands (or to a further region of a single strand) can be effected via one of two mechanisms. The first mechanism involves generation of a seco ribose by, for example, periodate oxidation of the 2',3' hydroxyl groups of the 3'-terminal ribose. [See, e.g., Lemaitre, *Proc. Natl. Acad. Sci. USA*, 1986, 84, 648; Chang, *Biochem. J.*, 1981, 199, 281; and Easterbrook-Smith, *Eur. J. Biochem*, 1976, 62, 125.] Such oxidation yields a 2',3' di-aldehyde (a seco ribose), which is reacted with a second strand (or a further region of a single strand) that includes a space-spanning group bearing an active amine functionality. Such reaction yields a Schiff's base, which is reduced with, for example, sodium cyanoborohydride, to form an amine cross-linker having an amine group directly coupled to the seco ribose of the 3'-terminal nucleoside of the first oligonucleotide strand.

The second mechanism involves formation of an acetal cross-linkage from the 2',3'-hydroxyl groups of the terminal ribose. To form the acetal linkage, the hydroxyl groups of the terminal ribose are reacted with an aldehyde group on a space-spanning group on the second strand (or further region of a single strand). Acetals of this type have been utilized to attach a nitrogen mustard to a terminal ribose, as described by Knorre, et al., Nucleotide and Oligonucleotide Derivatives as Enzyme and Nucleic Acid Targeted Irreversible Inhibitors, Chemical Aspects, G. Weber (Ed.), Advances Press, Oxford, 1986, pp. 277–299. The nitrogen mustard was then further reacted with a complementary sequence of a short oligonucleotide. Significantly, the cross-linkage was formed via the nitrogen mustard, not via the acetal. As noted above, cross-linkages formed via nitrogen mustards generate charged species that are chemically unstable. The present invention employs an acetal, which does not generate a charged species, to effect cross-linking.

Taken together, the space-spanning groups, the functional groups, and the connecting atoms comprise a moiety selected from the group consisting of: $C_1$–$C_{20}$ straight chain alkylamine, $C_1$–$C_{20}$ straight chain O-alkylamine, $C_1$–$C_{20}$ straight chain S-alkylamine, $C_1$–$C_{20}$ straight chain NH-alkylamine, $C_1$–$C_{20}$ straight chain substituted alkylamine, $C_1$–$C_{20}$ straight chain substituted O-alkylamine, $C_1$–$C_{20}$ straight chain substituted S-alkylamine, $C_1$–$C_{20}$ straight chain substituted NH-alkylamine, $C_2$–$C_{50}$ branched chain alkylamine, $C_2$–$C_{50}$ branched chain O-alkylamine, $C_2$–$C_{50}$ branched chain S-alkylamine, $C_2$–$C_{50}$ branched chain NH-alkylamine, $C_2$–$C_{50}$ branched chain substituted alkylamine, $C_2C_{50}$ branched chain substituted O-alkylamine, $C_2$–$C_{50}$ branched chain substituted S-alkylamine, $C_2$–$C_{50}$ branched chain substituted NH-alkylamine, $C_2$–$C_{20}$ straight chain alkenylamine, $C_2$–$C_{20}$ straight chain O-alkenylamine, $C_2$–$C_{20}$ straight chain S-alkenylamine, $C_2$–$C_{20}$ straight chain NH-alkenylamine, $C_2$–$C_{20}$ straight chain substituted alkenylamine, $C_2$–$C_{20}$ straight chain substituted O-alkenylamine, $C_2$–$C_{20}$ straight chain substituted S-alkenylamine, $C_2$–$C_{20}$ straight chain substituted NH-alkenylamine, $C_3$–$C_{50}$ branched chain alkenylamine, $C_3$–$C_{50}$ branched chain O-alkenylamine, $C_3$–$C_{50}$ branched chain S-alkenylamine, branched chain NH-alkenylamine, $C_1$–$C_{50}$ branched chain substituted alkenylamine, $C_3$–$C_{50}$ branched chain substituted O-alkenylamine, $C_3$–$C_{50}$ branched chain substituted S-alkenylamine, $C_3$–$C_{50}$ branched chain substituted NH-alkenylamine, $C_2$–$C_{20}$ straight chain alkynylamine, $C_2$–$C_{20}$ straight chain O-alkynylamine, $C_2$–$C_{20}$ straight chain S-alkynylamine, $C_2$–$C_{20}$ straight chain NH-alkynylamine, $C_2$–$C_{20}$ straight chain substituted alkynylamine, $C_2$–$C_{20}$ straight chain substituted O-alkynylamine, $C_2$–$C_{20}$ straight chain substituted S-alkynylamine, $C_2$–$C_{20}$ straight chain substituted NH-alkynylamine, $C_3$–$C_{50}$ branched chain alkynylamine, $C_2$–$C_{50}$ branched chain O-alkynylamine, $C_3$–$C_{50}$ branched chain S-alkynylamine, $C_3$–$C_{50}$ branched chain NH-alkynylamine, $C_3$–$C_{50}$ branched chain substituted alkynylamine, $C_3$–$C_{50}$ branched chain substituted O-alkynylamine, $C_3$–$C_{50}$ branched chain substituted S-alkynylamine, $C_3$–$C_{50}$ branched chain substituted NH-alkynylamine, $C_1$–$C_{20}$ straight chain alkylhydrazine, $C_1$–$C_{20}$ straight chain O-alkylhydrazine, $C_1$–$C_{20}$ straight chain S-alkylhydrazine, $C_1$–$C_{20}$ straight chain NH-alkylhydrazine, $C_1$–$C_{20}$ straight chain substituted alkylhydrazine, $C_1$–$C_{20}$ straight chain substituted O-alkylhydrazine, $C_1$–$C_{20}$ straight chain substituted S-alkylhydrazine, $C_1$–$C_{20}$ straight chain substituted NH-alkylhydrazine, $C_2$–$C_{50}$ branched chain alkylhydrazine, $C_2$–$C_{50}$ branched chain O-alkylhydrazine, $C_2$–$C_{50}$ branched chain S-alkylhydrazine, $C_2$–$C_{50}$ branched chain NH-alkylhydrazine, $C_2$–$C_{50}$, branched chain substituted alkylhydrazine, $C_2$–$C_{50}$ branched chain substituted O-alkylhydrazine, $C_2$–$C_{50}$ branched chain substituted S-alkylhydrazine, $C_2$–$C_{50}$ branched chain substituted NH-alkylhydrazine, $C_2$–$C_{20}$ straight chain alkenylhydrazine, $C_2$–$C_{20}$ straight chain O-alkenylhydrazine, $C_2$–$C_{20}$ straight chain S-alkenylhydrazine, $C_2$-$C_{20}$ straight chain NH-alkenylhydrazine, $C_2$-$C_{20}$ straight chain substituted alkenylhydrazine, $C_2$-$C_{20}$ straight chain substituted O-alkenylhydrazine, $C_2$-$C_{20}$ straight chain substituted S-alkenylhydrazine, $C_2$-$C_{20}$ straight chain substituted NH-alkenylhydrazine, $C_3$-$C_{50}$ branched chain alkenylhydrazine, branched chain O-alkenylhydrazine, $C_3$-$C_{50}$ branched chain S-alkenylhydrazine, $C_3$-$C_{50}$ branched chain NH-alkenylhydrazine, $C_3$-$C_{50}$ branched chain substituted alkenylhydrazine, $C_3$-$C_{50}$ branched chain substituted O-alkenylhydrazine, $C_3$-$C_{50}$ branched chain substituted S-alkenylhydrazine, $C_3$-$C_{50}$ branched chain substituted NH-alkenylhydrazine, $C_2$-$C_{20}$ straight chain alkynylhydrazine, $C_2$-$C_{20}$ straight chain O-alkynylhydrazine, $C_2$-$C_{20}$ straight chain S-alkynylhydrazine, $C_2$-$C_{20}$ straight chain NH-alkynylhydrazine, $C_2$-$C_{20}$ straight chain substituted alkynylhydrazine, $C_2$-$C_{20}$ straight chain substituted O-alkynylhydrazine, $C_2$-$C_{20}$ straight chain substituted S-alkynylhydrazine, $C_2$-$C_{20}$ straight chain substituted NH-alkynylhydrazine, $C_3$-$C_{50}$ branched chain alkynylhydrazine, $C_3$-$C_{50}$ branched chain O-alkynylhydrazine, $C_3$-$C_{50}$ branched chain S-alkynylhydrazine, $C_3$-$C_{50}$ branched chain NH-alkynylhydrazine, $C_3$-$C_{50}$ branched chain substituted alkynylhydrazine, $C_3$-$C_{50}$ branched chain substituted O-alkynylhydrazine, $C_3$-$C_{50}$ branched chain substituted S-alkynylhydrazine, $C_3$-$C_{50}$ branched chain substituted NH-alkynylhydrazine, $C_1$-$C_{20}$ straight chain alkylhydroxylamine, $C_1$-$C_{20}$ straight chain O-alkylhydroxylamine, $C_1$-$C_{20}$ straight chain S-alkylhydroxylamine, $C_1$-$C_{20}$ straight chain NH-alkylhydroxylamine, $C_1$-$C_{20}$ straight chain substituted alkylhydroxylamine, $C_1$-$C_{20}$ straight chain substituted O-alkylhydroxylamine, $C_1$-$C_{20}$ straight chain substituted S-alkylhydroxylamine, $C_1$-$C_{20}$ straight chain substituted NH-alkylhydroxylamine, $C_2$-$C_{50}$ branched chain alkylhydroxylamine, $C_2$-$C_{50}$ branched chain O-alkylhydroxylamine, $C_2$-$C_{50}$ branched chain S-alkylhydroxylamine, $C_2$-$C_{50}$ branched chain NH-alkylhydroxylamine, $C_2$-$C_{50}$ branched chain substituted alkylhydroxylamine, $C_2$-$C_{50}$ branched chain substituted O-alkylhydroxylamine, $C_2$-$C_{50}$ branched chain substituted S-alkylhydroxylamine, $C_2$-$C_{50}$ branched chain substituted NH-alkylhydroxylamine, $C_2$-$C_{20}$ straight chain alkenylhydroxylamine, $C_2$-$C_{20}$ straight chain O-alkenylhydroxylamine, $C_2$-$C_{20}$ straight chain S-alkenylhydroxylamine, $C_2$-$C_{20}$ straight chain NH-alkenylhydroxylamine, $C_2$-$C_{20}$ straight chain substituted alkenylhydroxylamine, $C_2$-$C_{20}$ straight chain substituted O-alkenylhydroxylamine, $C_2$-$C_{20}$ straight chain substituted S-alkenylhydroxylamine, $C_2$-$C_{20}$ straight chain substituted NH-alkenylhydroxylamine, $C_3$-$C_{50}$ branched chain alkenylhydroxylamine, $C_3$-$C_{50}$ branched chain O-alkenylhydroxylamine, $C_3$-$C_{50}$ branched chain S-alkenylhydroxylamine, $C_1$-$C_{50}$ branched chain NH-alkenylhydroxylamine, $C_3$-$C_{50}$ branched chain substituted alkenylhydroxylamine, $C_3$-$C_{50}$ branched chain substituted O-alkenylhydroxylamine, $C_3$-$C_{50}$ branched chain substituted S-alkenylhydroxylamine, $C_3$-$C_{50}$ branched chain substituted NH-alkenylhydroxylamine, $C_2$-$C_{20}$ straight chain alkynylhydroxylamine, $C_2$-$C_{20}$ straight chain O-alkynylhydroxylamine, $C_2$-$C_{20}$ straight chain S-alkynylhydroxyamine, $C_2$-$C_{20}$ straight chain NH-alkynylhydroxylamine, $C_2$-$C_{20}$ straight chain substituted alkynylhydroxylamine, $C_2$-$C_{20}$ straight chain substituted O-alkynylhydroxylamine, $C_2$-$C_{20}$ straight chain substituted S-alkynylhydroxylamine, $C_2$-$C_{20}$ straight chain substituted NH-alkynylhydroxylamine, $C_3$-$C_{50}$ branched chain alkynylhydroxylamine, $C_2$-$C_{50}$ branched chain O-alkynylhydroxylamine, $C_3$-$C_{50}$ branched chain S-alkynylhydroxylamine, $C_3$-$C_{50}$ branched chain NH-alkynylhydroxylamine, $C_3$-$C_{50}$ branched chain substituted alkynylhydroxylamine, $C_3$-$C_{50}$ branched chain substituted O-alkynylhydroxylamine, $C_3$-$C_{50}$ branched chain substituted S-alkynylhydroxylamine, $C_3$-$C_{50}$ branched chain substituted NH-alkynylhydroxylamine, $C_1$-$C_{20}$ straight chain alkylsemicarbazide, $C_1$-$C_{20}$ straight chain O-alkylsemicarbazide, $C_1$-$C_{20}$ straight chain S-alkylsemicarbazide, $C_1$-$C_{20}$ straight chain NH-alkylsemicarbazide, $C_1$-$C_{20}$ straight chain substituted alkylsemicarbazide, $C_1$-$C_{20}$ straight chain substituted O-alkylsemicarbazide, $C_1$-$C_{20}$ straight chain substituted S-alkylsemicarbazide, $C_1$-$C_{20}$ straight chain substituted NH-alkylsemicarbazide, $C_2$-$C_{50}$ branched chain alkylsemicarbazide, $C_2$-$C_{50}$ branched chain O-alkylsemicarbazide, $C_2$-$C_{50}$ branched chain S-alkylsemicarbazide, $C_2$-$C_{50}$ branched chain NH-alkylsemicarbazide, $C_2$-$C_{50}$ branched chain substituted alkylsemicarbazide, $C_2$-$C_{50}$ branched chain substituted O-alkylsemicarbazide, $C_2$-$C_{50}$ branched chain substituted S-alkylsemicarbazide, $C_2$-$C_{50}$ branched chain substituted NH-alkylsemicarbazide, $C_2$-$C_{20}$ straight chain alkenylsemicarbazide, $C_2$-$C_{20}$ straight chain O-alkenylsemicarbazide, $C_2$-$C_{20}$ straight chain S-alkenylsemicarbazide, $C_2$-$C_{20}$ straight chain NH-alkenylsemicarbazide, $C_3$-$C_{50}$ straight chain substituted alkenylsemicarbazide, $C_2$-$C_{20}$ straight chain substituted O-alkenylcarbazide, $C_2$-$C_{20}$ straight chain substituted S-alkenylsemicarbazide, $C_2$-$C_{20}$ straight chain substituted NH-alkenylsemicarbazide, $C_3$-$C_{50}$ branched chain alkenylsemicarbazide, $C_3$-$C_{50}$ branched chain O-alkenylsemicarbazide, $C_3$-$C_{50}$ branched chain S-alkenylsemicarbazide, $C_3$-$C_{50}$ branched chain NH-alkenylsemicarbazide, $C_3$-$C_{50}$ branched chain substituted alkenylsemicarbazide, $C_3$-$C_{50}$ branched chain substituted O-alkenylsemicarbazide, $C_3$-$C_{50}$ branched chain substituted S-alkenylsemicarbazide, $C_3$-$C_{50}$ branched chain substituted NH-alkenylsemicarbazide, $C_2$-$C_{20}$ straight chain alkynylsemicarbazide, $C_2$-$C_{20}$ straight chain O-alkynylsemicarbazide, $C_2$-$C_{20}$ straight chain S-alkynylsemicarbazide, $C_2$-$C_{20}$ straight chain NH-alkynylsemicarbazide, $C_2$-$C_{20}$ straight chain substituted alkynylsemicarbazide, $C_2$-$C_{20}$ straight chain substituted O-alkynylsemicarbazide, $C_2$-$C_{20}$ straight chain substituted S-alkynylsemicarbazide, $C_2$-$C_{20}$ straight chain substituted NH-alkynylsemicarbazide, $C_3$-$C_{50}$ branched chain alkynylsemicarbazide, $C_2$-$C_{50}$ branched chain O-alkynylsemicarbazide, $C_3$-$C_{50}$ branched chain S-alkynylsemicarbazide, $C_3$-$C_{50}$ branched chain NH-alkynylsemicarbazide, $C_3$-$C_{50}$ branched chain substituted alkynylsemicarbazide, $C_3$-$C_{50}$ branched chain substituted O-alkynylsemicarbazide, $C_3$-$C_{50}$ branched chain substituted S-alkynylsemicarbazide, $C_3$-$C_{50}$ branched chain substituted NH-alkynylsemicarbazide, $C_1$-$C_{20}$ straight chain alkylthiosemicarbazide, $C_1$-$C_{20}$ straight chain O-alkylthiosemicarbazide, $C_1$-$C_{20}$ straight chain S-alkylthiosemicarbazide, $C_1$-$C_{20}$ straight chain NH-alkylthiosemicarbazide, $C_1$-$C_{20}$ straight chain substituted alkylthiosemicarbazide, $C_1$-$C_{20}$ straight chain substituted O-alkylthiosemicarbazide, $C_1$-$C_{20}$ straight chain substituted S-alkylthiosemicarbazide, $C_1$-$C_{20}$ straight chain substituted NH-alkylthiosemicarbazide, $C_2$-$C_{50}$ branched chain alkylthiosemicarbazide, $C_2$-$C_{50}$ branched chain O-alkylthiosemicarbazide, $C_2$-$C_{50}$ branched chain S-alkylthiosemicarbazide, $C_2$-$C_{50}$ branched chain NH-alkylthiosemicarbazide, $C_2$-$C_{50}$ branched chain substituted alkylthiosemicarbazide, $C_2$-$C_{50}$ branched chain substituted O-alkylthiosemicarbazide, $C_2$-$C_{50}$ branched chain substituted S-alkylthiosemicarbazide, $C_2$-$C_{50}$ branched chain substituted NH-alkylthiosemicarbazide, $C_2$-$C_{20}$ straight chain alkenylthiosemicarbazide, $C_2$-$C_{20}$ straight chain O-alkenylthiosemicarbazide, $C_2$-$C_{20}$ straight chain S-alkenylthiosemicarbazide, $C_2$–$C_{20}$ straight chain NH-alkenylthiosemicarbazide, $C_2$–$C_{20}$ straight chain substituted alkenylthiosemicarbazide, $C_2$–$C_{20}$ straight chain substituted O-alkenylthiosemicarbazide, $C_2$–$C_{20}$ straight chain substituted S-alkenylthiosemicarbazide, $C_2$–$C_{20}$ straight chain substituted NH-alkenylthiosemicarbazide, $C_3$–$C_{50}$ branched chain alkenylthiosemicarbazide, $C_3$–$C_{50}$ branched chain O-alkenylthiosemicarbazide, $C_3$–$C_{50}$ branched chain S-alkenylthiosemicarbazide, $C_3$–$C_{50}$ branched chain NH-alkenylthiosemicarbazide, $C_3$–$C_{50}$ branched chain substituted alkenylthiosemicarbazide, $C_3$–$C_{50}$ branched chain substituted O-alkenylthiosemicarbazide, $C_3$–$C_{50}$ branched chain substituted S-alkenylthiosemicarbazide, $C_3$–$C_{50}$ branched chain substituted NH-alkenylthiosemicarbazide, $C_2$–$C_{20}$ straight chain alkynylthiosemicarbazide, $C_2$–$C_{20}$ straight chain O-alkynylthiosemicarbazide, $C_2$–$C_{20}$ straight chain S-alkynylthiosemicarbazide, $C_2$–$C_{20}$ straight chain NH-alkynylthiosemicarbazide, $C_2$–$C_{20}$ straight chain substituted alkynylthiosemicarbazide, $C_2$–$C_{20}$ straight chain substituted O-alkynylthiosemicarbazide, $C_2$–$C_{20}$ straight chain substituted S-alkynylthiosemicarbazide, $C_2$–$C_{20}$ straight chain substituted NH-alkynylthiosemicarbazide, $C_3$–$C_{50}$ branched chain alkynylthiosemicarbazide, $C_2$–$C_{50}$ branched chain O-alkynylthiosemicarbazide, $C_3$–$C_{50}$ branched chain S-alkynylthiosemicarbazide, $C_3$–$C_{50}$ branched chain NH-alkynylthiosemicarbazide, $C_3$–$C_{50}$ branched chain substituted alkynylthiosemicarbazide, $C_3$–$C_{50}$ branched chain substituted O-alkynylthiosemicarbazide, $C_3$–$C_{50}$ branched chain substituted S-alkynylthiosemicarbazide, $C_3$–$C_{50}$ branched chain substituted NH-alkynylthiosemicarbazide, $C_1$–$C_{20}$ straight chain alkylhydrazone, $C_1$–$C_{20}$ straight chain O-alkylhydrazone, $C_1$–$C_{20}$ straight chain S-alkylhydrazone, $C_1$–$C_{20}$ straight chain NH-alkylhydrazone, $C_1$–$C_{20}$ straight chain substituted alkylhydrazone, $C_1$–$C_{20}$ straight chain substituted O-alkylhydrazone, $C_1$–$C_{20}$ straight chain substituted S-alkylhydrazone, $C_1$–$C_{20}$ straight chain substituted NH-alkylhydrazone, $C_2$–$C_{50}$ branched chain alkylhydrazone, $C_2$–$C_{50}$ branched chain O-alkylhydrazone, $C_2$–$C_{50}$ branched chain S-alkylhydrazone, $C_2$–$C_{50}$ branched chain NH-alkylhydrazone, $C_2$–$C_{50}$ branched chain substituted alkylhydrazone, $C_2$–$C_{50}$ branched chain substituted O-alkylhydrazone, $C_2$–$C_{50}$ branched chain substituted S-alkylhydrazone, $C_2$–$C_{50}$ branched chain substituted NH-alkylhydrazone, $C_2$–$C_{20}$ straight chain alkenylhydrazone, $C_2$–$C_{20}$ straight chain O-alkenylhydrazone, $C_2$–$C_{20}$ straight chain S-alkenylhydrazone, $C_2$–$C_{20}$ straight chain NH-alkenylhydrazone, $C_2$–$C_{20}$ straight chain substituted alkenylhydrazone, $C_2$–$C_{20}$ straight chain substituted O-alkenylhydrazone, $C_2$–$C_{20}$ straight chain substituted S-alkenylhydrazone, $C_2$–$C_{20}$ straight chain substituted NH-alkenylhydrazone, $C_3$–$C_{50}$ branched chain alkenylhydrazone, $C_3$–$C_{50}$ branched chain O-alkenylhydrazone, $C_3$–$C_{50}$ branched chain S-alkenylhydrazone, $C_3$–$C_{50}$ branched chain NH-alkenylhydrazone, $C_3$–$C_{50}$ branched chain substituted alkenylhydrazone, $C_3$–$C_{50}$ branched chain substituted O-alkenylhydrazone, $C_3$–$C_{50}$ branched chain substituted S-alkenylhydrazone, $C_3$–$C_{50}$ branched chain substituted NH-alkenylhydrazone, $C_2$–$C_{20}$ straight chain alkynylhydrazone, $C_2$–$C_{20}$ straight chain O-alkynylhydrazone, $C_2$–$C_{20}$ straight chain S-alkynylhydrazone, $C_2$–$C_{20}$ straight chain NH-alkynylhydrazone, $C_2$–$C_{20}$ straight chain substituted alkynylhydrazone, $C_2$–$C_{20}$ straight chain substituted O-alkynylhydrazone, $C_2$–$C_{20}$ straight chain substituted S-alkynylhydrazone, $C_2$–$C_{20}$ straight chain substituted NH-alkynylhydrazone, $C_{3-C50}$ branched chain alkynylhydrazide, $C_2$–$C_{50}$ branched chain O-alkynylhydrazide, $C_3$–$C_{50}$ branched chain S-alkynylhydrazide, $C_3$–$C_{50}$ branched chain NH-alkynylhydrazide, $C_3$–$C_{50}$ branched chain substituted alkynylhydrazide, $C_3$–$C_{50}$ branched chain substituted O-alkynylhydrazide, $C_3$–$C_{50}$ branched chain substituted S-alkynylhydrazide, $C_3$–$C_{50}$ branched chain substituted NH-alkynylhydrazide, $C_1$–$C_{20}$ straight chain alkanol, $C_1$–$C_{20}$ straight chain O-alkanol, $C_1$–$C_{20}$ straight chain S-alkanol, $C_1$–$C_{20}$ straight chain NH-alkanol, $C_1$–$C_{20}$ straight chain substituted alkanol, $C_1$–$C_{20}$ straight chain substituted O-alkanol, $C_1$–$C_{20}$ straight chain substituted S-alkanol, $C_1$–$C_{20}$ straight chain substituted NH-alkanol, $C_2$–$C_{50}$ branched chain alkanol, branched chain O-alkanol, $C_2$–$C_{50}$ branched chain S-alkanol, $C_2$–$C_{50}$ branched chain NH-alkanol, $C_2$–$C_{50}$ branched chain substituted alkanol, $C_2$–$C_{50}$ branched chain substituted O-alkanol, $C_2$–$C_{50}$ branched chain substituted S-alkanol, $C_2$–$C_{50}$ branched chain substituted NH-alkanol, $C_2$–$C_{20}$ straight chain alkenol, $C_2$–$C_{20}$ straight chain O-alkenol, $C_2$–$C_{20}$ straight chain S-alkenol, $C_2$–$C_{20}$ straight chain NH-alkenol, $C_2$–$C_{20}$ straight chain substituted alkenol, $C_2$–$C_{20}$ straight chain substituted O-alkenol, $C_2$–$C_{20}$ straight chain substituted S-alkenol, $C_2$–$C_{20}$ straight chain substituted NH-alkenol, $C_3$–$C_{50}$ branched chain alkenol, $C_3$–$C_{50}$ branched chain O-alkenol, $C_3$–$C_{50}$ branched chain S-alkenol, $C_3$–$C_{50}$ branched chain NH-alkenol, $C_3$–$C_{50}$ branched chain substituted alkenol, $C_3$–$C_{50}$ branched chain substituted O-alkenol, $C_3$–$C_{50}$ branched chain substituted S-alkenol, $C_3$–$C_{50}$ branched chain substituted NH-alkenol, $C_2$–$C_{20}$ straight chain alkynol, $C_2$–$C_{20}$ straight chain O-alkynol, $C_2$–$C_{20}$ straight chain S-alkynol, $C_2$–$C_{20}$ straight chain NH-alkynol, $C_2$–$C_{20}$ straight chain substituted alkynol, $C_2$–$C_{20}$ straight chain substituted O-alkynol, $C_2$–$C_{20}$ straight chain substituted S-alkynol, $C_2$–$C_{20}$ straight chain substituted NH-alkynol, $C_3$–$C_{50}$ branched chain alkynol, $C_2$–$C_{50}$ branched chain O-alkynol, $C_3$–$C_{50}$ branched chain S-alkynol, $C_3$–$C_{50}$ branched chain NH-alkynol, $C_3$–$C_{50}$ branched chain substituted alkynol, $C_3$–$C_{50}$ branched chain substituted O-alkynol, $C_3$–$C_{50}$ branched chain substituted S-alkynol, $C_3$–$C_{50}$ branched chain substituted NH-alkynol, $C_1$–$C_{20}$ straight chain alkanthiol, $C_1$–$C_{20}$ straight chain O-alkanthiol, $C_1$–$C_{20}$ straight chain S-alkanthiol, $C_1$–$C_{20}$ straight chain NH-alkanthiol, $C_1$–$C_{20}$ straight chain substituted alkanthiol, $C_1$–$C_{20}$ straight chain substituted O-alkanthiol, $C_1$–$C_{20}$ straight chain substituted S-alkanthiol, $C_1$–$C_{20}$ straight chain substituted NH-alkanthiol, $C_2$–$C_{50}$ branched chain alkanthiol, $C_2$–$C_{50}$ branched chain O-alkanthiol, $C_2$–$C_{50}$ branched chain S-alkanthiol, $C_2$–$C_{50}$ branched chain NH-alkanthiol, $C_2$–$C_{50}$ branched chain substituted alkanthiol, $C_2$–$C_{50}$ branched chain substituted O-alkanthiol, $C_2$–$C_{50}$ branched chain substituted S-alkanthiol, $C_2$–$C_{50}$ branched chain substituted NH-alkanthiol, $C_2$–$C_{20}$ straight chain alkenthiol, $C_2$–$C_{20}$ straight chain O-alkenthiol, $C_2$–$C_{20}$ straight chain S-alkenthiol, $C_2$–$C_{20}$ straight chain NH-alkenthiol, $C_2$–$C_{20}$ straight chain substituted alkenthiol, $C_2$–$C_{20}$ straight chain substituted O-alkenthiol, $C_2$–$C_{20}$ straight chain substituted S-alkenthiol, $C_2$–$C_{20}$ straight chain substituted NH-alkenthiol, $C_3$–$C_{50}$ branched chain alkenthiol, $C_3$–$C_{50}$ branched chain O-alkenthiol, $C_3$–$C_{50}$ branched chain S-alkenthiol, $C_3$–$C_{50}$ branched chain NH-alkenthiol, $C_3$–$C_{50}$ branched chain substituted alkenthiol, $C_3$–$C_{50}$ branched chain substituted O-alkenthiol, $C_3$–$C_{50}$ branched chain substituted S-alkenthiol, $C_3$–$C_{50}$ branched chain substituted NH-alkenthiol, $C_2$–$C_{20}$ straight chain alkynthiol, $C_2$–$C_{20}$ straight chain O-alkynthiol, $C_2$–$C_{20}$ straight chain S-alkynthiol, $C_2$–$C_{20}$ straight chain NH-alkynthiol, $C_2$–$C_{20}$ straight chain substituted alkynthiol, $C_2$–$C_{20}$ straight chain substituted O-alkynthiol, $C_2$–$C_{20}$ straight chain substituted S-alkynthiol, $C_2$–$C_{20}$ straight chain substituted NH-alkynthiol, $C_3$–$C_{50}$ branched chain alkynthiol, $C_2$–$C_{50}$ branched chain O-alkynthiol, $C_3$–$C_{50}$ branched chain S-alkynthiol, $C_3$–$C_{50}$ branched chain NH-alkynthiol, $C_3$–$C_{50}$ branched chain substituted alkynthiol, $C_3$–$C_{50}$ branched chain substituted O-alkynthiol, $C_3$–$C_{50}$ branched chain substituted S-alkynthiol and $C_3$–$C_{50}$ branched chain substituted NH-alkynthiol.

The present invention also provides oligonucleotide cross-linkers for connecting two oligonucleotide strands or for connecting two separate regions of a single strand. In certain embodiments, the cross-linkers are of a structure:

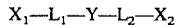

wherein $X_1$ is covalently connected to the first strand or to a first region of a single strand and $X_2$ is covalently connected to the second strand or to a further region of a single strand and where:

(i) $X_1$ and $X_2$, independently, are O, S, NH, $CH_2$ or CO;

$L_1$ and $L_2$, independently, are $C_1$–$C_{20}$ straight chain alkyl, $C_1$–$C_{20}$ straight chain substituted alkyl, $C_2$–$C_{50}$ branched chain alkyl, $C_2$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne, $C_3$–$C_{50}$ branched chain alkyne, $C_3$–$C_{50}$ branched chain substituted alkyne, polyamine, polyamide, polyester, polyethylene glycol, polyether, aryl, aralkyl or heterocyclic; and Y is an imine, amine, oxime, hydroxylamine, hydrazine, hydrazone, azine, hydrazide-hydrazone, amide, hydrazide, semicarbazide, semicarbazone, thiosemicarbazide, thiocarbazone, disulfide, hemiacetal, thiohemiacetal, α-keto-alkylthioalkyl or α-keto-alkylaminoalkyl; or (ii) $X_1$ and $X_2$, independently, are O or NH; and $L_1$—Y—$L_2$ together are NH—$L_3$—NH or NH—NH—$L_3$—NH—NH; and $L_3$ is $C_1$–$C_{20}$ straight chain alkyl, $C_1$–$C_{20}$ straight chain substituted alkyl, $C_2$–$C_{50}$ branched chain alkyl, $C_2$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne, $C_3$–$C_{50}$ branched chain alkyne, $C_3$–$C_{50}$ branched chain substituted alkyne, polyamine, polyamide, polyester, polyethylene glycol, polyether, aryl, aralkyl or heterocyclic; or (iii) $X_1$ and $X_2$, independently, are O, S, NH, $CH_2$ or CO;

$L_1$ and $L_2$, independently, are $C_1$–$C_{20}$ straight chain alkylamino, $C_1$–$C_{20}$ straight chain substituted alkylamino, $C_2$–$C_{50}$ branched chain alkylamino, $C_2$–$C_{50}$ branched chain substituted alkylamino, $C_2$–$C_{20}$ straight chain alkenylamino, $C_2$–$C_{20}$ straight chain substituted alkenylamino, $C_3$–$C_{50}$ branched chain alkenylamino, $C_3$–$C_{50}$ branched chain substituted alkenylamino, $C_2$–$C_{20}$ straight chain alkynylamino, $C_2$–$C_{20}$ straight chain substituted alkynylamino, $C_3$–$C_{50}$ branched chain alkynylamino, $C_3$–$C_{50}$ branched chain substituted alkynylamino, $C_2$–$C_{50}$ branched chain substituted alkynylamino, $C_1$–$C_{20}$ straight chain alkylthio, $C_1$–$C_{20}$ straight chain substituted alkylthio, $C_2$–$C_{50}$ branched chain alkylthio, $C_2$–$C_{50}$ branched chain substituted alkylthio, $C_2$–$C_{20}$ straight chain alkenylthio, $C_2$–$C_{20}$ straight chain substituted alkenylthio, $C_3$–$C_{50}$ branched chain alkenylthio, $C_3$–$C_{50}$ branched chain substituted alkenylthio, $C_2$–$C_{20}$ straight chain alkynylthio, $C_2$–$C_{20}$ straight chain substituted alkynylthio, $C_3$–$C_{50}$ branched chain alkynylthio or $C_3$–$C_{50}$ branched chain substituted alkynylthio; and Y is a heterobifunctional or homobifunctional cross-linking reagent;

where said substituent of said substituted alkyl, substituted alkenyl and substituted alkyne moieties is an intercalator, a conjugate, polyamine, polyamide, polyethylene glycol, a group that enhances the pharmacodynamic properties of oligonucleotides or a group that enhances the pharmacokinetic properties of oligonucleotides.

As illustrated in the examples below, the invention further includes methods for fixing a sequence-specific oligonucleotide in a set configuration. These methods include selecting a first site in the oligonucleotide. The first site is selected to have a first specific sequence of nucleotides. A first bond precursor is attached to a sugar moiety of one of the nucleotides of the first site. The first bond precursor is for forming a covalent bond. The methods include selecting a second site in the oligonucleotide. The second site is selected to have a second specific nucleotide sequence. A second bond precursor is attached to a sugar moiety of a nucleotide of the second site. The second bond precursor also is for forming a covalent bond. The methods further include forming a covalent cross-linkage between the first and the second bond precursors. The covalent cross-linkage is independent of the phosphate inter-nucleoside linkages that define the primary structure of the oligonucleotide. In certain embodiments, the methods further include attaching the first bond precursor to a sugar moiety of a nucleotide of the first site by reacting a precursor of the nucleotide with a suitable reagent, derivatizing the nucleotide precursor to a protected and activated form, and then synthetically incorporating the derivatized nucleotide precursor into the first nucleotide sequence. In still other embodiments, the methods further include attaching the second bond precursor to a sugar moiety of a nucleotide of the second site by reacting a precursor of the nucleotide with a suitable reagent, derivatizing the nucleotide precursor to a protected and activated form, and synthetically incorporating the derivatized precursor into the second nucleotide sequence.

The invention further includes methods for the intrastrand cross-linkage of an oligonucleotide. In certain embodiments, the methods include the steps of selecting a first nucleotide sequence and a second nucleotide sequence in the oligonucleotide, incorporating an abasic nucleotide within the first sequence, attaching a bond precursor to a nucleotide of the second sequence, and forming a covalent cross-linkage between the abasic site and the bond precursor.

In other embodiments, the methods include selecting a first nucleotide sequence and a second nucleotide sequence in the oligonucleotide, attaching a first bond precursor to a sugar moiety of a nucleotide of the first specific sequence, attaching a second bond precursor to a sugar moiety of a nucleotide of the second sequence, and forming covalent cross-linkage between the first and the second bond precursors. This covalent cross-linkage is independent of the phosphate internucleotide linkages that define the primary structure of the oligonucleotide. Preferably, the first nucleotide sequence is selected to be complementary to and hybridizable with the second nucleotide sequence.

The invention further includes methods for cross-linking first and second oligonucleotide strands including the steps of selecting a first nucleotide sequence in a first oligonucleotide strand, selecting a second nucleotide sequence in a second oligonucleotide strand, incorporating an abasic nucleotide within the first nucleotide sequence, attaching a bond precursor to a nucleotide of the second sequence, and forming a covalent cross-linkage between the abasic site and the bond precursor. These methods can further include selecting the first nucleotide sequence to be complementary to and hybridizable with the second nucleotide sequence, attaching the bond precursor at a 2'-position of a nucleotide of the second sequence, and forming an aldehydic functional group at the abasic site. The bond precursor should be capable of forming an oxime, imine, hydrazone, semicarbazone, thiosemicarbazone, hydrazide-hydrazone, hemiacetal or thiohemiacetal linking group with the abasic site aldehydic functional group.

The invention further includes methods for cross-linking first and second oligonucleotide strands including the steps of selecting a first nucleotide sequence in a first oligonucleotide strand, selecting a second nucleotide sequence in a second oligonucleotide strand, attaching a first bond precursor to a sugar moiety of a nucleotide of the first sequence, attaching a bond precursor on a sugar moiety of a nucleotide of the second sequence, and forming a covalent cross-linkage between the first and the second bond precursors. This covalent cross-linkage is independent of the phosphate inter-nucleotide linkages that define oligonucleotide primary structure.

The following examples are illustrative of the invention. It is understood that this invention is not limited by these illustrative examples but solely by the claims appended hereto.

EXAMPLE 1

Standard Oligonucleotide Synthesis

Oligonucleotide syntheses were performed on an Applied Biosystems 380 B or 394 DNA synthesizer following standard phosphoramidite protocols and cycles using reagents supplied by the manufacture. When modified phosphoramidites are used, a longer coupling time (10–15 min) was employed. The oligonucleotides were normally synthesized in either a 10 µmol scale or a 3×1 µmol scale in the "Trityl—On" mode. Standard deprotection conditions (30% $NH_4OH$, 55° C., 16 hr) were employed. HPLC was performed on a Waters 600E instrument equipped with a model 991 detector. For analytical chromatography, the following reverse phase HPLC conditions were employed: Hamilton PRP-1 column (15×2.5 cm); solvent A: 50 mm TEAA, pH 7.0; solvent B: 45 mm TEAA with 80% $CH_3CN$; flow rate: 1.5 ml/min; gradient: 5% B for the first 5 minutes, linear (1%) increase in B every minute thereafter. For preparative purposes, the following reverse phase HPLC conditions were employed: Waters Delta Pak Waters Delta-Pak $C_4$ 15 µm, 300A, 25×100 mm column equipped with a guard column of the same material; column flow rate: 5 ml/min; gradient: 5% B for the first 10 minutes, linear 1% increase for every minute thereafter. Following HPLC purification, oligonucleotides are detritylated and further purified by size exclusion using a Sephadex G-25 column. All oligonucleotide sequences are listed in a standard 5' to 3' order from left to right.

EXAMPLE 2

Preparation Of Activated and Protected Nucleotides Having A Space-spanning Group And Active Functional Group A. Preparation of 5'-Dimethoxytrityl-2'-O-(Functionalized Space-spanning Group)Nucleoside Phosphoramidites i. 5'-Dimethoxytrityl-2'-O-(Pentyl-N-phthalimido)-N6-Benzyladenosine Phosphoramidite 5'-Dimethoxytrityl-2'-O-(pentyl-N-phthalimido)-N6-benzyladenosine phosphoramidite was synthesized as per the procedures of U.S. patent application Nos. US91/00243 and 463,358, herein incorporated by reference, starting from adenosine. Briefly, this procedure treats adenosine with NaH in DMF followed by treatment with N-(5-bromopentyl)phthalimide (Transworld Chemical Co. Inc., Rockville, Md.). Further treatment with $(CH_3)_3SiCl$, Ph—C(O)—Cl and $NH_4OH$ yielded N6-benzyl protected 2'-pentyl—N-phthalimido functionalized adenosine. Treatment with DIPA and $CH_2Cl_2$ added a DMT blocking group at the 5'-position. Finally phosphitylation gave the desired phosphoramidite compound.

ii. 5'-Dimethoxytrityl-2'-O-( 2-Methyloctyl-N-phthalimido)-N4-Benzylcytidine Phosphoramidite a. N-(8-bromo-2-methyloctyl)phthalimide 8-Bromo-2-methylaminooctane is treated with phthalic anhydride in toluene in the presence of triethylamine under reflux. The solvent is removed in vacuo. The residue, when triturated with water, acidified with hydrochloric acid and crystallized from alcohol will yield N-(8-bromo-2-methyloctyl)phthalimide.

b. Preparation of 5'-Dimethoxytrityl-2'-O-( 2-Methyloctyl-N-Phthalimido)-N4-Benzylcytidine Phosphoramidite Cytidine, when treated with NaH and N-(8-Bromo-2-methyloctyl)phthalimide followed by treatment with DIPA and $CH_2Cl_2$ and phosphitylation utilizing the procedure of Example 2-A-i, will give 5'-dimethoxytrityl-2'-O-( 2-methyloctyl-N-phthalimido)-N4-benzylcytidine phosphoramidite.

c. 5'-Dimethoxytrityl-2'-O-(Eicosyl-N-Phthalimido)Adenosine Phosphoramidite

N-(20-bromoeicosyl)phthalimide is prepared as per the procedure of Example 2-A-ii-a from 1-amino-20-bromoeicosane. Adenosine is treated with NaH in DMF and 1-amino-20bromoeicosane, benzylated, treated with DIPA and $CH_2Cl_2$ and phosphitylation as per the procedure of Example 2-A-ii will yield the title compound.

iii. 5'-Dimethoxytrityl-2'-O-(Eicosyl-N-Phthalimido)Uridine Phosphoramidite

N-(20-bromoeicosyl)phthalimide is prepared as per the procedure of Example 2-A-ii-a from 1-amino-20-bromoeicosane. Uridine is treated as per the procedure of Akiyama, et al., *NOTES Bull. Chem. Soc. Jpn.*, 1990, 63, 3356, to give 3-(4-methoxyphenylmethyl)-3',5'-O-(tetraisopropyldisiloxane-1,3-diyl)uridine. Briefly this treatment first blocks the 3' and 5' sugar hydroxyls of uridine followed by blocking the N3 imide group of the pyrimidine heterocycle with a p-methoxybenzyl group. Treatment of the blocked uridine with $Ag_2O$ and N-(20-bromoeicosyl)phthalimide will yield a 2'-alkylated blocked intermediate compound. The tetraisopropyldisiloxane blocking group is removed by taking the uridine intermediate up in $C-H_3CN$ and treating with 60% HF. The p-methoxyphenylmethyl blocking group is removed by treatment with $AlCl_3$ in anisole under a $N_2$ atmosphere followed by Hcl. Both of these procedures are conducted as per the above procedure of Akiyama et al. Further treatment as per the procedure of Example 2-A-ii with DIPA and $CH_2Cl_2$ to add a DMT blocking group at the 5'-position followed by phosphitylation will yield the title compound.

iv. 5'-Dimethoxytrityl-2'-O-( 2-Amylenyl-N-phthalimido)-N2-Isobutyrylguanosine-Phosphoramidite N-(5-bromo-2-amylenyl)phthalimide is prepared as per the procedure of Example 2-A-ii-a from 1-amino-5-bromoamyl-2-ene. 3', 5'-O-(Tetraisopropyldisiloxane-1,3-diyl)-2-chloro-6-( 2,6-dichlorophenoxy)purine riboside is prepared as described by Sproat, *Nucleic Acid Res.*, 1990, 18, 41. Treatment of the latter compound with the first followed by deblocking and enzymatic deaminization with adenosine deaminase utilizing the procedure of Sproat, *Nucleic Acids Research*, 1991, 19, 733, will yield the desired 2'-alkylated guanosine intermediate. Further treatment of this alkylated guanosine intermediate as per the procedure of Example 2-A-i with $(CH_3)_3SiCl$, isobutyryl chloride and $NH_4OH$ yields N2-isobutyryl protected 2'-amylenyl-N-phthalimido functionalized guanosine. Treatment with DIPA and $CH_2Cl_2$ to add a DMT blocking group at the 5'-position followed by phosphitylation will give the desired phosphoramidite compound.

v. 5'-Dimethoxytrityl-2'-O-(Ethyl-N-Phthalimido)Thymidine Phosphoramidite

Thymidine is blocked and treated with $Ag_2O$ and N-(2-bromoethyl)phthalimide (Aldrich Chemical Co., Inc., Milwaukee, Wis.) as per the procedure of Example 2-A-iii followed by further treatment as per the procedure of Example 2-A-i with DIPA and $CH_2Cl_2$ to add a DMT blocking group at the 5'-position and finally phosphitylation will yield the title compound.

vi. Preparation of Other 5'-Dimethoxytrityl- 2'-O-(Phthalimido Blocked Amine Functionalized Space-spanning Group)-Nucleoside Phosphoramidites a. Preparation of N-($\Omega$-bromoalkyl, $\Omega$-bromoalkenyl and $\Omega$-bromoalkynyl)phthalimides In the manner of Example 2-A-ii-a the following $\Omega$-bromo phthalimide blocked amine compounds, useable as amine functionalized space-spanning groups, can be prepared:

N-(7-bromoheptyl)phthalimide ;N-(8-bromooctyl)phthalimide; N-(9-bromononyl)phthalimide; N- (10-bromododecyl) phthalimide; N-(11-bromoundecyl)phthalimide; N-(12bromodocecyl) phthalimide; N-(13-bromotridecyl) phthalimide; N-( 14-bromotetradecyl)phthalimide; N-(15-bromopentadecyl)-phthalimide; N-(16-bromohexadecyl)phthalimide; N-(17-bromoheptadecyl) phthalimide; N-(18-bromooctadecyl)phthalimide; N-(19-bromononadecyl)phthalimide; N-(3-bromo-2-methylpropyl) phthalimide; N-(4-bromo-2-methyl-3-ethylbutyl) phthalimide; N-(3-bromo-2,2-diethylpropyl)phthalimide; N-( 4-bromo-3-propylbutyl)phthalimide; N-(10-bromo-2,8-dibutyldecyl) phthalimide; N-(8-bromo-6,6-dimethyloctyl) phthalimide; N-( 8-bromo-6-propyl-6-butyloctyl) phthalimide; N-(4-bromo-2-methylbutyl) phthalimide; N-(5-bromo-2-methylpentyl)phthalimide; N-(5-bromo-3-methylpentyl)phthalimide; N-(6-bromo-2-ethylhexyl) phthalimide; N-(5-bromo-3-penten-2-one)phthalimide; N-( 4-bromo-3-methyl-2-butanol)phthalimide; N-(8-bromo-3-amino-2cyanooctyl)phthalimide; N-(7-bromo-3-methoxy-4-heptanal) phthalimide; N-(4-bromo-2-iodo-3-nitrobutyl)-phthalimide; N-(12-bromo-4-isopropoxydodecyl)phthalimide; N-( 10-bromo-4-azido-2-nitrodecyl)phthalimide; N-(9-bromo-5-mercaptononyl)phthalimide; N-(5-bromo-4aminopentenyl) phthalimide; N-(5-bromo-penten-2-yl)phthalimide; N-(3-bromoallyl)phthalimide; N-(4-bromocrotyl)phthalimide; N-( 3-bromopropargyl)phthalimide; N-(1-bromonaphth-4-yl) phthalimide; N- (2-bromoanthrac-7-yl) phthalimide; and N-( 2-bromophenanthr-6-yl)phthalimide.

b. Preparation of 5'-Dimethoxytrityl- 2'-O-(N-Phthalimide Functionalized Space-spanning Group) Nucleoside Phosphoramidites In the manner of Examples 2-A-i, 2-A-ii-b, 2-A-iii, 2-A-iv and 2-A-v, the following 5'-dimethoxytrityl-2'-O-(space-spanning group-N-phthalimide)nucleoside phosphoramidite can be prepared:

5'-dimethoxytrityl-2'-O-(dodecyl-N-phthalimido)-N4-benzylcytidine phosphoramidite; 5'-dimethoxytrityl- 2'-O-(tetra-decyl-N-phthalimido)-N6-benzyladenosine phosphoramidite; 5'-dimethoxytrityl-2'-O-(2-methylpropyl-N-phthalimido)uridine phosphoramidite; 5'-dimethoxytrityl-2'-O-( 2,8-dibutyldecyl-N-phthalimido)-N2-isobutyrylguanosine phosphoramidite; 5'-dimethoxytrityl-2'-O-(3-methylpentyl-N-phthalimido)thymidine phosphoramidite; 5'-dimethoxytrityl-2'-O-( 2-cyanooctyl-N-phthalimido)-N4-benzylcytidine phosphoramidite; 5'-dimethoxy-trityl- 2'-O-(3-methoxy-4-heptanal-N-phthalimido)uridine phosphoramidite; 5'-dimethoxytrityl-2'-O-( 3-nitrobutyl-N-phthalimido)-N6-adenosine phosphoramidite; 5'-dimethoxytrityl- 2'-O-(propargyl-N-phthalimido)-N2-isobutyrylguanosine phosphoramidite; and 5'-dimethoxytrityl-2'-O-(3-anthrac-7-yl-N-phthalimido)thymidine phosphoramidite.

B. Preparation of 5'-Dimethoxytrityl-2'-S-(Amine Functionalized Space-spanning Group)-2'-Deoxy-Nucleoside Phosphoramidites i. Preparation of N-(1-Bromo-8-dodecyl)Phthalimide 1-Aminododecyl-12-ol is treated with N-ethoxycarbonylphthalimide utilizing the reaction conditions of McArthur, et. al., *Synth. Commun.*, 1983, 13, 311, to yield N-(dodecyl-12-ol)phthalimide which in turn when treated with phosphorous tribromide and pyridine utilizing the reaction conditions of Hall, et al., *Synthetic Procedures in Nucleic Acid Chemistry*, Zorbach and Tipson, Editors, Volume 1, John Wiley & Sons, 1968 will yield N-(12-bromododecyl)phthalimide.

ii. 5'-Dimethoxytrityl-2'-S-(Dodec-12-N-Phthal-imido)- 2'-Deoxyuridine Phosphoramidite 2'-Deoxy-2-thiouridine is prepared as per the procedure of Divakar, *J. Chem. Soc. Perkin Trans.*, 1990, 1, 969. 2'-Deoxy-2-thiouridine when treated with NaH in DMF followed by treatment with N-(12-bromododecyl)phthalimide will yield 2'-S-(dodecyl-N-phthalimido) functionalized uridine. Treatment with DIPA and $CH_2Cl_2$ to add a DMT blocking group at the 5'-position followed by phosphitylation will give the desired phosphoramidite compound.

C. Preparation of 5'-Dimethoxytrityl-2'-NH-(Alkyl-N-Phthalimido)- 2'-Deoxy-Nucleoside Phosphoramidites i. N-(Butyl-4-al)Phthalimide (an Ω-aldehydic terminating α-N-Phthalimide functionalized space-spanning group)

4-Aminobutyraldehyde diethyl acetal (Aldrich Chemical Co., Inc., Milwaukee, Wis.) when treated with phthalic anhydride in toluene in the presence of triethylamine as per the procedure of Example 2-A-ii-a will give an N-phthalimide blocked amine group at the 1-position of the butyl group and an diethyl acetal blocked aldehyde group at the 4-position. The diethyl acetal blocking group is then removed by acid catalyzed hydrolysis to give N-(butyl-4-al)phthalimide.

ii. 5'-Dimethoxytrityl-2'-NH-(Butyl-N-Phthal-imido)- 2'-Deoxy-N6-Benzyladenosine Phosphoramidite 2'-Amino-N6-benzyl-2'-deoxyadenosine, prepare as per the procedure of G. Burke, et. al., *J. Carbohydrates, Nucleosides, Nucleotides*, 1988, 7, 63, and N-(butyl-4-al) phthalimide are stirred in dry $CH_2Cl_2$. The solvent is removed and the residue taken up in NaOAc buffer (pH 5.02) and treated with $NaCNBH_3$ to reduce the intermediate imine to the desired amine linking functionality. Further treatment as per the procedure of Example 2-A-i with DIPA and $CH_2Cl_2$ to add a DMT blocking group at the 5'-position followed by phosphitylation will yield the title compound.

D. Preparation of 5'-Dimethoxytrityl-2'-(Alkyl-N-Phthalimido)- 2'-Deoxy-Nucleoside Phosphoramidites Introduction of a 2' directly alkylated nucleotide (i.e. a methylene linking group joining a space-spanning group to the 2'-position of a nucleotide sugar moiety) into an oligonucleotide is accomplished by free radical alkylation of the corresponding nucleoside followed by conversion to the appropriate 5'-dimethoxytrityl phosphoramidite nucleotides.

i. 5'-Dimethoxytrityl-2'-(Allyl-N-Phthalimido)- 2'-Deoxy-N6-Benzyladenosine Phosphoramidite 2'-O-(Phenoxythioxomethyl)-2'-deoxyadenosine will be treated with N-(5-bromopenten-2-yl)phthalimide (from Example 2-A-vi) and tributyltin hydride utilizing conditions analogous to those described in Flandor, et al., *Tetrahedron Letters*, 1990, 31, 597, to effect a free radical alkylation at the 2'-position of the nucleoside. The resulting alkylated compound is then further treated with $(CH_3)_3SiCl$, Ph-C(O)-Cl and $NH_4OH$ to give the N6-benzyl protected 2'-[N-(penten-2-yl)phthalimido] functionalized adenosine. This is then followed by treatment with DIPA and $CH_2Cl_2$ to add a DMT blocking group at the 5'-position which in turn is followed by phosphitylation, all as per the procedure of Example 2-A-i, to give the desired phosphoramidite compound.

ii. 5'-Dimethoxytrityl-2'-(Allyl-N-Phthalimido)- 2'-Deoxyuridine Phosphoramidite 2'-O-(Phenoxythioxomethyl)-2'-deoxyuridine will be treated with N-(5-bromopenten-2-yl)phthalimide (from Example 2-A-vi) and tributyltin hydride utilizing conditions analogous to those described in Flandor, et al., *Tetrahedron Letters*, 1990, 31, 597 to effect a free radical alkylation at the 2'-position of the nucleoside. The resulting alkylated compound is then further treated with DIPA and $CH_2Cl_2$ to add a DMT blocking group at the 5'-position which in turn is followed by phosphitylation, all as per the procedure of Example 2-A-iii, to give the desired phosphoramidite compound.

E. Preparation of 5'-Dimethoxytrityl-2'-O-(Hydrazine Functionalized Space-spanning Group)Nucleoside Phosphoramidites i. 8-Bromooctylbenzylcarbazide (an α-bromo carbazide protected Ω-hydrazine functionalized space-spanning group)

8-Bromooctanol is tosylated with tosyl chloride in pyridine. The solvent is removed and the 8-bromooctanol O-tosylate is treated with benzylcarbazide and activated molecular sieves in anhydrous dimethylacetamide overnight at 110° C. The solvent is removed.and the residue purified by silica gel chromatography to yield bromooct-8-ylbenzylcarbazide.

ii. 5'-Dimethoxytrityl-2'-O-(Oct-8-ylbenzylcarbazide)uridine Phosphoramidite

Uridine will be treated with 8-bromooctylbenzylcarbazide utilizing the method of Example 2-A-iii to give the title compound.

iii. 5'-Dimethoxytrityl-2'-O-(Oct- 8-ylbenzylcarbazide)-N4-Benzylcytidine Phosphoramidite Cytidine will be treated with 8-bromooctylbenzylcarbazide utilizing the method of Example 2-A-ii-b to give the title compound.

iv. 5'-Dimethoxytrityl-2'-O-(Oct- 8-ylbenzylcarb-azide)-N2-Isobutyrylguanosine Phosphoramidite Guanosine will be treated with 8-bromooctylbenzylcarbazide utilizing the method of Example 2-A-iv to give the title compound.

v. 5'-Dimethoxytrityl-2'-O-(Oct- 8-ylbenzylcarb-azide)-N6-Benzyladenosine Phosphoramidite Adenosine will be treated with 8-bromooctylbenzylcarbazide utilizing the method of Example 2-A-i to give the title compound.

F. Preparation of 5'-Dimethoxytrityl-2'-O-(Hydroxylamine-Functionalized Space-spanning Group)Nucleoside Phosphoramidires i. O-(8-Bromooctanol)phthalimide (an α-bromo O-phthalimide protected Ω-hydroxylamine functionalized space-spanning group)

1,8-Octanediol is treated with one equivalent of dihydropyrane in the presence of acid to give the 8-(tetrahydropyran-2-yl)octanol. 8-(Tetrahydropyran-2-yl)octanol, N-hydroxyphthalimide and triphenylphosphine in DMF are treated at 0° C. with diisopropylazodicarboxylate utilizing Mitsunobu reaction conditions to give O-[8-(tetrahydropyran-2-yl)octanol)phthalimide. Acid treatment of O-[8-(tetrahydro-pyran- 2-yl)octanol]phthalimide will yield O-(octanol)phthalimide which in turn when treated with phosphorous tribromide and pyridine utilizing the reaction conditions of Hall, et al., *Synthetic Procedures in Nucleic Acid Chemistry*, Zorbach and Tipson, Editors, Volume 1, John Wiley & Sons, 1968 will yield O-(8-bromooctanol)phthalimide.

ii. 5'-Dimethoxytrityl-2'-O-(Octan-8-ol-O-Phthalimido)-N4-Benzylcytidine Phosphoramidite Cytidine is treated with NaH in DMF followed by treatment with O-(8-bromooctanol)phthalimide from Example 2-F-i. Further treatment with $(CH_3)_3SiCl$, Ph—C(O)—Cl and $NH_4OH$ will yield N4-benzyl protected 2'-octyl-O-phthalimido functionalized cytidine. Treatment with DIPA and $CH_2Cl_2$ will add a DMT blocking group at the 5'-position. Finally phosphitylation as per the procedure of Example 2-A-ii will give the desired phosphoramidite compound.

iii. 5'-Dimethoxytrityl-2'-O-(Octan-8-ol-O-Phthalimide)uridine Phosphoramidite

Uridine is blocked and then treated with $Ag_2O$ and O-(8-bromooctanol)phthalimide from Example 2-F-i. Treatment with DIPA and $CH_2Cl_2$ will add a DMT blocking group at the 5'-position. Finally phosphitylation as per the procedure of Example 2-A-iii will give the desired phosphoramidite compound.

G. Preparation of 5'-Dimethoxytrityl-2'-O-(Semicarbazide Functionalized Space-spanning Group) Nucleoside Phosphoramidites i. 5'-Dimethoxytrityl-2'-O-(pent-5-ylsemicarbazide)uridine Phosphoramidite Uridine is blocked and then treated with $Ag_2O$ and N-(8-bromopenyl)semicarbazide utilizing the method of Example 2-A-iii to give the title compound.

ii. 5'-Dimethoxytrityl-2'-O-(pent- 5-ylsemicar-bazide)-N6-Benzyladenosine Phosphoramidite Adenosine will be treated with N-(8-bromopenyl)semicarbazide utilizing the method of Example 2-A-i to give the title compound.

H. Preparation of 5'-Dimethoxytrityl-2'-O-(Hydrazide Functionalized Space-spanning Group) Nucleoside Phosphoramidites i. α-Cloroethoxycarbonylethane Chloroacetyl chloride (Air Products, Emmaus, Pa.) is added drop wise to stirring ethanol to esterify the acid chloride. The ester is then recovered by distillation.

ii. 5'-Dimethoxytrityl-2'-O-(ethoxycarbonylethyl)uridine Phosphoramidite

Uridine is blocked and then treated with $Ag_2O$ and α-cloroethoxycarbonylethane as per the procedure of Example 2-A-iii to yield the title compound.

iii. 5'-Dimethoxytrityl-2'-O-(eth-2-ylhydrazide)uridine Phosphoramidite

5'-Dimethoxytrityl-2'-O-(ethoxycarbonylethyl)uridine phosphoramidite will be treated with hydrazine to give the corresponding 2'-O-(ethylhydrazide)uridine title compound.

I. Preparation of 5'-Dimethoxytrityl-2'-O-(Alcohol Functionalized Space-spanning Group) Nucleoside Phosphoramidites i. 1-O-(Tetrahydropyran-2-yl)-7-bromoheptanol 7-Bromoheptanol will be treated with dihydropyrane in the presence of acid to give 1-O-(tetrahydropyran-2-yl)-7-bromoheptanol.

ii. 5'-Dimethoxytrityl-2'-O-[O-(Tetrahydropyran- 2-yl)heptan-7-ol)]-N4-Benzylcytidine Phosphoramidite Cytidine will be treated with 1-O-(tetrahydropyran- 2-yl)-7-bromoheptanol as per the procedure of Example 2-A-ii to give the title compound.

iii. 5'-Dimethoxytrityl-2'-O-[O-(Tetrahydro-pyran- 2-yl)heptan-7-ol)]uridine Phosphoramidite Uridine is blocked and then treated with $Ag_2O$ and 1-O-(tetrahydropyran- 2-yl)-8-bromoheptanol as per the procedure of Example 2-A-iii to give the title compound.

J. Preparation of 5'-Dimethoxytrityl-2'-O or 2'-S (Thiol Functionalized Space-spanning Group)-Nucleoside Phosphoramidites i. Via Ring Opening of 2,2'-Arthydro Pyrimidines a. 2'-S-(Octan-8-Thiol)thymidine 2,2'-Anhydro thymidine will be ring opened with octane-1,8-dithiol to give 2'-S-(octan-8-thiol)thymidine.

b. 5'-Dimethoxytrityl-2'-S-[S-Trityl-(Octan- 8-thiol)]-2'-Deoxy-Thymidine Phosphoramidite 2'-S-(octan-8-thiol)thymidine when treated with trityl chloride will give 2'-S-[S-trityl(octan-8-thiol)]thymidine which will then be further treated with DIPA and $CH_2Cl_2$ to add a DMT blocking group at the 5'-position and finally phosphitylation as per Example 2-A-v to give the title compound.

ii. Via O-Alkylation a. 1-S-Trityl-8-Bromohexanethiol

8-Bromohexanethiol will be tritylated with trityl chloride to give 1-S-trityl-8-bromohexanethiol.

b. 5'-Dimethoxytrityl-2'-O-[S-Trityl-(Hexan- 8-thiol)]-N6-Benzyladenosine Phosphoramidite Adenosine is treated with NaH in DMF as per example 2-A-i. The reaction product will then be treated with 1-S-trityl-8-bromohexanethiol followed by treatment with $(CH_3)_3SiCl$, Ph—C(O)—Cl and $NH_4OH$ to yield the N6-benzyl protected 2'-O-[S-trityl(hexyl-8-thiol)] functionalized adenosine. Treatment with DIPA and $CH_2Cl_2$ to add a DMT blocking group at the 5'-position followed by phosphitylation, further as per the procedure of Example 2-A-i, will give the title compound.

c. 5'-Dimethoxytrityl-2'-O-[S-Trityl-(Hexan- 8-thiol)] uridine Phosphoramidite

Uridine is blocked and then treated with $Ag_2O$ and 1-S-trityl-8-bromohexanethiol as per Example 2-A-iii. The reaction product will then be treated with followed by treatment with DIPA and $CH_2Cl_2$ to add a DMT blocking group at the 5'-position and finally phosphitylation, further as per the procedure of Example 2-A-iii, to give the title compound.

d. 1-S-Trityl-8-Bromopentanethiol

8-Bromopentanethiol will be tritylated with trityl chloride to give 1-S-trityl-8-bromopentanethiol.

e. 5'-Dimethoxytrityl-2'-O-[S-Trityl-(Pentan- 8-thiol)] uridine Phosphoramidite

Uridine is blocked and then treated with $Ag_2O$ and 1-S-trityl-8-bromopentanethiol as per Example 2-A-iii followed by treatment with DIPA and $CH_2Cl_2$ to add a DMT blocking group at the 5'-position and finally phosphitylation, further as per the procedure of Example 2-A-iii, to give the title compound.

K. Preparation of 5'-Dimethoxytrityl-2'-O-(Protected Aldehyde Functionalized Space-spanning Group)Nucleoside Phosphoramidites i. Preparation of Acetal Functionalization a. N6-Benzyl-5'-Dimethoxytrityl- 2'-O[Propion-3-al Bis(o-Nitrobenzyl Acetal)adenosine Phosphoramidire Adenosine is treated with NaH and 3-bromopropionaldehyde bis(o-nitrobenzyl) acetal as per the procedure of Example 2-A-i. Further treatment with $(CH_3)_3SiCl$, Ph—C(O)—Cl and $NH_4OH$ to add a benzyl blocking group followed by DIPA and $CH_2Cl_2$ to add a DMT blocking group at the 5'-position and further followed by phosphitylation as per the procedure of Example 2-A-i, will give the desired compound.

b. 5'-Dimethoxytrityl-2'-O-[Propion-3-al Bis(o-Nitrobenzyl Acetal)uridine Phosphoramidite Uridine is blocked followed by treatment with $Ag_2O$ and 3-bromopropionaldehyde bis(o-nitrobenzyl) acetal as per the procedure of Example 2-A-iii. Further treatment with DIPA and $CH_2Cl_2$ to add a DMT blocking group at the 5'-position and further followed by phosphitylation as per the procedure of Example 2-A-i, will give the desired compound.

ii 6-(Diphenylimidazolidino)hexyl Bromide

6-Bromohexionyl acid chloride will be treated with ethylmercaptan. The resulting ethyl thiol-6-bromohexionate is then desulfurized with Raney nickel giving 6-bromohexenal. The 6-bromohexenal is then treated with 1,2-dianilinoethylene in benzene/DMSO to give the title 6-(diphenylimidazolidino)hexyl bromide.

iii. 5'-Dimethoxytrityl-2'-O-[6-(diphenylimidazolidino) hexyl]-N2-Isobutyrylguanosine Phosphoramidite 3', 5'-O-(Tetraisopropyldisiloxane-1,3-diyl)-2-chloro-6-(2,6-dichlorophenoxy)purine riboside is reacted with 6-(diphenylimidazolidino)hexyl bromide as per Example 2-A-iv. Further treatment with $(CH_3)_3SiCl$, isobutyryl chloride and $NH_4OH$ will yield N2-isobutyryl protected 2'-(diphenylimidazolidino)hexyl functionalized guanosine. Treatment with DIPA and $CH_2Cl_2$ to add a DMT blocking group at the 5'-position followed by phosphitylation, further as per the procedure of Example 2-A-iv, will give the title compound.

iv. 5'-Dimethoxytrityl-2'-O-[6-(diphenylimidazolidino) hexyl]-N 6-Benzyladenosine Phosphoramidite Adenosine is treated with NaH/DMF followed by treatment with 6-(diphenylimidazolidino)hexyl bromide as per Example 2-A-i. Further treatment with $(CH_3)_3SiCl$, benzyl chloride and $NH_4OH$ will yield N6-benzyl protected 2'-(diphenylimidazolidino)hexyl functionalized adenosine. Treatment with DIPA and $CH_2Cl_2$ to add a DMT blocking group at the 5'-position followed by phosphitylation, further as per the procedure of Example 2-A-i, will give the title compound.

v. 5'-Dimetroxytrityl-2'-O-[6-(diphenylimidazol-idino) hexyl)-N 4-Benzylcytidine Phosphoramidite Cytidine is treated with NaH/DMF followed by treatment with 6-(diphenylimidazolidino)hexyl bromide as per Example 2-A-ii. Further treatment with $(CH_3)_3SiCl$, benzyl chloride and $NH_4OH$ will yield N4-benzyl protected 2'-(diphenylimidazolidino)hexyl functionalized cytidine. Treatment with DIPA and $CH_2Cl_2$ to add a DMT blocking-group at the 5'-position followed by phosphitylation, further as per the procedure of Example 2-A-ii, will give the title compound.

vi. 5'-Dimethoxytrityl-2'-O-[6-(diphenylimidazolidino) hexyl]uridine Phosphoramidite Uridine is blocked and then treated with $Ag_2O$ and 6-(diphenylimidazolidino)hexyl bromide as per Example 2-A-iii. Treatment with DIPA and $CH_2Cl_2$ to add a DMT blocking group at the 5'-position followed by phosphitylation, further as per the procedure of Example 2-A-ii, will give the titled compound.

EXAMPLE 3

Oligonucleotides Having 2'-Protected-Amine Terminating Linking Group

A. Preparation of 5'-Dimethoxytrityl-2'-(O-pentyl-N-phthalimido)- 2'-Deoxyadenosine Phosphoramidite.

To introduce a functionalization at the 2'-position of nucleotides within desired oligonucleotide sequences, 5'-dimethoxytrityl-2'-(O-pentyl-N-phthalimido)-2'-deoxyadenosine phosphoramidite was utilized. This compound provided the linking group attached to the 2' position of G nucleotide component of an oligonucleotide. The compound was synthesized generally in accordance with the procedures of patent application serial number PCT/US91/00243, starting from adenosine. In accordance with this procedure adenosine was treated with NaH in dimethylformamide (DMF) followed by treatment with N-(5-bromopentyl)phthalimide. Further treatment with $(CH_3)_3SiCl$, Ph—C(O)—Cl and $NH_4OH$ gave N6-benzyl protected 2'-pentyl-N-phthalimido functionalized adenosine. Treatment with DIPA and $CH_2Cl_2$ added a DMT blocking group at the 5'-position. Finally phosphitylation gave the corresponding phosphoramidite analogue. The phosphoramidite compound was utilized in the DNA synthesizer as a 0.09M solution in anhydrous $CH_3CN$. Oligonucleotide synthesis was carried out in either an ABI 390B or an ABI 394 synthesizer employing the standard synthesis cycles with an extended coupling time of 10 minutes during the coupling of the phosphoroamidite compound into the oligonucleotide sequence. Coupling efficiency of greater than 98% was observed.

EXAMPLE 4

N,N-Dibenzoyl-2'-O-(N-phthalimido-hexylamino) adenosine

A solution of adenosine (21.4 g, 80 mmole) in anhydrous DMF (400 ml) was cooled in an ice bath under an atmosphere of argon. To this mixture was added sodium hydride (3.52 g, 88 mmole). The reaction mixture was stirred for 30 minutes at ice bath temperature and an additional 8 hours at room temperature. To this solution, (27.3 g, 88 mmole) of N-phthalyl-hexanyl bromide in toluene (100 ml) was added dropwise and the reaction mixture was stirred for 16 hrs. The reaction mixture was evaporated to an oily residue under reduced pressure. Isopropyl alcohol is added to the residue and the resulting mixture is filtered and evaporated to a residue. Thin layer chromatography showed that the residue was pure enough for the next step. The residue was dissolved in anhydrous pyridine (25 ml) and coevaporated three times to remove moisture. To this dried residue in anhydrous pyridine (120 ml) was added 22 ml (18.8 g, 173.3 mmole) of trimethylsilyl chloride under an atmosphere of argon. The reaction was stirred at room temperature for 2 hrs and then benzoyl chloride (12.11 g, 86.1 mmole) was added. The reaction mixture was stirred at room temperature for another 16 hrs. The reaction mixture was evaporated to a residue and saturated $NaHCO_3$(aq)(200 ml)was added. The aqueous solution was extracted with ethyl acetate several times and the combined organic extracts was dried over anhydrous $Na_2SO_4$ and the solvent was evaporated under reduced pressure. The residue was purified by flash column chromatography over silica gel using methanol-dichloromethane as the eluent. The pure fractions were pooled together and evaporated to dryness to give 8.5 g (15%) of the title compound as a pale yellow foam. TLC: (Rf: 0.4; 5% MeOH/$CH_2Cl_2$); $^1H$ NMR: (DMSO-$d_6$) δ 1.5 (m, 8 H, $CH_2$), 3.5 (t, 2H, $CH_2$), 3.6 (m, 2H, H-5' & H-5"), 4.0 (m, 1H, H-4'), 4.1 (m, 1H, H-3'), 4.3 (m, 1H, H-2'), 4.5 (t, 1H, $CH_2$), 5.1 (t, 1H, 5'-OH), 5.3 (d, 1H, 3'-OH), 6.2 (d, 1H, H-1'), 7.5–7.8 (m, 14H, ArH & NPH), 8.7 (s, 1H, $H_2$), 8.9 (s, 1H, $H_8$).

EXAMPLE 5

5'-O-(4,4'-dimethoxytrityl)-N,N-dibenzoyl-
2'-O-(N-phthalimido-hexylamino)
adenosine-3'-O-[(2-cyanoethyl-N,N-
diisopropyl)]phosphoramidite The substrate Example 4 (6.35 g, 12 mmole) was dissolved in anhydrous pyridine (25 ml) and evaporated to dryness. This step was repeated three times to remove traces of moisture. The substrate was dissolved in anhydrous pyridine (25 ml) and 4,4'-dimethoxytrityl chloride (4.9 g, 14.4 mmole) was added under an atmosphere of argon. The reaction mixture was stirred for 16 hrs at room temperature. Methanol (50 ml) was added and the stirring was continued for 15 minutes. The reaction mixture was evaporated to a residue and 200 ml of saturated $NaHCO_3$(aq) was added. The aqueous solution was extracted three times with ethyl acetate. The organic extracts were combined and dried over anhydrous $Na_2SO_4$. The organic solution was filtered and evaporated under reduced pressure to give a yellow foam. Thin layer chromatography showed that the residue was pure enough for the next step. The foam was dissolved in 90 ml of dichloromethane under an atmosphere of argon. To this dichloromethane solution was added N,N-diisopropylamine tetrazolide (1.7 g, 6.2 mmole) and 2-cyanoethyl-N,N,N',N'-tetraisopropyl-phosphoramidite (6.6 ml, 22.3 mmole). The reaction mixture was stirred at room temperature for 16 hrs. The reaction mixture was poured onto 200 ml of saturated $NaHCO_3$(aq) and was stirred for 30 minutes. The $CH_2Cl_2$ layer was separated and the aqueous layer was extracted with $CH_2Cl_2$. The organic extracts were combined and dried over anhydrous $Na_2SO_4$. The dried solution was filtered and evaporated under reduced pressure. The resiude was purified by flash column chromatography over silica gel using ethyl acetate-hexane containing 1% TEA as the eluent. The main fractions were collected and evaporated to dryness to give 12.2 g (83.8%) of the title compound as a pale yellow foam. TLC: (Rf: 0.7; 50% EtOAc/Hexane/1% TEA); $^{31}$P NMR: ($CDCl_3$) δ 151.36 ppm & 150.51 ppm.

EXAMPLE 6

N,N-Dibenzoyl-2'-O-(N-phthalimido-decylamino)
adenosine

Adenosine (10.7 g, 40 mmole) is dissolved in anhydrous DMF (200 ml) and cooled in an ice bath under an atmosphere of argon. Sodium hydride (1.76 g, 44 mmole) was added and the reaction mixture was stirred for 30 minutes at ice bath temperature and an additional 8 hrs at room temperature. N-phthalamidodecyl bromide (17 g, 44 mmole) was added via a dropping funnel and the reaction mixture was stirred for 16 hours. The reaction mixture was evaporated to an oily residue and isopropyl alcohol (100 ml) was added. The mixture was filtered and the filtrate evaporated to an oily residue. The residue was coevaporated with pyridine (25 ml, X3) and dissolved in anhydrous pyridine (100 ml). To this solution was added trimethylsilyl chloride (16.2 g, 149.7 mmole). The reaction mixture was stirred at room temperature for 2 hrs and benzoyl chloride (9.7 g, 68.9 mmole) was added. The reaction mixture was stirred at room temperature for 16 hrs and evaporated to a residue. Saturated $NaHCO_3$ (aq) (200 ml) was added and the aqueous solution was extracted with ethyl acetate three times. The ethyl acetate extracts were combined and dried over anhydrous $Na_2SO_4$. The solution was filtered and evaporated to give a residue. The residue was purified by flash column chromatography over silica gel using methanol-dichloromethane as the eluent. The pure fractions were pooled together and evaporated to dryness to give 3.68 g (17.5%) of the title compound as a pale yellow foam. TLC: (Rf:0.4; 5% MeOH/$CH_2Cl_2$); $^1$H NMR: (DMSO-$d_6$) δ 1.5 (m, 18 H, $CH_2$), 3.5 (m, 2 H, $CH_2$), 3.6 (m, 2H, H-5' & H-5") , 4.0 (m, 1H, H-4'), 4.3 (m, 1H, H-3'), 4.5 (m, 1H, H-2'), 4.5 (t, 1H, $CH_2$), 5.1 (t, 1H, 5'-OH), 5.3 (d, 1H, 3'-OH), 6.1 (d, 1H, H-1'), 7.5 & 7.8 (m, 14H, ArH & NPH), 8.7 (s, 1H, H-2), 8.9 (s, 1H, H-8).

EXAMPLE 7

5'-O-(4,4'-dimethoxytrityl)-N,
N-dibenzoyl-2'-O-(N-phthalimido-decylamino)
adenosine-3'-O-[(2-cyanoethyl-N,N-
diisopropyl)]-phosphoramidite The substrate Example 6 (2.69 g, 3.54 mmole) was dissolved in anhydrous pyridine (8 ml) and evaporated to dryness. This step was repeated three times to remove moisture. To this well dried residue was added anhydrous pyridine (8 ml) followed by 4,4'-dimethoxytrityl chloride (1.45 g, 4.2 mmole) under an atmosphere of argon. The reaction mixture was stirred for 16 hrs at room temperature. Methanol (20 ml) was added and the stirring was continued for 15 minutes. The reaction mixture was evaporated to a residue and saturated $NaHCO_3$(aq) was added. The aqueous solution was then extracted with ethyl acetate three times. The combined organic extract was dried over anhydrous $Na_2SO_4$ and the solvent was removed under reduced pressure to give a yellow foam. Thin layer chromatography showed that the residue was pure enough for the next step. The foam was dissolved in anhydrous $CH_2Cl_2$ (26 ml) and N, N-diisopropylamine tetrazolide (0.51 g, 1.8 mmole) and 2-cyanoethyl-N,N,N',N'-tetraisopropyl-phosphoramidite (2.1 ml, 6.7 mmole) was added. The reaction mixture was stirred at room temperature for 16 hours and then poured onto saturated $NaHCO_3$(aq) (100 ml) and stirred for 30 minutes. The $CH_2Cl_2$ layer was separated and the aqueous layer was extracted with $CH_2Cl_2$. The $CH_2Cl_2$ extracts were combined with the separated $CH_2Cl_2$ phase and dried over anhydrous $Na_2SO_4$. The solution was filtered and the solvent was removed under reduced pressure. The residue was purified by flash column chromatography over silica gel using ethyl acetate-hexane containing 1% TEA as the eluent. The main fractions were collected and evaporated to-dryness to give 3.28 g (73.4%) of the title compound as a pale yellow foam. TLC: (Rf: 0.8; 50% EtOAc/Hexane/1% TEA); $^{31}$P NMR: ($CDCl_3$) δ 151.43 ppm & 150.54 ppm.

EXAMPLE 8

Preparation of Oligonucleotides Having an Abasic
Sites Located Thereon

A. Preparation of An Abasic Site Containing Oligonucleotide Via Enzymatic Reaction i. Oligonucleotide Containing Single Uridine Site An oligonucleotide of the sequence:

Oligomer 1 CGC AGU* CAG CC (SEQ ID NO: 1) wherein U* represents a 2'-deoxy uridine nucleotide, was prepared utilizing the procedure of Example 1. The deoxyuridine nucleotide in the middle of the sequence was added during the synthesis utilizing deoxyuridine phosphoramidite (Glen Research, Sterling, Va.). The oligonucleotide was prepared utilizing standard synthesis cycles. It was deprotected by normal deprotection utilizing ammonium hydroxide, 30%, for 16 hours. The solvent was evaporated, and the residue was purified by HPLC and detritylated. Final purification was effected on Sephadex G-25.

ii. Enzyme Stock Solution Preparation

Uracil-DNA glycosylase was isolated from *E. coli* M5219 cells transformed with the expression plasmid pBD396 containing the ung gene. The enzyme was purified to electrophoretic homogeneity as described by Lindahl, et al., *J. Biol. Chem.*, 1977, 252, 3286, and stored in 30 Mm HEPES-NaOH, pH 7.4, containing 5% glycerol, 2 mM DTT and 1 mM EDTA.

iii. Oligonucleotide Containing Single Abasic Site

An abasic oligonucleotide of the sequence:

Oligomer 2 CGC AGD* CAG CC (SEQ ID NO: 2)

wherein D* represents an abasic site, was prepared by treating 237 O.D. units of Oligomer 1 of Example 8-A-i in 0.5 ml water with 200 µl of the stock solution of Example 8-A-ii (200 micrograms of uracil DNA-glycosylase) and incubating at room temperature overnight. HPLC analysis showed quantitative removal of uracil as indicated by a 1:10 ratio between uracil and the abasic dodecamer oligonucleotide. The uracil retention time was 2.43 mins and the abasic oligonucleotide was 21.68 mins. The solution was lyophilized and stored in the freezer until further use.

iv. Oligonucleotide Containing Multiple Uridine Sites

In the manner of Example 8-A-i the following oligonucleotide was prepared:

Oligomer 3 GAC AGA GGU* AGG AGA AGU* GA (SEQ ID NO: 3)

wherein U* represents a 2'-deoxyuridine nucleotide. The oligonucleotide when treated as per the procedure of Example 8-A-iii will give an oligonucleotide of the sequence Oligomer 4 GAC AGA GGD* AGG AGA AGD* GA (SEQ ID NO: 4)

wherein D* represents an abasic site within the oligonucleotide.

B. Preparation of an Abasic Site Containing Oligonucleotide Via Abasic Sugar Precursor i. 5-O-4,4'-Dimethoxytrityl-1,2-Dideoxy-D-Ribofuranose- 3-O-(2-Cyanoethyl-N,N'-Diisopropyl) Phosphoramidite 5-O-4,4'-Dimethoxytrityl-1,2-dideoxy-D-ribofuranose-3-O-(2-cyanoethyl-N,N'-diisopropyl)-phosphoramidite is prepared as per the procedure of Iyer, et al., *Nucleic Acids Research*, 1990, 18, 2855, or as per the procedure of Didier Peoch et al., *Tetrahedron Letters*, 1991, 32, 207.

ii. Oligonucleotide Containing Abasic Site

Oligomer 2 of Example 8-A-iii, i.e. the oligonucleotide of the sequence:

Oligomer 2 CGC AGD* CAG CC wherein D* represents an abasic site, can also be prepared utilizing the synthetic procedures of the papers identified in Example 8-B-i. Utilizing those procedures, an o-Nitrobenzyldeoxyfuranose containing oligonucleotide is synthesized using the oligonucleotide synthetic methods of these papers. Photolysis, utilizing a high intensity Hg lamp, generates the corresponding abasic site containing oligonucleotide. Such abasic oligonucleotides are also described by Horn, et al., *Nucleosides & Nucleotides*, 1991, 10, 299.

EXAMPLE 9

Preparation of Oligonucleotides Incorporating 2'-O-(Amine Functionalized Space-spanning Group)

A. Single Site

An oligonucleotide of the sequence:

Oligomer 5 GGC TGA* CTG CG (SEQ ID NO: 5)

wherein A* indicates a 2'-O-(pentylamino)adenosine nucleotide was prepared as per the procedure of Example 1 utilizing an extend coupling time of 10 minutes during the coupling step of the modified nucleotide unit. 5'-Dimethoxytrityl-2'-O-(pentyl-N-phthalimido)-N 6-benzyladenosine phosphoramidite (from Example 2-A-i was utilized in the DNA synthesizer as a 0.09M solution in anhydrous CH₃CN. Oligonucleotide synthesis was carried out in either an ABI 390B or 394 synthesizer employing the standard synthesis cycles with an extended coupling time of 10 minutes during coupling of the 5'-dimethoxytrityl-2'-O-(pentyl-N-phthalimido0-N 6-benzyladenosine phosphoramidite into the oligonucleotide sequence. Coupling efficiency of >98% was observed for the 5'-dimethoxytrityl-2'-O-(pentyl-N-phthal-imido)-N 6-benzyladenosine phosphoramidite coupling. Removal of the N-phthalimido amine protecting group is effected simultaneously with NH₄OH deprotection of the benzyl and isobutyryl nucleotide base blocking groups.

B. Multiple Sites

An oligonucleotide of the sequence:

Oligomer 6 CTG TCT CCA* TCC TCT TCA* CT (SEQ ID NO: 6)

wherein A* represents a nucleotide modified to incorporate a pentylamino functionality was prepared as per the procedures of Example 9-A. This oligonucleotide is an antisense compound to the E2 region of the bovine papilloma virus-1 (BPV-1).

EXAMPLE 10

A. Coupling of OligonuCleotide Strand Having An Abasic Site to an Oligonucleotide Having an Amine Functionalized Space-spanning Group Two stranded, duplexed, cross-linked oligonucleotides of the structure:

Cross-linked Strands I

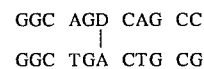

where "l" represents an O—(CH₂)₅—N—CH₂— cross-linkage between the oligonucleotide strands is prepared by reacting 2.80.D. units of Oligomer 5, i.e. the GGC TGA* CTG CG oligonucleotide of Example 9-A, in 100 µl of 0.2M NaOAc buffer (pH 5.02) with 2.37 O.D. units of Oligomer 2, i.e. the abasic oligonucleotide CGC AGD* CAG CC of Example 8-A-iii, dissolved in 10 µl of water. The combined solution was let stand for 2 hours. 10 mg of NaCNBH₃ was dissolved in 400 µl of 250 mM NaOAc (pH 5.02) and 25 µl of this solution was added to the reaction solution. After this addition, the final concentration of the cyanoborohydride in the solution was nearly 80 mM. The reaction was followed at 1 hr intervals by HPLC. The amine linked oligonucleotide had a retention time of 21.65 mins and the abasic oligonucleotide 22.46 mins. A product peak was observed at 24.07 mins. A slow increase in the product peak was observed. After 12 hrs the product was separated from the reaction mixture by HPLC yielding 1.05 O.D. units, 20.3%. A small aliquot of the product was re-injected into the HPLC column and observed as a single peak.

B. Gel Analysis

A gel analysis was carried out on the above crosslinked 11 mer oligonucleotides, i.e. Cross-linked Strands I. The cross linked material moved slower than either of its component 11 mer oligonucleotides, i.e. Oligomers 2 or 5. Indeed it had the same electrophoretic mobility as that of a 21 met oligonucleotide (11+11−1 for the loss of a base).

C. Ion Exchange Chromatography

Cross-linking of the Cross-linked Strands I was further confirmed by using ion exchange chromatography. The 21 met cross-linked strands, since they have the greatest amount of charge, were eluted at 0.25M salt concentration whereas the 11 mer components oligonucleotides were eluted at 0.15M salt concentration.

D. Cross-Linking Affirmation

Cross-linking as opposed to hybridization duplex formation was confirmed independently by gel analysis and by re-injection of the cross-linked strands into HPLC. Gel analysis of a mixture the two component oligonucleotides mixed together without cross-linking did not yield the 21 mer mobility product. Re-injection of the cross-linked product into HPLC did not produce an equilibrium mixture of the two single oligonucleotide strands but came out as a single peak.

EXAMPLE 11

Preparation of Oligonucleotide Having Sulfur Linking Atom Attaching an Amine Functionalized Space-spanning Groups Thereon An oligonucleotide of the sequence:

Oligomer 7 GGC T*GA CTG CG (SEQ ID NO: 5) wherein T* represents a nucleotide modified to incorporate a dodecylamino functionality joined to the thymidine nucleotide via a sulfur linking atom will be prepared as per the procedure of Example 9-A utilizing the oligonucleotide of Example 2-B-ii.

EXAMPLE 12

Preparation of Oligonucleotide Having Nitrogen Linking Atom Attaching an Amine Functionalized Space-spanning Groups Thereon An oligonucleotide of the sequence:

Oligomer 8 GGC TGA* CTG CG (SEQ ID NO: 5) wherein A* represents a nucleotide modified to incorporate a butylamino functionality joined to the adenosine nucleotide via a nitrogen linking atom will be prepared as per the procedure of Example 9-A utilizing the oligonucleotide of Example 2-C-ii.

EXAMPLE 13

Preparation of Oligonucleotide Having Carbon Linking Atom Attaching an Amine Functionalized Space-spanning Group Thereon An oligonucleotide of the sequence:

Oligomer 9 GGC TGA* CTG CG (SEQ ID NO: 5) wherein A* represents a nucleotide modified to incorporate a allylamine functionality joined to the adenosine nucleotide via a methylene linking atom will be prepared as per the procedure of Example 9-A utilizing the oligonucleotide of Example 2-D-i.

EXAMPLE 14

A. Coupling of Oligonucleotide Strands Via Abasic Site and Amine Functionalized Space-spanning Group Connecting Through a Sulfur Linking Group Two stranded, duplexed, cross-linked oligonucleotides of the structure:

Cross-linked Strands II

```
GGC AGD CAG CC
        |
GGC TGA CTG CG
``` where "|" indicates represents an S—$(CH_2)_{12}$—N—$CH_2$— crosslinkage between the individual oligonucleotides of the structure will be prepared by reacting Oligomer 7 of Example 11 with the abasic Oligomer 2 of Example 8-A-iii utilizing the procedure of Example 10-A.

B. Coupling of Oligonucleotide Strands Via Abasic Site and Amine Functionalized Space-spanning Group Connecting Through a Nitrogen Linking Group Two stranded, duplexed, cross-linked oligonucleotides of the structure:

Cross-linked Strands III

```
GGC AGD CAG CC
        |
GGC TGA CTG CG
``` where "|" represents an —NH—$(CH_2)_4$—N—$CH_2$— cross-linkage between the individual oligOnucleotides of the structure will be prepared by reacting Oligomer 8 of Example 12 with the abasic Oligomer 2 of Example 8-A-iii utilizing the procedure of Example 10-A.

C. Coupling of Oligonucleotide Strands Via Abasic Site and Amine Functionalized Space-spanning Group Connecting Through a Methylene Linking Group Two stranded, duplexed, cross-linked oligonucleotides of the structure:

Cross-linked Strands IV

```
GGC AGD CAG CC
        |
GGC TGA CTG CG
``` where "|" represents an —$CH_2$—CH=CH—N—$CH_2$— cross-linkage between the individual oligonucleotides of the structure will be prepared by reacting Oligomer 9 of Example 13 with the abasic Oligomer 2 of Example 8-A-iii utilizing the procedure of Example 10-A.

EXAMPLE 15

A. Preparation of Oligonucleotide Having a Hydrazine Functionalized Space-spanning Group Thereon i. Single Functionality An oligonucleotide of the sequence:

Oligomer 10 GGC TGU* CTG CG (SEQ ID NO: 7) wherein U* represents a nucleotide modified to incorporate a 2'-O-(octylhydrazino) functionality joined to the uridine nucleotide will be prepared as per the procedure of Example 9-A utilizing the oligonucleotide of Example 2-E-ii followed by deblocking of the benzylcarbazide protecting group via hydrogenolysis in the presence of palladium on charcoal.

ii. Multiple Functionalities

An oligonucleotide of the structure: Oligomer 11 AGC CAG AU*C U GA GCC UGG G**AG CUC UCU GGC U (SEQ ID NO: 8)
wherein U* represents an uridine nucleotide having a 2'-O-(octylhydrazine) group thereon and G** represents a guanosine nucleotide having a 2'-O-(octylhydrazine) group thereon will be prepared as per the procedure of Example 9-A utilizing the nucleotides of Examples 2-E-ii and 2-E-iv, respectively, to introduce the hydrazine functionalized space-spanning group containing nucleotides in the proper sequence. Deblocking of the benzylcarbazide protecting group is effected via hydrogenolysis in the presence of palladium on charcoal.

B. Preparation of Oligonucleotide Having a Hydroxylamine Functionalized Space-spanning Group Thereon An oligonucleotide of the sequence:

Oligomer 12 GGC TGU* CTG CG (SEQ ID NO: 7)

wherein U* represents a nucleotide modified to incorporate a octyl-hydroxylamine functionality joined to the cytidine nucleotide via an oxygen linking atom will be prepared as per the procedure of Example 9-A utilizing the oligonucleotide of Example 2-F-iii followed by treatment of the O-phthalimide group with methylhydrazine in DCM to generate the hydroxylamine functionality on the octyl space-spanning group.

C. Preparation of Oligonucleotide Having a Semicarbazide Functionalized Space-spanning Group Thereon An oligonucleotide of the sequence:

Oligomer 13 GGC TGU* CTG CG (SEQ ID NO: 7)

wherein U* represents a nucleotide modified to incorporate a pentyl-N-semicarbazide functionality joined to the uridine nucleotide via an oxygen linking atom will be prepared as per the procedure of Example 9-A utilizing the oligonucleotide of Example 2-G-i.

D. Preparation of Oligonucleotide Having a Hydrazide Functionalized Space-spanning Group Thereon An oligonucleotide of the sequence:

Oligomer 14 GGC TGU* CTG CG (SEQ ID NO: 7)

wherein U* represents a nucleotide modified to incorporate an ethyl hydrazide functionality joined to the uridine nucleotide via an oxygen linking atom will be prepared as per the procedure of Example 9-A utilizing the oligonucleotide of Example 2-H-iii.

E. Preparation of Oligonucleotide Having An Alcohol Functionalized Space-spanning Groups Thereon An oligonucleotide of the sequence:

Oligomer 15 GGC TGU* CTG CG (SEQ ID NO: 7)

wherein U* represents a nucleotide modified to incorporate a heptan-7-ol functionality joined to the uridine nucleotide will be prepared as per the procedure of Example 9-A utilizing the oligonucleotide of Example 2-I-iii.

EXAMPLE 16

A. Coupling of Oligonucleotide Strands Via Abasic Site and Hydrazine or Hydrazone Functionalized Space-spanning Group i. Hydrazine Linked Strands Two stranded, duplexed, cross-linked oligonucleotides of the structure:

Cross-linked Strands V

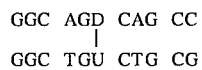

where "|" represents an O—$(CH_2)_8$—NH—NH—$CH_2$— cross-linkage between the individual oligonucleotides of the structure will be prepared by reacting Oligomer 10 of Example 15-A-i with the abasic Oligomer 2 of Example 8-A-iii followed by reduction of the resulting hydrazone linkage with $NaCNBH_3$ in NaOAc buffer as per the procedure of Example 10-A to form the hydrazine linkage.

ii. Hydrazone Linked Strands

The cross-linker strands of Example 10-A-i having a hydrazone cross-linkage can be formed by omitting the $NaCNBH_3$ reduction step of Example 10-A-i.

B. Coupling of Oligonucleotide Strands Via Abasic Site and Hydroxylamine or Oxime Functionalized Space-spanning Group i. Hydroxylamine Linked Strands Two stranded, duplexed, cross-linked oligonucleotides of the structure:

Cross-linked Strands VI

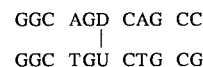

where "|" represents an O—$(CH_2)_8$—NH—O—$CH_2$— cross-linkage between the individual oligonucleotides of the structure will be prepared by reacting Oligomer 12 of Example 15-B with the abasic Oligomer 2 of Example 8-A-iii followed by reduction of the resulting oxime linkage with $NaCNBH_3$ in NaOAc buffer as per the procedure of Example 10-A to form the hydroxylamine.

ii. Oxime Linked Strands

The cross-linker strands of Example 10-B-i having an oxime cross-linkage can be formed by omitting the $NaCNBH_3$ reduction step of Example 10-A-i.

C. Coupling of Oligonucleotide Strands Via Abasic Site and Semicarbazide or Semicarbazone Functionalized Space-spanning Group i. Semicarbazide Linked Strands Two stranded, duplexed, cross-linked oligonucleotides of the structure:

Cross-linked Strands VII

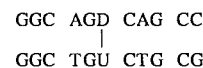

where "|" represents an O—$(CH_2)_8$—NH—NH—$CH_2$— cross-linkage between the individual oligonucleotides of the structure will be prepared by reacting Oligomer 13 of Example 15-C with the abasic Oligomer 2 of Example 8-A-iii followed by reduction of the resulting semicarbazone linkage with $NaCNBH_3$ in NaOAc buffer as per the procedure of Example 10-A to form the semicarbazide linkage.

ii. Semicarbazone Linked Strands

The cross-linker strands of Example 10-A-i having a semicarbazone cross-linkage can be formed by omitting the $NaCNBH_3$ reduction step of Example 10-A-i.

D. Coupling of Oligonucleotide Strands Via Hemiacetal Linkage Across An Abasic Site and An Alcohol Functionalized Space-spanning Group Two stranded, duplexed, cross-linked oligonucleotides of the structure:

Cross-linked Strands VIII

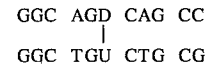

where "|" represents an O—$(CH_2)_7$—O—CH(OH)— cross-linkage between the individual oligonucleotides of the structure will be prepared by reacting Oligomer 15 of Example 15-E with the abasic Oligomer 2 of Example 8-A-iii in the presence of trifluoroacetic acid utilizing a modification of the procedure of Knorre, et al., "Nucleotide and Oligonucleotide Derivatives As Enzyme and Nucleic Acid Targeted Irreversible Inhibitors", Chemical Aspects, G. Weber (Ed.), Advance Press, Oxford, 1986, pp. 277–320.

EXAMPLE 17

Preparation of Oligonucleotide Having Multiple Space-spanning Groups That Include the Same Or Different Functionalities Thereon A. Aldehyde and Amine Functionality Containing Oligonucleotide A oligonucleotide of the structure: Oligomer 16 AGC CAG AUC UGA* GCC UGG GAG CU**C UCU GGC U (SEQ ID NO: 8) wherein A* represents an adenosine nucleotide having a 2'-O-(pentylamino) group thereon and U** represents a uridine nucleotide having a 2'-O-[propion-4-al bis(o-nitrobenzyl) acetal] group thereon will be prepared as per the procedure of Example 9-A utilizing the nucleotides of Examples 2-A-i and 2-K-i-b, respectively, for the functionalized space-spanning group containing nucleotides.

B. Multiple Thiol Functionality Containing Oligonucleotide

A oligonucleotide of the structure:
Oligomer 17 A*GC CAG AUC U GA GCC UGG GAG CUC UCU GGC U** (SEQ ID NO: 8)
wherein A* represents an adenosine nucleotide having a 2'-O-[S-trityl(hexyl-8-thiol)] group thereon and U** represents a uridine nucleotide having a 2'-O-[S-trityl(hexyl-8-thiol)] group thereon will be prepared as per the procedure of Example 9-A utilizing the nucleotides of Examples 2-J-ii-b and 2-J-ii-c, respectively, for the functionalized space-spanning group containing nucleotides.

C. Multiple Aldehydic Functionality Containing Oligonucleotide

An oligonucleotide of the structure:
Oligomer 18 GAC AGA GGU* AGG AGA AU* GA (SEQ ID NO: 3)
wherein U* is a 2'-O-[propion-3-al bis(o-nitrobenzyl) acetal] group will be prepared as per the procedure of Example 4-A utilizing the nucleotide of Example 2-K-i-b for the aldehydic functionalized space-spanning group containing nucleotides.

D. Thiol and Amine Functionality Containing Oligonucleotide

A oligonucleotide of the structure:
Oligomer 19 AGC CAG* AUC U GA GCC UGG GAG CUC U**CU GGC U (SEQ ID NO: 8)
wherein G* represents a guanosine nucleotide having a 2'-O-([2amylenyl]-N-phthalimide) group thereon and U** represents a uridine nucleotide having a 2'-O-[S-trityl(pentan-8-thiol)] group thereon will be prepared as per the procedure of Example 9-A utilizing the nucleotides of Examples 2-A-iv and 2-J-ii-e, respectively, for the functionalized space-spanning group containing nucleotides.

EXAMPLE 18

Multi-Site Cross-Linking Of Dual Strands of Oligonucleotides

A. Cross-Linking Via Dual Abasic Sites

Two stranded duplexed, multi-site cross-linked oligonucleotides of the structure:

Cross-linked Strand IX

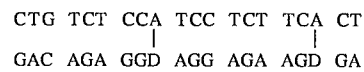

wherein "l" represents a cross-linkage between the strands, are prepared from Oligomer 4 from Example 8-A-iv and Oligomer 6 from Example 9-B utilizing the cross-linking procedure of Example 10-A. The resulting cross-linked strands are held together not only by hybridization of the duplex structures but also by the dual cross-linkages extending between the individual oligonucleotide strands.

B. Via Dual Space-spanning Groups

Two stranded duplexed, multi-site cross-linked oligonucleotides of the structure:

Cross-linked Strands X

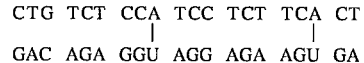

wherein "l" represents a cross-linkage having a covalent bond formed via an oxime linkage between the strands, is prepared from Oligomer 18 from Example 17-C and Oligomer 6 from Example 9-B. A solution of Oligomer 18 in water will be treated with hydrazine hydrate/ sodium cyanoborohydride to remove the aldehydic protecting groups.

Oligomer 6 is then added in 0.1M NaCl to hybridize the strands. Sodium acetate buffer is then added to effect cross-linking of the strands via formation of Schiff's bases between the amine and aldehyde groups. NaCNBH$_3$ is added to reduced the oxime linkage to an amine linkage whereby the resulting cross-linked strands will be held together not only by hybridization of the duplex structures but also by the multiple cross-links extending between the individual oligonucleotide strands.

EXAMPLE 19

Coupling of Two Sites on Single Strand

A single strand duplexed, cross-linked, hairpin loop oligonucleotide of the structure:

Cross-linked Strand XI

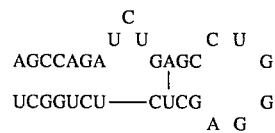

wherein "l" represents a cross-linkage having a covalent bond formed via an oxime linkage between the regions of the strand, is prepared from Oligomer 16 from Example 17-A. Oligomer 16 is taken up in 0.1M NaCl solution to effect hybridization and then treated with hydrogen in the presence of palladium on charcoal at atmospheric pressure until two equivalents of hydrogen are taken up indicating removal of the aldehydic protecting groups. Sodium acetate buffer is then added to effect the formation of a Schiff's base linkage between the amine and aldehyde groups. NaCNBH$_3$ is added to reduced the oxime linkage to an amine linkage whereby the resulting cross-linked strand will be held together not only by hybridization of the duplex stem portion of the hairpin loop structure but also by the covalent cross-linkage extending across the stem nucleotides.

EXAMPLE 20

Coupling Via Disulfide Linkage

A single strand of duplexed, cross-linked, bulged, hairpin loop oligonucleotide of the structure:

Cross-linked Strand XII

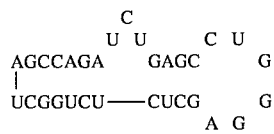

wherein "|⇌" represents a cross-linkage having a covalent bond formed via a disulfide linkage between the regions of the strand, is prepared from Oligomer 17 from Example 17-B.

Oligomer 17 will be solubilized in 0.1M NaCl solution under nitrogen to effect hybridization and then treated with silver nitrate to remove the S-trityl protecting groups. A disulfide bond is formed between the two free thiol groups via mild oxidation by bubbling air through the solution to cross-linkage the A-U site of the oligonucleotide. The oligonucleotide will be held in the hairpin loop structure not only by hybridization of the duplexed stem portions of the hairpin loop structure but also by the covalent disulfide bond connecting the stem regions.

EXAMPLE 21

Coupling Via Dialdehyde

Utilizing the procedure of Example 9-A an oligonucleotide of the sequence:

Oligomer 20 A*GC CAG AUC U GA GCC UGG GAG CUC UCU GGC U (SEQ ID NO: 8)

wherein A* is a 2'-O-(eicosylamino) adenosine nucleotide of Example 2-A-ii-c is prepared. The oligonucleotide is removed from the CPG synthetic column and de-salted on Sephadex G-25 Oligomer 20 will then be treated as per the peroxidation procedure of Lemairte et. al., *Proc. Natl. Acad. Sci. USA*, 84:648 (1986) to effect periodate-oxidation of the sugar moiety of the 3' terminus uridine nucleotide.

A single strand of duplexed, cross-linked, hairpin loop oligonucleotide of the structure:

Cross-linked Strand XIII

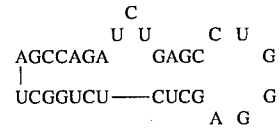

wherein "|" represents a covalent cross-linkage formed via the oxidized, ring opened sugar of the 3'-terminal nucleotide and the amine group on the opposing nucleotide of the duplexed stem portion of the strand. Such cross-linkage is formed from the periodate-oxidized oligonucleotide by solubilizing the oxidized oligonucleotide in 0.1M NaCl to effect hybridization followed by the addition of sodium acetate buffer and NaCNBH$_3$. As the intermediate Schiff's base cross-linkage is formed, it is reduced to an amine linkage by the addition of NaCNBH$_3$ as per the procedure of Example 10-A.

EXAMPLE 22

Coupling Via Acetal Linkage

Utilizing the procedure of Example 9 an oligonucleotide of the sequence:

Oligomer 21 A*GC CAG AUC U GA GCC UGG GAG CUC UCU GGC U (SEQ ID NO: 8)

wherein A* is a 2'-O-[propion-3-al bis(o-nitrobenzyl) acetal] functionalized adenosine nucleotide will be prepared as per the procedure of Example 4-A utilizing the nucleotide of Example 2-K-i-a to introduce the aldehydic functionalized space-spanning group containing nucleotide with the oligonucleotide sequence.

The oligonucleotide is removed from the CPG synthetic column and de-salted on Sephadex G-25.

A single strand of duplexed, cross-linked, hairpin loop oligonucleotide of the structure:

Cross-linked Strand XIV

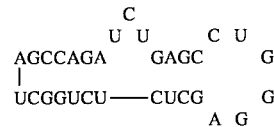

wherein "|" represents an acetal cross-linkage formed between the 2', 3'-hydroxyl moieties of the sugar on the 3'-terminal U nucleotide and the aldehydic functionality on the opposing A nucleotide of the duplexed stem portion of the strand, is prepared by effecting cross-linking in 0.1M NaCl in the presence of trifluoroacetic acid. This procedure is a modification of the procedure of Knorre et. al., "Nucleotide and Oligonucleotide Derivatives As Enzyme and Nucleic Acid Targeted Irreversible Inhibitors", Chemical Aspects, G. Weber (Ed.), Advance Press, Oxford, 1986, pp. 277–320. Upon reaction of the free aldehydic group on the A nucleotide, cross-linking to the opposing 2', 3'-hydroxyl's of the 3'-terminus U nucleoside will yield a covalent cross-linkage between nucleotides of the stem portion of the hairpin loop bulged single stranded oligonucleotide.

EXAMPLE 23

Coupling Via Heterobifunctional Linker on Single Strand

A single strand of duplexed, cross-linked, hairpin loop oligonucleotide of the structure:

Cross-linked Strand XV

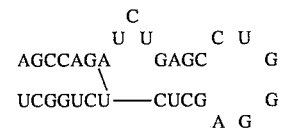

wherein "\" represents a cross-linkage formed via a homobifunctional linker between the G and U nucleotides of duplexed regions of the strand across the G and U nucleotides of the two separate regions that are one base removed from Watson/Crick base pairs, is prepared from Oligomer 19 from Example 17-D. The Oligomer 19 will first be taken up in a 0.1M NaCl solution to effect hybridization of the oligonucleotide into a hairpin loop single strand duplexed structure. The reaction solution is then treated with silver nitrate in buffer to remove the S-trityl blocking group. A aliquot of N-succinimidyl 3-(2-pyridyldithio)propionate (SPDP) (Pierce, Rockford, Ill.) in weak alkaline is added to effect coupling of the amine functionality to the linker. The pH is then adjusted to pH 4.5 to effect exchange of the 2-pyridyl-disulfide and the thiol functionality on the oligonucleotide and in doing so to effect cross-linking of the strand. The strand will thus be held together not only by hybridization of the duplex stem portion of the hairpin loop bulged structure but also by the heterobifunctional cross-linker extending across the stem nucleotides.

EXAMPLE 24

Coupling Via Homobifunctional Linker

A single strand of duplexed, cross-linked, bulged, hairpin loop oligonucleotide of the structure:

Cross-linked Strand XVI

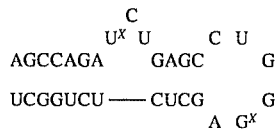

wherein a cross-linkage is formed via a homobifunctional linker spanning between the $U^x$ nucleotide on the UCU bulge and the $G^x$ nucleotide of the AGGGUC loop regions of the strand, is prepared from Oligomer 11 from Example 15-A-ii. Molecular models of the proposed tertiary structure of Strand XVI indicate that the $U^x$ and $G^x$ nucleotides lie in close physical proximity to each other. To prepare Strand XVI the Oligomer 11 will first be taken up in a 0.1M NaCl solution to effect hybridization of the oligonucleotide into a hairpin loop bulged single strand duplexed structure. The reaction solution is then adjusted to be a 0.2M sodium borate buffer. Disuccinimidyl suberate (DSS, Pierce, Rockford, Ill.) is added to effect cross-linking of the hydrazine reactive functionalities of the uridine-guanosine nucleotides. The U nucleotide of the bulge and G nucleotide of the loop are linked via hydrazide linkages between the functionalities on the space-spanning groups and the homobifunctional cross-linker. In this structure, the $U^x$ nucleotide of the interior loop and the $G^x$ nucleotide of the hairpin loop are neither complementary to nor hybridizable with one another but they are located in 3-dimensional space in proximity with each other because of the higher order structure of the oligonucleotide. The cross-linkage spans this 3-dimensional space to fix the oligonucleotide in the higher order structure.

Example 25

Synthesis of 2'-O-Hexylaminouridine

Preparation of 5'-Dimethoxytrityl-2'-(O-hexyl-N-phthalimido)uridine phosphoramidite 2',3'-O-Dibutyl stannylene-uridine was synthesized according to the procedure of Wagner, et al., *J. Org. Chem.*, 1974, 39, 24. This compound was dried over $P_2O_5$ under vacuum for 12 hrs. To a solution of this compound (29 g, 42.1 mmols) in 200 ml of anhydrous DMF were added (16.8 g, 50 mmols) of 6-bromohexyl phthalimide and 4.5 g of sodium iodide and the mixture was heated at 130° C. for 16 hrs. under argon. The reaction mixture was evaporated, co-evaporated once with toluene and the gummy tar residue was applied on a silica column (500 g). The column was washed with 2L of EtOAc followed by eluting with 10% MeOH:90% EtOAc. The product, 2'-and 3'-isomers of O-hexyl-Ω-N-phthalimido uridine, eluted as an inseparable mixture ($R_f$=0.64 in 10% MeOH in EtOAc). By $^{13}C$ NMR, the isomeric ratio was ca. 55% of the 2' isomer and ca. 45% of the 3' isomer. The combined yield was 9.2 g (46.2%). This mixture was dried under vacuum and re-evaporated twice with pyridine. It was dissolved in 150 mL anhydrous pyridine and treated with 7.5 g of dimethoxytrityl chloride (22.13 mmols) and 500 mg of DMAP. After 2 hrs. TLC (6:4 EtOAc:Hexane) indicated complete disappearance of the starting material and a good separation between 2' and 3' isomers ($R_f$=0.29 for the 2' isomer and 0.12 for the 3' isomer). The reaction mixture was quenched by the addition of 5ML of $CH_3OH$ and evaporated under reduced pressure. The residue was dissolved in 300 mL $CH_2Cl_2$, washed successively with saturate NaHCO3 followed by saturated NaCl solution. It was dried ($MgSO_4$) and evaporated to give 15 g of a brown foam which was purified on a silica gel (500 g) to give 6.5 g of the 2'-isomer and 3.5 g of the 3' isomer.

The 2'-O-hexyl-O-N-phthalimido-5'-DMT-uridine (4 g, 5.2 mmole) was dissolved in 40 ML of anhydrous $CH_2Cl_2$. To this solution diisopropylaminetetrazolide (0.5 g, 2.9 mmol) and bis(isopropylamino)-β-cyanoethoxyphosphine (2.5 mL, 7.0 mmol) were added and stirred overnight. TLC (1:1 EtoAC/hexane) showed complete disappearance of starring material. The reaction mixture was transferred with $CH_2Cl_2$ and washed with saturated $NaHCO_3$ (100 ML) followed by saturated NaCl solution. The organic layer was dried over anhydrous $Na_2SO_4$ and evaporated to yield 6.4 g of a crude product which was purified in a silica column (200 g) using 1:1 hexane EtOAc to give 4.6 g (4.7 mmol, 90%) of the desired phosphoramidite.

Example 26

Oligomer Synthesis and NMR Characterization of an Oligonucleotide Containing U-2'-O-hexylamine Linker An oligonucleotide of the sequence:

Oligomer 22 TU*T where U* represents the hexylamine modified uridine moiety, was synthesized on a 10 mmol synthesis in the DNA synthesizer. The phosphoramidite from Example 25 was used as a 0.12M solution in $CH_3CN$. After deprotection of the oligonucleotide it was purified in a reverse phase HPLC column to get the pure trimer (any oligonucleotide containing undeprotected phthalimido group was separated from the trimer). The oligonucleotide was dried, desalted and dissolved in 600 uL $D_2O$ (app. 50 O.D., $A_{260}$). Both the proton NMR and $^{31}P$ NMR were examined. $^1H$ NMR: 1.0–1.8 (m, CH2 protons from the hexyl chain); 5.75 (d); 5.9(d); 6.1 (t); 6.15 (t); 7.5 (s). $^{31}p$ NMR: −0.2; −0.4 ppm (two lines).

Example 27

Synthesis Illustrating Preparation of any Nucleotide (A, U, C or G) Placed Opposite to an Abasic Site in an Opposing Strand A. Oligonucleotide Synthesis An oligonucleotide of the sequence:

Oligomer 23 GGC TGU* CTG CG (P=O) (SEQ ID NO: 7)

wherein U* indicates a 2'-O-(hexylamino) uridine nucleotide was prepared using an extended coupling time of 10 minutes. 5'-Di-methyoxytrityl-2'-O-(hexyl-N-phthalimido) uridine phosphoramidite was used as a 0.12M solution in anhydrous CH3CN. The oligonucleotide was deprotected, purified in reverse phase HPLC (trityl-on), deprotected at the 5'-position and purified again to remove any undeprotected phthalimido oligonucleotide.

B. Cross Linking Reaction

The Oligomer 23 oligonucleotide was reacted with the abasic oligonucleotide CGC AGD* CAG CC (Oligomer 2) with a crosslinking efficient of >90%. The formation of the conjugate was confirmed by reverse phase HPLC, ion-exchange HPLC and finally by the observation of base paired crosslinked duplex imino protons in the NMR spectrum.

Example 28

Formation of a Crosslink Between a Chimeric Oligonucleotide and an Abasic Site Containing Oligonucleotide.

An oligonucleotide of the sequence:

Oligomer 24 $G_sG_sC_o\ T_oG_oU^*_o\ C_oT_oG_s\ C_sG$ (SEQ ID NO: 7)

where s represents a phosphorothioate backbone, o represents a phosphodiester backbone and U* represents a 2'-O-(hexylamino) uridine, was synthesized with a mixed (phosphodiester/phosphorothioate) backbone using either a conventional iodine oxidation (P=O) or a Beaucage reagent oxidation (P=S) in the respective oxidation steps. The oligonucleotide was synthesized, purified and crosslinked with CGCAGD*CAGCC. The crosslinked duplex was characterized by $^1$H NMR, Gel analysis, HPLC (reverse phase and ion-exchange).

Example 29

Cross Linked Nucleic Acid Duplex Involving Connectivity Between two Abasic Sites:

Oligonucleotides with the following sequences were synthesized:

Oligomer 2 CGC AGD* CAG CC

Oligomer 26 GGC TGD* CTG CG (SEQ ID NO: 9).

Oligomer 26 was obtained from a precursor oligomer:

Oligomer 25 GGC TGU CTG CG (SEQ ID NO: 7)

where U represents 2'-deoxyuridine, by the action of uracil-DNA glycosylase. Oligomer 2 is reacted with 1,6-hexanediamine in NaOAc/NaCNBH₃ medium and a product isolated that has a free amino group located on the linker. This modified oligonucleotide is mixed with Oligomer 26 in NaOAc buffer followed by the addition of NaCNBH₃ in NaOAC buffer. The resultant cross link has a connectivity between two abasic sites separated by the —NH—(CH₂)₆—NH—linker.

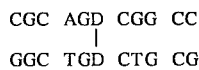

where "l" represents a —CH2—NH—(CH₂)₆—NH—CH2—crosslinker.

Example 30

$T_m$ Determination of the Cross-linked Strands I

The melting behavior of the crosslinked duplex, Crosslinked Strand I, was determined at 100 mM Nacl, 10 mM sodium phosphate, 0.1 mM EDTA at pH 7.0 at 4 mM each strand concentration.

|  | $T_m$ |
| --- | --- |
| Oligomer 5 - Oligomer 1 duplex (wild type) | 48° C. |
| Oligomer 5 - Oligomer 2 duplex (abasic site) | <30° C. |
| Oligomer 5 - Oligomer 2 Cross-linked Strands I | 74° C. |

The higher $T_m$ of the crosslinked duplex confirmed the covalent linkage between the two strands (Oligomer 5 and Oligomer 2).

EXAMPLE 31

2'-O-Hexenyluridine and 3'-O-Hexenyluridine

To 2', 3'-O-di-n-butyl-stannyleneuridine (10.5 g, 15.3 mmole) in DMF (60 ml) was added 6-bromo-1-hexene (2.8 g, 17.54 mmole) and sodium iodide (3.3 g, 15.3 mmole). The reaction mixture was heated to 150 ° C. under an atmosphere of argon. The reaction mixture is stirred at 150 ° C. for 19 hours and then cooled to room temperature. Methanol (20 ml) was added and the reaction mixture was stirred for 30 minutes. The resulting mixture is evaporated under reduced pressure to give a dark brown residue. The residue was partitioned between HCl (1N) and dichloromethane. The organic layer is separated, washed with brine, dried over magnesium sulfate, filtered, and evaporated under reduced pressure. The residue was coevaporated with toluene (20 ml, X3). The residue was then purified by flash column chromatography over silica gel using methanol-ethyl acetate (1/9) as the eluent. The pure fractions were pooled together and evaporated to dryness to give 3.3 g (63%) of a mixture of the title compounds (in the ratio of 60:40) as a foam. TLC: (Rf: 0.8; 10% MeOH/EtOAc); $^1$H NMR: (DMSO-$d_6$) δ 1.4 (m, 8H, CH₂), 2.0 (m, 4H, CH₂), 3.4–3.6 (m, 4 H, H-5', H-5"), 3.8 (t, 2H, CH₂), 3.9 (m, 1 H, H-4'), 4.1 (t, 1 H, H-3'), 4.2 (t, 1H, H-2'), 4.9 (t, 1 H, H-3'), 5.0 (t, 1 H, H-2'), 5.0 (br, 1 H, 3'-OH), 5.8 (m, 2H, CH & 2'-OH), 5.8 (q, 2H, H-5 & H-5), 6.2 & 6.4 (d &d, 2H, H-1', H-1'), 7.9 (d, 1 H, H-6), 8.0 (d, 1 H, H-6), 11.4 (s, 2H, NH).

EXAMPLE 32

5'-O-(4,4'-Dimethoxytrityl)-2'-O-hexenyluridine

The mixture of compounds Example 31 (3.1 g, 9.5 mmole) were dissolved in pyridine (20 ml) and evaporated to dryness. This was repeated three times to remove traces of moisture. To this dried residue, in dry pyridine (50 ml) was added 4,4'-dimethoxytrityl chloride (3.5 g, 10.4 mmole). The reaction mixture was stirred at room temperature for 16 hrs under an atmosphere of argon. Methanol was added and the reaction mixture was stirred for another 30 minutes then evaporated to dryness under reduced pressure. The residue was partitioned between dichloromethane and dilute sodium carbonate solution. The organic layer was dried over magnesium sulfate and evaporated. The residue was purified by flash column chromatography over silica gel using (300 g) using 3:1 hexane/ethyl acetate followed by 1:1 hexane/ethyl acetate containing 1% triethyl amine as the eluent. The appropriate fractions were pooled to geve 2.3 g of the 2'-isomer, 0.9 g of the 3'-isomer, and 1.4 g of the mixed product(72% combined yield). The 2'-isomer gave the following characteristic properties, TLC: (Rf: 0.5; 5% MeOH/CH$_2$Cl$_2$); $^1$H NMR: (DMSO-d$_6$) δ 1.5 (m, 4 H, CH$_2$), 2.1 (q, 2H, CH$_2$), 3.6 (m, 2H, H-5', H-5"), 3.7 (m, 2H, CH$_2$), 3.8 (s, 3H, OCH$_3$), 3.9 (m, 1 H, H-4'), 4.0 (m, 1 H, H-3'), 4.5 (m, 1 H, H-2'), 5.0 (d, 1 H, H-5), 5.1 (m, 2H, CH$_2$), 5.8 (m, 1 H, CH), 5.9 (s, 1 H, H-1'), 6.8 & 7.3 (m, 13H, ArH), 8.1 (d, 1 H, H-6), 8.3 (br, 1 H, NH). Anal. cald for C36H40N2O8-½ H$_2$O, calc C, 68.77; H, 6.41; N, 4.45; found C, 67.80; H, 6.48; N, 4.39. The 3'-isomer gave the following resonances; $^1$H NMR (DMSO-d$_6$) δ 1.5 (m, 4H, CH$_2$), 2.1 (q, 2H, CH$_2$), 3.6 (m, 2H, H-5' & H-5"), 3.8 (s, 6H, OCH$_3$), 4.0 (m, 2H, CH$_2$), 4.1 (m, 1H, H-4'), 4.2 (m, 1H, H-3'), 4.3 (m, 1H, H-2'), 5.0 (m,-2H, CH$_2$), 5.4 (d, 1H, H-5), 5.8 (m, 1H, CH), 5.9 (s, 1H, H-1'), 6.8–7.3 (m, 13H, aromatic) , 7.8 (d, 1H, H$_6$) , 8.9 (bs, 1H, NH).

EXAMPLE 33

5'-O-(4,4'-Dimethoxytrityl)-2'-O-hexenyluridine-3'-O-[( 2-cyanoethyl-N,N-diisopropyl)]phosphoramidite The substrate of Example 32 (1.3 g, 2.1 mmole), was dissolved in dry pyridine and evaporated to dryness. This was repeated three times to remove water. The dried substrate (3) was dissolved in dry dichloromethane (15 ml) under an atmosphere of argon. To this dichloromethane solution was added N,N-diisopropylamine tetrazolide (0.22 g, 1.23 mmole) and 2-cyanoethyl-N,N,N',N'-tetraisopropyl-phosphoramidite (1.9 g, 5.9 mmole). The reaction mixture was stirred at room temperature for 16 hrs. The reaction mixture was poured onto saturated NaHCO$_3$ (aq) (200 ml) and stirred for 30 minutes. The biphasic mixture was separated and the aqueous phase was extracted with CH$_2$Cl$_2$. The CH$_2$Cl$_2$ extracts were combined with the CH$_2$Cl$_2$ phase and the solution was dried over anhydrous Na$_2$SO$_4$. The solution was filtered and evaporated to dryness under reduced pressure. The resiude was purified by flash column chromatography over silica gel using ethyl acetate-hexane containing 1% TEA as the eluent. The main fractions were collected and evaporated to dryness to give 1.0 g (60%) of the title compound as a white foam. TLC: (Rf: 0.5 & 0.4; 50 EtOAc/Hexane/1% TEA); $^-$P NMR: (CDCl$_3$) δ 150.71 ppm & 150.66 ppm.

Example 34

Synthesis of Oligonucleotides having a single functionality: 2'-O-hexenyl-uridine nucleotides The oligonucleotide was prepared using standard conditions. The 2'-O-hexenyl-uridine phosphoramidite was used as a 0.2M solution. A 10 min wait step was introduced after coupling. A coupling efficiency of >88% was observed for the 2'-O-hexenyl-uridine phosphoramidite coupling. The following oligonucleotides were prepared:

Oligomer 27GAU*CT (DNA; P=O; U*= 2'-O-hexenyluridine

Oligomer 28 CUC UCU GGU,C (SEQ ID NO: 10) (2'-OMe RNA; P=O; U*=2'-O-hexenyl-uridine)

The oligonucleotides were deprotected and HPLC purified. After final desairing, homogeneous, pure oligonucleotides were obtained. Oligomer 27 was used to establish the structure of the olefinic linker 2'-O-hexenyl group in the oligonucleotides. The 400 MHz proton NMR spectrum revealed the expected eight lines from the base protons from G,A, C, T and U* between 7.4 and 8.6 ppm; in addition, the ABM portion of ABMX spin coupling network was observed: the AB portion around 4.8 and 5.0 ppm (=CH$_2$; AB part of the ABMX proton coupling system) and 5.6 and 5.8 ppm (=CH; M part of the ABMX proton coupling system. The 120 MHz phosphorous spectrum showed the four interphosphate backbone signals.

The sequence Oligomer 28 represents an RNA mimic of the TAR element between the bases 37 and 46 was subsequently used to form the right hand side of the stem in a crosslinked oligonucleotideo Example 35

Conversion of Olefinic Linker into a Diol Linker: Formation of Oligomer 27-Diol

Oligomer 27 (GAU*CT, U*=2'-O-hexenyl A) (50 A$_{260}$ units, approx. 1 mmol) was dissolved in 2 ml water in a test tube. 4-Methylmorpholine N-oxide (14 ml of a 1% solution in water) and osmium tetroxide (340 ml of a 4% solution in water) were added. The mixture was vortexed and the test tube completely covered with foil. After 1 hr, the reaction mixture was purified by size-exclusion chromatography (Sephadex G-25) and lyophilized to yield 50 A$_{260}$ units of product. The product was analyzed by reverse-phase HPLC using the BIOTIN gradient (5% to 40% acetonitrile over 55 min) of % acetonitrile in 0.05M triethylammonium acetate pH 7.0. The product was a single peak with a retention time of 23.50 min (vs. 28.96 min for the starting material using the same gradient). Proton NMR of the product (400 MHz) showed the absence of a vinylic proton signals between 4.8 and 5.0 ppm (=CH$_2$; AB part of the ABMX proton coupling system) and 5.6 and 5.8 ppm (=CH; M part of the ABMX proton coupling system.

Example 36

Conversion of Diol Linker into an Aldehyde Linker

To 10 OD oligonucleotide containing the diol linker of Example 35 in 200 ul water, (final oligonucleotide concentration =0.82 mM), 42.8 ul of NaIO$_4$ solution (1% solution in water; final NaIO$_4$ concentration=8.2 mM; 10 equivalents) was added, vortexed and left in a microfuge tube. After 2 hr the product was purified by size exclusion chromatography and analyzed by RP-HPLC using the CHOL gradient. The complete disappearance of diol peak and a broad new peak at a higher retention time indicated the formation of the aidehyde. The solution was applied to a Sephadex G-25 column (0.7×15 cm) and the oligonucleotide fractions were combined.

Example 37

One Pot Conversion of Olefinic Linker into an Aldehyde Linker

About 5 O.D. units (A$_{260}$) of Oligomer 27 (approximately 100 nmols) was taken up in 100 ml of water in a microfuge tube. The oligonucleotide was then treated with 1 microliter of N-methyl morpholine N-Oxide solution (3 mg dissolved in 1000 μl of water; 0.025M) followed by 25 microliters of a 4% OsO$_4$ solution in water. The solution was vortexed and 10 microliters of NaIO$_4$ solution (10 mg dissolved in 1000 μl of water; 0.046M) was added. The tube was covered with aluminum foil and the solution was let stand for 1 hour. The solution was applied to a Sephadex G-25 column (0.7×15 cm) and the oligonucleotide fractions were combined. Analytical HPLC showed nearly quantitative conversion to the aldehyde product.

Example 38

Conjugation of Pyrene Intercalator into Aldehyde Linker

A. Formation of Imine Product (Schiff Base)

To 10.0 OD aldehyde oligonucleotide of the previous example in 1M NaOAc pH 4.9, 200 ml and 100 ul DMF, 3 mg pyrenebutyrylhydrazide (Molecular Probes, Eugene, OR) was added in a microfuge tube. The reaction tube was then mixed and vortexed. After one hour, 25 ul of the reaction mix was removed and centrifuged to pellet the undissolved pyrene reagent. The supernatant was analyzed by RP-HPLC using the CHOL gradient for the Schiff base formation between the aldehyde linker and pyrenebutyl hydrazide.

| Result: | Aldehyde peak | ca. 18.02 |
|---|---|---|
| | Product peak | 31.63 |
| | Pyrene reagent | 40.05 |

B. Formation of Amine Product

The imine from step A is reduced with $NaCNBH_3$ solution to give the (200 ul of 6M $NaCNBH_3$ in 250 mM NaOAc pH 4.9) the amine product. The reaction test tube was left overnight and the solution was applied to a Sephadex G-25 column (0.7×15 cm) and the oligonucleotide fractions were combined. Analytical HPLC showed nearly quantitative conversion to the pyrene conjugation product.

TABLE II

Summary of HPLC Retention Times:

| Compound | HPLC Retention time (CHOL program) min. |
|---|---|
| 27 | 26.85 |
| 27-diol | 16.92 |
| 27-aldehyde | 18.02 |
| 27-pyrene conjugate | 29.81 |
| Pyrene butylhydrazide | 40.05 |
| 27-pyreneimine (Schiff Base) | 31.63 |
| $NaCNBH_3$ | 2.26 |

HPLC conditions: column; Waters Delta-Pak $C_{18}$; gradient: linear, 5–80% acetonitrile over 55 min.

Example 39

Oligonucleotides Having 2'-O-Hexylamine and 2'-O-Decylamine Containing Adenosines The 5'-dimethoxytrityl-2'-O-(hexyl-N-phthalimido)-2'-deoxyadenosine phosphoramidite and 5'-dimethoxytrityl-2'-O-(decyl-N-phthalimido)-2'-deoxyadenosine phosphoramidite were used to synthesize the following oligonucleotides. A 0.2M solution of the respective amidite was used and a 10 min wait step was introduced after coupling. A coupling efficiency of >88% was observed for the 2'-O-modified phosphoramidite coupling.

Oligomer 29 GA*C CAG AUC UGA G (SEQ ID NO: 11) (2'-OMe RNA; P=O; A*=2'-O-hexylamino adenosine)

Oligomer 30 GA*C CAG AUC UGA G (SEQ ID NO: 11) (2'-OMe RNA; P=O; A*=2'-O-decylamino adenosine)

The sequences of Oligomers 29 and 30 represents an RNA mimic of the TAR element between the bases 16 and 28 and are used to form the left hand side of the stem in a crosslinked oligonucleotide having a bulge (vide infra).

The oligonucleotides were deprotected and HPLC purified. After final desalting, homogeneous, pure oligonucleotides were obtained.

Example 40

Crosslinked Oligonucleotides Having 2'- to 2'-Linkages:

The Nucleophile at the Position 17 and the Electrophile at the Position 45 of TAR:

Interstrand Crosslink Synthesis

In this example a nucleophilic arm from one oligonucleotide strand is crosslinked to the electrophilic arm from the complementary strand.

A. Generation of Aldehyde Linker from Oligomer 28:

Oligomer 28 is dissolved in water and treated with NMMO, $OsO_4$ and sodium periodate as described in Example 37. It is then purified in a Sephadex G-25 column to give the aldehyde linker containing oligonucleotide.

B. 2' to 2' Crosslink with a Hexylamine Nucleophilic Linker:

Oligomer 29 is mixed with one equivalent of the aldehyde linker containing oligonucleotide from the step A in NaOAc buffer, pH 5.0. and reductive amination is carried out with 6M $NaCNBH_3$ in 250 mM NaOAc pH 5.0. After leaving the reaction overnight, the reaction mixture is desaired. Analytical HPLC and Gel electrophoresis indicated formation of the crosslink between Oligomers 28 and 29. The crosslinked product is finally purified by preparative reverse phase HPLC.

C. 2' to 2' Crosslink with a Decylamine Nucleophilic Linker:

Oligomer 30 is mixed with one equivalent of the aldehyde linker containing oligonucleotide from the step A in NaOAc buffer, pH 5.0. and reductive amination is carried out with 6M $NaCNBH_3$ in 250 mM NaOAc pH 5.0. After leaving the reaction overnight, the reaction mixture is desalted. Analytical HPLC and Gel electrophoresis indicated formation of the crosslink between 9104 and 9106. The crosslinked product is purified by preparative reverse phase HPLC. NMR (and Molecular Modeling) show a more flexible crosslink between Oligomers 28 and 30 than that between Oligomers 29 and 30.

Example 41

Crosslinked Oligonucleotides Having 2'- to 2'-Linkages:

The Nucleophile at the Position 16 and the Electrophile at the Position 46 of TAR:

Intrastrand Crosslink from the Oligonucleotides Having the Electrophile and Nucleophile in the Same Strand at Complementary Sites The following oligonucleotides are RNA and DNA decoys of HIV-1 TAR element representing the nucleotide sequence between the base numbers 15 and 47. The nucleophilic tether was positioned at the position 16 and the electrophilic tether was positioned at 46 in the same strand to acheive a 2' to 2' crosslink as suggested by molecular modeling calculations.

The following four oligonucleotides were synthesized each at a 10 micromole scale. The appropriate 2'-O-modified phosphoramidites were used. A 0.2M solution of each amidite was used and a 10 min wait step was introduced after coupling at the modified amidite coupling. A coupling efficiency of >90% was observed for the novel phosphoramidite coupling.

Oligomer 31 UA*G CCA GAU CUG AGC CU GGG AGC UC UCU GGC U*A (SEQ ID NO: 12) (2'-OMe RNA; P=O; A*=2'-O-hexylamino adenosine; U*=2'-O-hexenyl uridine)

Oligomer 32 UA*G CCA GAU CUG AGC CU GGG AGC UC UCU GGC U*A (SEQ ID NO: 12) (2'-OMe RNA; P=O; A*=2'-O-decylamino adenosine; U*=2'-O-hexenyl uridine)

Oligomer 33 TA*G CCA GAT CTG AGC CT GGG AGC TC TCT GGC U*A (SEQ ID NO: 13) (DNA analog of TAR; P=O; A*=2'-O-hexylamino adenosine; U*=2'-O-hexenyl uridine)

Oligomer 34 TA*G CCA GAT CTG AGC CT GGG AGC TC TCT GGC U*A (SEQ ID NO: 13) (DNA analog of TAR; P=O; A*=2'-O-decylamino adenosine; U*=2'-O-hexenyl uridine)

The oligomers on CPG were deprotected in $NH_4OH$ and lyophilized. The oligomers were then trityl-on purified by prep HPLC using the PREP and CHOL programs for the DNA's and 2'-OMe RNA's, respectively. The oligomers were detritylated in 80% acetic acid for one hour, lyophilized, and finally purified by size-exclusion. Purified oligos were analyzed by UV, HPLC and PAGE. All were predominantly one band by PAGE, but multiple peaks (with similiar retention times) by HPLC, presumably due to the secondary structure of the TAR element.

Example 42

Crosslinked Oligonucleotides Having 2'- to 2'-Linkages:

The Nucleophile at the Position 16 and the Electrophile at the Position 46 of TAR:

Intrastrand Crosslink from the Oligonucleotides Having the Electrophile and Nucleophile in the Same Strand at Complementary Sites Each oligonucleotide from Example 41 is subjected to the following sequence of events to synthesize crosslinked oligonucleotides: a) the oligonucleotide is dissolved in water and treated with NMMO, $OsO_4$ and sodium periodate to generate the aldehyde from the olefin; b) it is then purified in a Sephadex G-25 column to give the purified aldehyde linker containing oligonucleotide; c) the oligonucleotide is lyophilized, dissolved in NaOAc buffer, pH 5.0. and reductive amination is carried out with 6M $NaCNBH_3$ in 250 mM NaOAc pH 5.0; d) after leaving the reaction overnight, the reaction mixture is desaired; f) analytical HPLC indicats formation of the crosslink between the nucleophilic and electrophilic arms; and g) the crosslinked product is finally purified by preparative reverse phase HPLC.

EXAMPLE 43

S-Trityl-6-mercaptohexylbromide, 1,1',1"-{[( 6-bromohexyl)-thio]methylidyne}trisbenzene To a solution of triphenylmethanethiol (Fluka; 69 g, 250 mmol) in 500 mL 95% ethanol (EtOH) was added 11 grams of sodium hydroxide dissolved in 75 mL of water (275 mmol). After stirring for about 15 minutes in argon atmosphere, using an addition funnel, 1,6-dibromohexane (91.5 g, 375 mmol, 58 mL) dissolved in 100 mL of 95% EtOH was added dropwise over a period of 1 hour with vigorous stirring. After about 15 minutes of stirring of addition, a brown white solid separates out from the reaction flask. After stirring for additional 4 hours, the reaction mixture was filtered. The filtrate was evaporated under high vacuum and the oily residue was combined with the filtered residue and dissolved in 500mL $CH_2Cl_2$, filtered again, the filtrate was washed once with water (200 mL) and once with saturated NaCl solution. After drying the $CH_2Cl_2$ layer over $MgSO_4$, it was concentrated to 200 mL in volume. About 200 mL of hexane was added and the solution was left in freezer. Three crops of cream white product was isolated out. Total yield 81 g (184 mmol, 73% yield). After one more recrystallization the product melted at 91°–92 ° C.

EXAMPLE 44

2'-O-[6-[(Triphenylmethyl)thio]hexyl]adenosine and 3'-O-[6-[(Triphenylmethyl)thio]hexyl]adenosine (Compounds 5 and 6)

Adenosine (22.5 g) was alkylated with this trityl-6-mercaptohexylbromide (37.5 g) in the presence of DMF and sodium hydride to yield a mixture of the 2'-O-alkylated and 3'-O-alkylated compounds, i.e. 2'-O-[ 6-[(triphenylmethyl)thio]hexyl]adenosine and 3'-O- [6-[(triphenylmethyl)thio]hexyl]adenosine, in the ratio of 84:16 (as judged by $^{13}C$ NMR). The yield was 27%.

EXAMPLE 45

N-Benzoyl-2'-O-{6-[(triphenylmethyl) thio]hexyl)adenosine and N-benzoyl-3'-O-{6-[(triphenylmethyl) thio]hexyladenosine}

To 16.5 grams of alkylation mixture of Example 44 (26.4 mmols) in 260 mL of dry pyridine added 17 mL of chlorotrimethyl silane with external cooling with ice bath and stirring. After 30 minutes, 15.6 mL of benzoyl chloride (134.3 mmols) was added and the ice bath was removed. After 2 hours the reaction mixture was again cooled in an ice bath and 55 mL of ice-cold water was added. After 15 minutes of stirring, 55 mL of conc. $NH_4OH$ was added. After an additional 30 minutes the reaction mixture was evaporated to an oil on a rotoevaporator and dissolved in 300 mL $CH_2Cl_2$ and extracted with saturated $NaHCO_3$ solution (2×100 mL). The organic layer was dried and loaded into a silica gel (750 grams) and eluted with 7:3 ethyl acetate:hexane to give 18.3 g (25.10 mmol) of benzoylated 2' and 3' isomeric mixture 95.1% yield.

EXAMPLE 46

N-Benzoyl-5'-O-(dimethoxytrityl)-2'-O-
{6-[(triphenylmethyl) thio]hexyl}adenosine and
N-Benzoyl-5'-O-(dimethoxytrityl)-
3'-O-{6-[(triphenylmethyl)thio]hexyl}adenosine.

The base protected nucleoside mixture from Example 45 was coevaporated with 2×100 mL of anhydrous pyridine. The resultant material was redissolved in 100 mL of anhydrous pyridine and with stirring, 13.9 g (41.0 retool) dimethoxytritylchloride was added. The reaction mixture was stirred for 1.5 hours, after which thin layer chromatography (TLC; hexane :ethyl acetate (EtOAc) , 1:1) showed disappearance of starting material. Methanol (20 mL) was added and the reaction was stirred for 30 minutes. Pyridine was evaporated and the residue was coevaporated once with 200 mL of toluene. The resultant residue was dissolved in 100 mL of $CH_2Cl_2$ and applied to a silica gel column (1000 g, packed in hexane). The column was eluted with the following solvents: 100% Hexane (1 L); 45:55 EtOAc-hexane (3 L) 50:50 EtOAc-hexane (3L) and 55:45 EtOAc-hexane until all 2'-O-isomer was eluted out. Then it was eluted with 60:40 EtOAc:Hexane 2 liter followed by 70:30 EtOAc:Hexane until all 3'-O-isomer is off the column. The isolated yields (56% combined yield) were: 10.3 g [2' isomer; 2.4 g (3'-isomer) and 1.9 g (2'+3' isomeric mixture). $R_f$=0.28 for 2'-isomer in hexane:EtOAc 1:1 and $R_f$=0.13 for 3'-isomer in the same solvent system.

EXAMPLE 47

Adenosine-N-benzoyl-5'-O-[bis
(4-methoxyphenyl)-O-phenyl-methyl]-2'-O-
{6-[(triphenylmethyl)thio]hexyl}-3'-[2-cyanoethyl
bis (1-methylethyl)phosphoramidite]

The nucleoside N-benzoyl-5'-O-[dimethoxytrityl]- 2' -O-[6-[(triphenylmethyl)thio]hexyl] adenosine from Example 46 (4.6 g, 4.46 mMol) was dissolved in 60 mL $CH_2Cl_2$ anhydrous. Diisopropylamine tetrazolide salt (0.4 g, 2.23 mmol) was added followed by phosphitylation reagent. The reaction mixture was stirred overnight. TLC analysis (1:1 EtOAc:Hexane) showed completion (>95%) of the reaction. Then the mixture was transferred into 100 mL of saturated $NaHCO_3$ in a separatory funnel. The reaction was washed with 100 mL $CH_2Cl_2$ containing 1% $Et_3N$. The organic layer was washed with 100 mL of saturated NaCl solution, dried over anhydrous sodium sulfate and evaporated to give 6.75 g of the crude product. It was then purified in a silica column (200 g, in a 25 cm×7.5 cm column) packed in 50:50 EtOAc:hexane containing 0.1% $Et_3N$. The column was eluted with the same solvent followed by 60:40 EtOAc: hexane to give the product as a colorless foam. (4.38 g, 3.6 mmol, 81% yield). $^{31}$P NMR ($CDCl_3$): 150.6, 151.4 ppm (d).

EXAMPLE 48

Controlled Pore Glass (CPG) Attached To The
Nucleoside of Example 46.

Succinylated CPG, prepared according to Damha, et al., Nucleic Acids Res. 1990, 18, 3813, (0.3 g, with a loading of approximately 80 micromoles/g, dried under vacuum for 3 hours immediately before use) was added to 3 ml anhydrous pyridine in a 50 ml round-bottom flask. 1-(3-dimethylaminopropyl)- 3-ethylcarbodiimide (0.12 g, 0.63 mmol), triethylamine (25 ml, distilled over $CaH_2$), dimethylaminopryidine (0.005 g, 0.03 mmol) and the 2' nucleoside of Example 46 (0.21 g, 0.203 mmol) were added under Ar and the mixture shaken mechanically for 19 hours. More nucleoside (0.025 g, 0.025 mmol) was added and the mixture shaken an additional 5.5 hours Pentachlorophenol (0.045 g, 0.17 mmol) was added and the mixture shaken 18 hours. CPG was filtered off and washed successively with dichloromethane, triethylamine, and dichloromethane. CPG was then dried under vacuum, suspended in 15 ml piperidine and shaken 30 min. The product, nucleoside-CPG, was filtered off, washed thoroughly with dichloromethane and again dried under vacuum. Extent of loading (determined by spectrophotometric assay of dimethoxytrityl cation in 0.3M p-toluenesulfonic acid at 498 nm) was approximately 30 mmol/g.

EXAMPLE 49

Synthesis of Oligonucleotide

Oligomer 35: GAC UA*G AUC UGA GCC UGG GAG CUC UCU A*GU C (SEQ ID NO: 14) (P=O, 2'-OMe ribonucleotide decoy, represents TAR sequence 16 to 46; A*=2'-O-hexyl-S-trityl-mercapto-adenosine)

A 0.15M solution of the 2'-O-hexyl-S-tritylmercapto modified amidite in anhydrous $CH_3CN$ is used in a 380B ABI DNA synthesizer to synthesize oligonucleotides. During the phosphodiester synthesis, oxidation of the tervalent phosphorous is achieved using a 0.5M solution of tert-butylhydroperoxide in $CH_3CN$ since the tritylthioether group is sensitive to iodine/water solution. A coupling efficiency of >90% is observed during the modified amidite coupling after extending the coupling time to 15 minutes. The modified nucleoside incorporation is shown in asterisked places. The 2'-OMe phosphoramidites and controlled pore glass support having the cytosine were purchased from Sterling Research, Sterling, Va. The oligonucleotide is synthesized in a 10 μmol scale in the "Trityl-On" mode. Standard deprotection conditions (30% $NH_4OH$, 55° C., 16 hr) are employed. HPLC is performed on a Waters 600E instrument equipped with a model 991 detector. For preparative purposes, the following reverse phase HPLC conditions are employed: Waters Delta Pak Waters Delta-Pak $C_4$ 15 μm, 300A, 25×100 mm column equipped with a guard column of the same material; column flow rate: 5 ml/min; gradient: 5% B for the first 10 minutes, linear 1% increase for every minute thereafter. Following HPLC purification, the oligonucleotide is detritylated and further purified by size exclusion using a Sephadex G-25 column.

The purified oligonucleotide is treated with 0.1M $AgNO_3$ in TEAA buffer followed by DTT treatment to generate a free thiol group (see Manoharan et al., *Bioorganic & Medicinal Chemistry Letters*, 1993, 3, 2765). The resulting compound was aerobically dialyzed to form a disulfide bond between the 2'-O-tethers from the asterisked adenosines. HPLC analysis revealed complete conversion to new, covalently crosslinked species.

Binding assays with tat protein shows that the crosslinked TAR binds better than the native TAR sequence.

EXAMPLE 50

Crosslinked Circular Oligonucleotide Synthesis
Using the CPG Bound Oligonucleotide.

Oligomer 36 5' UA* CCA GAU CUG AGC CU GGG AGC UCU CUG GUA* 3' (SEQ ID NO: 15) (P=O, 2'-OMe ribonucleotide decoy, represents TAR sequence 16 to 46);

A*=2'-O-hexyl-S-tritylmercapto-adenosine)

The 2'-O-hexyl-S-tritylmercapto modified amidite in anhydrous $CH_3CN$ is used in a 380B ABI DNA synthesizer to synthesize the oligonucleotide. Modified adenosine CPG was used to incorporate the 3' terminal. During the nucleotide synthesis, oxidation of the tervalent phosphorous is effected using a 0.5M solution of tert-butylhydroperoxide in $CH_3CN$ since the tritylthioether group is sensitive to iodine/water solution. A coupling efficiency of >90% is observed during the modified amidite and modified CPG coupling steps after extending the coupling time to 15 minutes. The modified nucleoside incorporation is shown in asterisked places. The 2'-OMe phosphoramidites were purchased from Sterling Research, Sterling, Va. The oligonucleotide is synthesized in a 10 μmol scale in the "Trityl-On" mode. Standard deprotection conditions (30% $NH_4OH$, 55° C., 16 hr) are employed. HPLC is performed on a Waters 600E instrument equipped with a model 991 detector. For preparative purposes, the following reverse phase HPLC conditions are employed: Waters Delta Pak Waters Delta-Pak $C_4$ 15 μm, 300A, 25×100 mm column equipped with a guard column of the same material; column flow rate: 5 ml/min; gradient: 5% B for the first 10 minutes, linear 1% increase for every minute thereafter. Following HPLC purification, the oligonucleotide is detritylated and further purified by size exclusion using a Sephadex G-25 column.

The purified oligonucleotide is treated with 0.1M $AgNO_3$ in TEAA buffer followed by DTT treatment to generate a free thiol group (See Manoharan et al., *Bioorganic & Medicinal Chemistry Letters*, 1993, 3, 2765). The compound was aerobically dialyzed to form a disulfide bond between the 2'-O-tethers from the asterisked adenosines. HPLC analysis revealed complete conversion to new, covalently crosslinked species.

Binding assays with tat protein shows that the crosslinked TAR binds better than the native TAR sequence. This is used to identify the tat protein as per the below Procedures.

EVALUATION

PROCEDURE 1—Nuclease Resistance

A. Evaluation of the Resistance of Cross-linked Oligonucleotides to Serum and Cytoplasmic Nucleases Cross-linked oligonucleotides of the invention can be assessed for their resistance to serum nucleases by incubation of the cross-linked oligonucleotide in media containing various concentrations of fetal calf serum or adult human serum. Labeled cross-linked oligonucleotides are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the cross-linked oligonucleotide it is possible to determine the effect on nuclease degradation by the particular modification. For the cytoplasmic nucleases, an HL-60 cell line can be used. A post-mitochondrial supernatant is prepared by differential centrifugation and the labelled cross-linked oligonucleotides are incubated in this supernatant for various times. Following the incubation, the cross-linked oligonucleotides are assessed for degradation as outlined above for serum nucleolytic degradation. Autoradiography results are quantitated for comparison of the unmodified and the cross-linked oligonucleotides of the invention. It is expected that the cross-linked oligonucleotides will be completely resistant to serum and cytoplasmic nucleases.

B. Evaluation of the Resistance of Cross-Linked Oligonucleotides to Specific Endo- and Exo-Nucleases Evaluation of the resistance of natural oligonucleotides and cross-linked oligonucleotides of the invention to specific nucleases (i.e., endonucleases, 3',5'-exo-, and 5',3'-exonucleases) can be done to determine the exact effect of the modified linkage on degradation. The cross-linked oligonucleotides are incubated in defined reaction buffers specific for various selected nucleases. Following treatment of the products with protease K, urea is added and analysis on 20% polyacrylamide gels containing urea is done. Gel products are visualized by staining with Stains All reagent (Sigma Chemical Co.). Laser densitometry is used to quantitate the extent of degradation. The effects of the modified linkage are determined for specific nucleases and compared with the results obtained from the serum and cytoplasmic systems. As with the serum and cytoplasmic nucleases, it is expected that the cross-linked oligonucleotides of the invention will be completely resistant to endo- and exo-nucleases.

PROCEDURE 2—5-Lipoxygenase Analysis and Assays

A. Therapeutics

For therapeutic use, an animal suspected of having a disease characterized by excessive or abnormal supply of 5-lipoxygenase is treated by administering cross-linked oligonucleotides in accordance with this invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The cross-linked oligonucleotides of this invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 μg of total RNA in a buffer consisting, for example, of 50 mm phosphate, pH ranging from about 4–10 at a temperature from about 30° to about 50° C. The cleaved 5-lipoxygenase RNA can be analyzed by agarose gel electrophoresis and hybridization with radiolabeled DNA probes or by other standard methods.

C. Diagnostics

The cross-linked oligonucleotides of this invention will also be useful in diagnostic applications, particularly for the determination of the expression of specific mRNA species in various tissues or the expression of abnormal or mutant RNA species. In this example, the cross-linked oligonucleotides target a hypothetical abnormal mRNA by being designed complementary to the abnormal sequence, but would not hybridize to normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte-like cell or neutrophil-like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (downstream products of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of cross-linked oligonucleotides which interfere with 5-lipoxygenase synthesis in these cells.

A second test system for cross-linked oligonucleotides makes use of the fact that 5-lipoxygenase is a "suicide" enzyme in that it inactivates itself upon reacting with substrate. Treatment of differentiated HL-60 or other cells expressing 5-lipoxygenase, with 10 μM A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Cross-linked oligonucleotides directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

The most direct effect which cross-linked oligonucleotides can exert on intact cells and which can be easily quantitated is specific inhibition of 5-lipoxygenase protein synthesis. To perform this technique, cells can be labelled with $^{35}$S-methionine (50 μCi/mL) for 2 hours at 37° C. to label newly synthesized protein. Cells are extracted to solubilize total cellular proteins and 5-lipoxygenase is immunoprecipitated with 5-lipoxygenase antibody followed by elution from protein A-Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 μM, 10 μM, and 30 μM of effective cross-linked oligonucleotides for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 μM $^{14}$C-arachidonic acid, 2mM ATP, 50 μM free calcium, 100 μg/ml phosphatidylcholine, and 50 mM bis-Tris buffer, pH 7.0, for 5 min at 37° C. The reactions are quenched by the addition of an equal volume of acetone, and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective cross-linked oligonucleotides at 1 μM, 10 μM, and 30 μM would be as follows. Control cells oxidize 200 pmol arachidonic acid/5 min/$10^6$ cells. Cells treated with 1 μM, 10 μM, and 30 μM of an effective cross-linked oligonucleotides would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 4° C. The wells are blocked for 90 min with 5% goat serum diluted in 20 mM Tris-HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 μL in the microtiter wells for 90 min. The antibodies are prepared by immunizing rabbits with purified human recombinant 5-lipoxygenase. The wells are washed with TBS containing 0.05% Tween 20 (TBST), then incubated with 100 μL of a 1:1000 dilution of peroxidase conjugated goat anti-rabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30-mer cross-linked oligonucleotide at 1 μM, 10 μM, and 30 μM would be 30 ng, 18 ng and 5 ng of 5-lipoxygenase per $10^6$ cells, respectively, with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 (LTB4) upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into neutrophil-like cells. Cells (2×$10^5$ cells/mL) will be treated with increasing concentrations of cross-linked oligonucleotides for 48–72 hours in the presence of 1.3% DMSO. The cells are washed and resuspended at a concentration of 2×$10^6$ cell/mL in Dulbecco's phosphate buffered saline containing 1% delipidated bovine serum albumin. Cells are stimulated with 10 μM calcium ionophore A23187 for 15 min and the quantity of LTB4 produced from $5 \times 10^5$ cells determined by radioimmunoassay as described by the manufacturer.

Using this assay the following results would likely be obtained with a cross-linked oligonucleotide directed to the 5-lipoxygenase mRNA. Cells will be treated for 72 hours with either 1 μM, 10 μM or 30 μM cross-linked oligonucleotide in the presence of 1.3% DMSO. The quantity of $LTB_4$ produced from $5 \times 10^5$ cells would be expected to be about 75 pg, 50 pg, and 35 pg, respectively with untreated differentiated cells producing 75 pg $LTB_4$.

E. In Vivo Assay

Inhibition of the production of 5-lipoxygenase in the mouse can be demonstrated in accordance with the following protocol. Topical application of arachidonic acid results in the rapid production of leukotriene $B_4$, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Crosslinked oligonucleotides will be applied topically to both ears 12 to 24 hours prior to administration of arachidonic acid to allow optimal activity of the compounds. Both ears are pretreated for 24 hours with either 0.1 μmol, 0.3 μmol, or 1.0 μmol of the oligonucleotide prior to challenge with arachidonic acid. Values are expressed as the mean for three animals per concentration. Inhibition of polymorphonuclear cell infiltration for 0.1 μmol, 0.3 μmol, and 1 μmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

PROCEDURE 3

Crosslinked Oligonucleotides Having 2'- to 1'- Linkages in the Binding Domain of HPV-11 DNA Targeted Against E2 Protein and Use to Identify the E2 protein:

Interstrand Crosslink Synthesis From a Palindromic Sequence

The E2 protein is an essential viral enhancer factor that binds as a dimer to a specific HPV DNA sequence which is capable of activating transcription in vivo. (Hegde et al., Nature, 359, 505, 1992; Dartmann et al., Virology, 151, 124–130, 1986). The main binding recognition element is a 12-bp element ACCGNNNNCGGT.

Synthesis of Oligonucleotide:

Oligomer 37 with sequence: 5' CCG A*AC CGA CGT CGG T(dU) C GC 3' (SEQ ID NO: 16)
is synthesized on a 10 micromole scale using 5'-dimethoxytrityl- 2'-O-(pentyl-N-phthalimido)-2'-deoxyadenosine phosphoramidite at A* and deoxyuridine phosphoramidite at dU site. After deprotection and standard purification protocols, the oligonucleotide is treated with uracil-DNA glycosylase. After quantitative uracil release, which is checked by analytical HPLC, the oligonucleotide is lyophilized, dissolved in NaOAc buffer, (pH 5.0). and reductive amination is carried out with 6M $NaCNBH_3$ in 250 mM NaOAc pH 5.0. The reaction is left to stand overnight. The reaction mixture is desalted, analytical HPLC is used to follow the formation of the crosslink between the nucleophilic pentyl amine and electrophilic abasic site. The crosslinked product is purified by preparative reverse phase HPLC followed by PAGE.

The presence of the $E_2$ protein is analyzed by gel shift. Assays are performed between 5'-$^{32}$P-radiolabeled crosslinked oligonucleotide and HPV E2 protein and also between the wildtype DNA and E2 protein.

PROCEDURE 4

Crosslinked Oligonucleotides Having 2'- to 2'- Linkages in the the Binding Domain of HIV RRE Targeted Against Rev Protein:

Intrastrand Crosslink Synthesis Within an RNA Selected by Combinatorial Approaches The RNA oligonucleotide described as RBE3 by Bartel ibid; is modified as follows:

Oligomer 38 5' GGU* GGG CGC AGC UUC GGC UGA CGG UAC A*CC 3' (SEQ ID NO: 17) (2'-OMe RNA analog of RBE3 variant of RRE; P=O; U*=2'-O-hexenyl-uridine; A*=2'-O-pentylaminoadenosine)

The oligonucleotide is synthesized at a 10 micromole scale. The appropriate 2'-O-modified phosphoramidites are used. A 0.2M solution of each amidite is used and a 10 min wait step is introduced after coupling at the modified amidite coupling. The oligonucleotide, after standard purification, is subjected to the following sequence of events to synthesize crosslinked oligonucleotides: a) the oligonucleotide is dissolved in water and treated with NMMO, $OsO_4$ and sodium periodate to generate the aldehyde from the olefin; b) it is then purified in a Sephadex G-25 column to give the purified aldehyde linker containing oligonucleotide; c) the oligonucleotide is lyophilized, dissolved in NaOAc buffer, pH 5.0. and reductive amination is carried out with 6M $NaCNBH_3$ in 250 mM NaOAc pH 5.0; d) after leaving the reaction overnight, the reaction mixture is desalted; f) analytical HPLC is used to follow the formation of the crosslink between the nucleophilic and electrophilic arms; and g) the crosslinked product is purified by preparative reverse phase HPLC.

The in vivo activity of the RRE crosslinked derivative is measured against rev utilizing a binding assay.

PROCEDURE 5

Bioaffinity Isolation and Diagnostics of Tat Protein Mediated by the Crosslinked TAR Element Having a Reporter Group Oligomer 39 GAC UA*G AUC UGA GCC UGG GAG CUC UCU A*GU C-Biotin (SEQ ID NO: 14) (P=O, 2'-F ribonucleotide decoy, represents TAR sequence 16 to 46; A*=2'-O-hexyl-S-trityl-mercapto-adenosine)

This oligonucleotide is synthesized similar to the procedure described in Example 49 with the following modifications: i) a biotin attached CPG column available from Sterling Chemicals, Sterling, Va., and ii) 2'-F containing amidites are used. The oligonucleotide is synthesized, purified and crosslinked as described in Examples. The crosslinked oligo is mixed with the HIV-1 isolate from the biological sample of interest. Tat protein alone binds specifically with the oligonucleotide. The protein-crosslinked RNA conjugate is pulled out by a Sterptavidin-Agarose column and the conjugate is further purified FPLC using a Mono-Q column from the crosslinked RNA conjugate. The purified conjugate is detected by Streptavidin-Alkaline phosphatase chromogenic system.

PROCEDURE 6

Bioaffinity Isolation and Diagnostics of Tat Protein Mediated by the Crosslinked TAR Element Attached to a Chromatographic Column Oligomer 40 Aminolinker-GAC UA*G AUC UGA GCC UGG GAG CUC UCU A*GU C (P=O, 2'-F ribonucleotide decoy, represents TAR sequence 16 to 46; A* =2'-O-hexyl-S-trityl-mercapto-adenosine)

This oligonucleotide is synthesized using a procedure similar to that of Procedure 5 with the following modifications: i) an aminolinker phosphoramidite available from Sterling Chemicals, Sterling, Va. is used at the 5'-end; and ii) 2'-F containing amidites are used. The oligonucleotide is synthesized, purified and crosslinked as previously described. The crosslinked oligo is coupled to a Sepharose or Agarose column by periodate oxidation of the matrix, washing of the periodate, reductive amination with the crosslink via the 5'-aminolinker. The modified chromatographic column is treated with the HIV-1 isolate from the patients. Tat protein alone binds specifically with the oligonucleotide column. A high salt elution is used to release the tat protein-crosslinked RNA conjugate. The purified conjugate is detected for tat by a standard antibody or non-antibody chromogenic systems.

---

What is claimed is:

1. A cross-linked nucleic acid comprising:
   a first nucleotide located on a first oligonucleotide strand;
   a first bond means located on a sugar moiety of said first nucleotide;
   a second nucleotide located on a second oligonucleotide strand;
   a second bond means located on a sugar moiety of said second nucleotide; and
   a covalent cross-linkage between said first and said second bond means, provided that at least one of the first and second bond means is located at a non-terminal nucleotide and further provided that said cross-linkage:
   is not between the 3' carbon of a sugar moiety of said first nucleotide and the 5' carbon of a sugar moiety of said second nucleotide;
   is not between the 3' carbon of a sugar moiety of said second nucleotide and the 5' carbon of a sugar moiety of said first nucleotide; and
   does not include a nucleosidic base.

2. A cross-linked nucleic acid comprising:
   a first nucleotide located on an oligonucleotide strand;
   a first bond means located on a sugar moiety of said first nucleotide;
   a second nucleotide located on said oligonucleotide strand;
   a second bond means located on a sugar moiety of said second nucleotide; and
   a covalent cross-linkage between said first and said second bond means, provided that at least one of the first and second bond means is located at a non-terminal nucleotide and further provided that said cross-linkage:
   is not between the 3' carbon of a sugar moiety of said first nucleotide and the 5' carbon of a sugar moiety of said second nucleotide;
   is not between the 3' carbon of a sugar moiety of said second nucleotide and the 5' carbon of a sugar moiety of said first nucleotide; and
   does not include a nucleosidic base.

3. A cross-linked nucleic acid comprising:
   a first nucleotide located on a 3' end of a first oligonucleotide strand, said first nucleotide including a 2',3'-dialdehyde structure;
   a second nucleotide located on a second oligonucleotide strand or on said first oligonucleotide strand;
   a space-spanning group located on a sugar moiety of said second nucleotide; and
   a covalent cross-linkage between said dialdehyde structure and said space-spanning group, provided that said cross-linkage does not include a nucleosidic base.

4. A cross-linked nucleic acid comprising:
   a first nucleotide located on a 3' end of a first oligonucleotide strand, said first nucleotide including 2' and 3' hydroxyl groups;
   a second nucleotide located on a second oligonucleotide strand or on said first oligonucleotide strand;
   a space-spanning group located on a sugar moiety of said second specific nucleotide; and
   a covalent acetal cross-linkage between said 2' and 3' hydroxyl groups and said space-spanning group, provided that said cross-linkage does not include a nucleosidic base.

5. A cross-linked nucleic acid comprising:
   a first nucleotide located on a first oligonucleotide strand;
   a first bond means located on a sugar moiety of said first nucleotide;
   a second nucleotide located on a second oligonucleotide strand or on said first oligonucleotide strand;
   a second bond means located on said second nucleotide; and a covalent cross-linkage between said first and said second bond means, provided that at least one of the first and second bond means is located at a non-terminal nucleotide and further provided that said cross-linkage:
is not between the 3' carbon of a sugar moiety of said first nucleotide and the 5' carbon of a sugar moiety of said second nucleotide;
is not between the 3' carbon of a sugar moiety of said second nucleotide and the 5' carbon of a sugar moiety of said first nucleotide; and
does not include a nucleosidic base.

6. The cross-linked nucleic acid of claim 5 wherein:
said first nucleotide is located in a first nucleotide sequence and said second nucleotide is located in a second nucleotide sequence;
said second nucleotide sequence is complementary to and hybridizable with said first nucleotide sequence; and
said first and said second nucleotide sequences are located on a single strand of said oligonucleotide and said first and second nucleotide sequences are hybridized with one another.

7. The cross-linked nucleic acid of claim 5 wherein:
said first nucleotide is located in a first nucleotide sequence and said second nucleotide is located in a second nucleotide sequence;
said second nucleotide sequence is complementary to and specifically hybridizable with said first nucleotide sequence; and
said first and said second nucleotide sequences are located on different oligonucleotide strands.

8. The cross-linked nucleic acid of claim 5 wherein:
said first bond means of said cross-linkage includes an abasic site; and
said second bond means of said cross-linkage includes a space-spanning group covalently bonded with said abasic site.

9. The cross-linked nucleic acid of claim 8 wherein said abasic site includes an aldehyde covalently bonded with said space-spanning group.

10. The cross-linked nucleic acid of claim 8 wherein said space-spanning group includes a group that is an amine, hydrazine, hydroxylamine, semicarbazide, thiosemicarbazide, hydrazone, hydrazide, alcohol or thiol.

11. The cross-linked nucleic acid of claim 10 wherein said space-spanning group includes an amine.

12. The cross-linked nucleic acid of claim 8 wherein said space-spanning group is attached to the 2'-position of said second nucleotide.

13. The cross-linked nucleic acid of claim 8 wherein said space-spanning group is $C_1$–$C_{20}$ straight chain alkyl, $C_1$–$C_{20}$ straight chain O-alkyl, $C_1$–$C_{20}$ straight chain S-alkyl, $C_1$–$C_{20}$ straight chain NH-alkyl, $C_1$–$C_{20}$ straight chain substituted alkyl, $C_1$–$C_{20}$ straight chain substituted O-alkyl, $C_1$–$C_{20}$ straight chain substituted S-alkyl, $C_1$–$C_{20}$ straight chain substituted NH-alkyl, $C_3$–$C_{50}$ branched chain alkyl, $C_3$–$C_{50}$ branched chain O-alkyl, $C_3$–$C_{50}$ branched chain S-alkyl, $C_3$–$C_{50}$ branched chain NH-alkyl, $C_3$–$C_{50}$ branched chain substituted alkyl, $C_3$–$C_{50}$ branched chain substituted O-alkyl, $C_3$–$C_{50}$ branched chain substituted S-alkyl, $C_3$–$C_{50}$ branched chain substituted NH-alkyl, $C_2$–$C_{20}$ straight chain alkenyl, $C_2$–$C_{20}$ straight chain O-alkenyl, $C_2$–$C_{20}$ straight chain S-alkenyl, $C_2$–$C_{20}$ straight chain NH-alkenyl, $C_2$–$C_{20}$ straight chain substituted alkenyl, $C_2$–$C_{20}$ straight chain substituted O-alkenyl, $C_2$–$C_{20}$ straight chain substituted S-alkenyl, $C_2$–$C_{20}$ straight chain substituted NH-alkenyl, $C_3$–$C_{50}$ branched chain alkenyl, $C_3$–$C_{50}$ branched chain O-alkenyl, $C_3$–$C_{50}$ branched chain S-alkenyl, $C_3$–$C_{50}$ branched chain NH-alkenyl, $C_3$–$C_{50}$ branched chain substituted alkenyl, $C_3$–$C_{50}$ branched chain substituted O-alkenyl, $C_3$–$C_{50}$ branched chain substituted S-alkenyl, $C_3$–$C_{50}$ branched chain substituted NH-alkenyl, $C_2$–$C_{20}$ straight chain alkyne, $C_2$–$C_{20}$ straight chain O-alkyne, $C_2$–$C_{20}$ straight chain S-alkyne, $C_2$–$C_{20}$ straight chain NH-alkyne, $C_2$–$C_{20}$ straight chain substituted alkyne, $C_2$–$C_{20}$ straight chain substituted O-alkyne, $C_2$–$C_{20}$ straight chain substituted S-alkyne, $C_2$–$C_{20}$ straight chain substituted NH-alkyne, $C_3$–$C_{50}$ branched chain alkyne, $C_3$–$C_{50}$ branched chain O-alkyne, $C_3$–$C_{50}$ branched chain S-alkyne, $C_3$–$C_{50}$ branched chain NH-alkyne, $C_3$–$C_{50}$ branched chain substituted alkyne, $C_3$–$C_{50}$ branched chain substituted O-alkyne, $C_3$–$C_{50}$ branched chain substituted S-alkyne, $C_3$–$C_{50}$ branched chain substituted NH-alkyne, polyamine, polyamide, polyester, polyethylene glycol, aryl, aralkyl or heterocyclic.

14. The cross-linked nucleic acid of claim 13 wherein said space-spanning group is from 8 to 13 atoms in length.

15. The cross-linked nucleic acid of claim 5 wherein:
said first bond means includes a first space-spanning group;
said second bond means of said cross-linkage includes a second space-spanning group; and
said covalent cross-linkage is between said first and said second space-spanning groups.

16. The cross-linked nucleic acid of claim 15 wherein said first space-spanning group is an aldehyde.

17. The cross-linked nucleic acid of claim 16 wherein said first space-spanning group is C-formyl, o-methylaminobenzenethiol, aryl substituted imidazolidino, dithiane, bis(p-nitrophenoxy), acetal, nitrile, ester or alcohol.

18. The cross-linked nucleic acid of claim 15 wherein said second space-spanning group is an amine, hydrazine, hydroxylamine, semicarbazide, thiosemicarbazide, hydrazide, alcohol or thiol.

19. The cross-linked nucleic acid of claim 15 wherein:
said first space-spanning group is attached to the 2'-position of said first nucleotide; and
said second space-spanning group is attached to the 2'-position of said second nucleotide.

20. The cross-linked nucleic acid of claim 15 wherein each of said first and second space-spanning groups are, independently, $C_1$–$C_{20}$ straight chain alkyl, $C_1$–$C_{20}$ straight chain O-alkyl, $C_1$–$C_{20}$ straight chain S-alkyl, $C_1$–$C_{20}$ straight chain NH-alkyl, $C_1$–$C_{20}$ straight chain substituted alkyl, $C_1$–$C_{20}$ straight chain substituted O-alkyl, $C_1$–$C_{20}$ straight chain substituted S-alkyl, $C_1$–$C_{20}$ straight chain substituted NH-alkyl, $C_3$–$C_{50}$ branched chain alkyl, $C_3$–$C_{50}$ branched chain O-alkyl, $C_3$–$C_{50}$ branched chain S-alkyl, $C_3$–$C_{50}$ branched chain NH-alkyl, $C_3$–$C_{50}$ branched chain substituted, alkyl, $C_3$–$C_{50}$ branched chain substituted O-alkyl, $C_3$–$C_{50}$ branched chain substituted S-alkyl, $C_3$–$C_{50}$ branched chain substituted NH-alkyl, $C_2$–$C_{50}$ straight chain alkenyl, $C_2$–$C_{20}$ straight chain O-alkenyl, $C_2$–$C_{20}$ straight chain S-alkenyl, $C_2$–$C_{20}$ straight chain NH-alkenyl, $C_2$–$C_{20}$ straight chain substituted alkenyl, $C_2$–$C_{20}$ straight chain substituted O-alkenyl, $C_2$–$C_{20}$ straight chain substituted S-alkenyl, $C_2$–$C_{20}$ straight chain substituted NH-alkenyl, $C_3$–$C_{50}$ branched chain alkenyl, $C_3$–$C_{50}$ branched chain O-alkenyl, $C_3$–$C_{50}$ branched chain S-alkenyl, $C_3$–$C_{50}$ branched chain NH-alkenyl, $C_3$–$C_{50}$ branched chain substituted alkenyl, $C_3$–$C_{50}$ branched chain substituted O-alkenyl, $C_3$–$C_{50}$ branched chain substituted S-alkenyl, $C_3$–$C_{50}$ branched chain substituted NH-alkenyl, $C_2$–$C_{20}$ straight chain alkyne, $C_2$–$C_{20}$ straight chain O-alkyne, $C_2$–$C_{20}$ straight chain S-alkyne, $C_2$–$C_{20}$ straight chain NH-alkyne, $C_2$–$C_{20}$ straight chain substituted alkyne, $C_2$–$C_{20}$ straight chain substituted O-alkyne, $C_2$–$C_{20}$ straight chain substituted S-alkyne, $C_2$–$C_{20}$ straight chain substituted NH-alkyne, $C_3$–$C_{50}$ branched chain alkyne, $C_2$–$C_{50}$ branched chain O-alkyne, $C_3$–$C_{50}$ branched chain S-alkyne, $C_3$–$C_{50}$ branched chain NH-alkyne, $C_3$–$C_{50}$ branched chain substituted alkyne, $C_3$–$C_{50}$ branched chain substituted O-alkyne, $C_3$–$C_{50}$ branched chain substituted S-alkyne, $C_3$–$C_{50}$ branched chain substituted NH-alkyne, polyamine, polyamide, polyester, polyethylene glycol, aryl, aralkyl or heterocyclic.

21. The cross-linked nucleic acid of claim 15 wherein said first and second space-spanning groups are thiol groups and said covalent cross-linkage is a disulfide bond.

22. The cross-linked nucleic acid of claim 5 wherein:

said first nucleotide is located in a first nucleotide sequence and said second nucleotide is located in a second nucleotide sequence; and said first and said second nucleotide sequences are located on a single strand of an oligonucleotide with said second nucleotide sequence located on said oligonucleotide at a non-hybridizable position with respect to said first nucleotide sequence and at a distance from said first nucleotide sequence sufficient to allow said oligonucleotide to assume a conformation wherein said first and second nucleotide sequences are located in spatial proximity with each other.

23. The cross-linked nucleic acid of claim 5 wherein:

said first bond means includes a 3'-terminal nucleoside having a 2',3'-dialdehyde structure;

said second bond means includes a space-spanning group; and said active functional group is reacted with a dialdehyde.

24. The cross-linked nucleic acid of claim 5 wherein:

said first bond means includes a 3'-terminal nucleotide having 2' and 3'-sugar hydroxyl groups;

said second bond means includes a space-spanning group; and an acetal cross-linkage connects said 2' and 3' hydroxyl groups and said space-spanning group.

25. The cross-linked nucleic acid of claim 1 wherein:

said first nucleotide is covalently bound to at least two nucleotides on said first oligonucleotide strand; and said second nucleotide is covalently bound to at least two nucleotides on said second oligonucleotide strand.

26. The cross-linked nucleic acid of claim 2 wherein:

said first nucleotide is covalently bound to at least two nucleotides on said oligonucleotide strand; and said second nucleotide is covalently bound to at least a third nucleotide and a fourth nucleotide on said oligonucleotide strand, said third and fourth nucleotides being different from said first nucleotide.

27. The cross-linked nucleic acid of claim 5 wherein:

said first nucleotide is covalently bound to at least two nucleotides on said first oligonucleotide strand; and said second nucleotide is covalently bound to at least a third nucleotide and a fourth nucleotide on said second oligonucleotide strand or on said first oligonucleotide strand, said third and fourth nucleotides being different from said first nucleotide.

28. A cross-linked oligonucleotide comprising:

a first sequence region in an oligonucleotide;

a second sequence region in an oligonucleotide;

an abasic site located in said first sequence region; and a space-spanning group located on said second sequence region and covalently bonded with said abasic site, provided that said covalent bond does include a nucleosidic base.

29. The cross-linked oligonucleotide of claim 28 wherein said first sequence region and said second sequence region are on a single oligonucleotide strand.

30. The cross-linked oligonucleotide of claim 28 wherein said first sequence region and said second sequence region are on different oligonucleotide strands.

31. The cross-linked oligonucleotide of claim 28 wherein said first sequence region and said second sequence region are complementary to and specifically hybridizable with one another.

32. The cross-linked oligonucleotide of claim 28 wherein said space-spanning group is $C_1$–$C_{20}$ straight chain alkyl, $C_1$–$C_{20}$ straight chain O-alkyl, $C_1$–$C_{20}$ straight chain S-alkyl, $C_1$–$C_{20}$ straight chain NH-alkyl, $C_1$–$C_{20}$ straight chain substituted alkyl, $C_1$–$C_{20}$ straight chain substituted O-alkyl, $C_1$–$C_{20}$ straight chain substituted S-alkyl, $C_1$–$C_{20}$ straight chain substituted NH-alkyl, $C_3$–$C_{50}$ branched chain alkyl, $C_3$–$C_{50}$ branched chain O-alkyl, $C_3$–$C_{50}$ branched chain S-alkyl, $C_3$–$C_{50}$ branched chain NH-alkyl, $C_3$–$C_{50}$ branched chain substituted alkyl, $C_3$–$C_{50}$ branched chain substituted O-alkyl, $C_3$–$C_{50}$ branched chain substituted S-alkyl, $C_3$–$C_{50}$ branched chain substituted NH-alkyl, $C_2$–$C_{20}$ straight chain alkenyl, $C_2$–$C_{20}$ straight chain O-alkenyl, $C_2$–$C_{20}$ straight chain S-alkenyl, $C_2$–$C_{20}$ straight chain NH-alkenyl, $C_2$–$C_{20}$ straight chain substituted alkenyl, $C_2$–$C_{20}$ straight chain substituted O-alkenyl, $C_2$–$C_{20}$ straight chain substituted S-alkenyl, $C_2$–$C_{20}$ straight chain substituted NH-alkenyl, $C_3$–$C_{50}$ branched chain alkenyl, $C_3$–$C_{50}$ branched chain O-alkenyl, $C_3$–$C_{50}$ branched chain S-alkenyl, $C_3$–$C_{50}$ branched chain NH-alkenyl, $C_3$–$C_{50}$ branched chain substituted alkenyl, $C_3$–$C_{50}$ branched chain substituted O-alkenyl, $C_3$–$C_{50}$ branched chain substituted S-alkenyl, $C_3$–$C_{50}$ branched chain substituted NH-alkenyl, $C_2$–$C_{20}$ straight chain alkyne, $C_2$–$C_{20}$ straight chain O-alkyne, $C_2$–$C_{20}$ straight chain S-alkyne, $C_2$–$C_{20}$ straight chain NH-alkyne, $C_2$–$C_{20}$ straight chain substituted alkyne, $C_2$–$C_{20}$ straight chain substituted O-alkyne, $C_2$–$C_{20}$ straight chain substituted S-alkyne, $C_2$–$C_{20}$ straight chain substituted NH-alkyne, $C_3$–$C_{50}$ branched chain alkyne, $C_2$–$C_{50}$ branched chain O-alkyne, $C_3$–$C_{50}$ branched chain S-alkyne, $C_3$–$C_{50}$ branched chain NH-alkyne, $C_3$–$C_{50}$ branched chain substituted alkyne, $C_3$–$C_{50}$ branched chain substituted O-alkyne, $C_3$–$C_{50}$ branched chain substituted S-alkyne, $C_3$–$C_{50}$ branched chain substituted NH-alkyne, polyamine, polyamide, polyester, polyethylene glycol, aryl, aralkyl or heterocyclic.

33. The cross-linked oligonucleotide of claim 28 wherein said space-spanning group includes an amine, hydrazine, semicarbazide, hydrazide, alcohol or thiol.

34. The cross-linked oligonucleotide of claim 28 wherein said space-spanning group is $CH_2$—$L_3$, O—$L_3$, S—$L_3$, NH—$L_3$ or CO—$L_3$ where $L_3$ is $C_1$–$C_{20}$ straight chain alkyl, $C_1$–$C_{20}$ straight chain substituted alkyl, $C_3$–$C_{50}$ branched chain alkyl, $C_3$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne, $C_3$–$C_{50}$ branched chain alkyne, $C_3$–$C_{50}$ branched chain substituted alkyne, polyamine, polyamide, polyester, polyethylene glycol, aryl, aralkyl or heterocyclic.

35. The cross-linked oligonucleotide of claim 28 wherein said space-spanning group is located on the 2'-position of a nucleotide within said second sequence region.

36. A cross-linked oligonucleotide comprising:

a first sequence region in an oligonucleotide;

a second sequence region in an oligonucleotide; and a covalently bonded linker of the structure:

$$X_1-L_1-Y-L_2-X_2$$

wherein $X_1$ is covalently connected to said first sequence region, $X_2$ is covalently connected to said second sequence region, and where:

(i)

$X_1$ and $X_2$, independently, are O, S, NH, CH$_2$ or CO;

$L_1$ and $L_2$, independently, are $C_1$–$C_{20}$ straight chain alkyl, $C_1$–$C_{20}$ straight chain substituted alkyl, $C_3$–$C_{50}$ branched chain alkyl, $C_3$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne, $C_3$–$C_{50}$ branched chain alkyne, $C_3$–$C_{50}$ branched chain substituted alkyne, polyamine, polyamide, polyester, polyethylene glycol, polyether, aryl, aralkyl or heterocyclic; and Y is an imine, amine, oxime, hydroxylamine, hydrazine, hydrazone, azine, hydrazide-hydrazone, amide, hydrazide, semicarbazide, semicarbazone, thiosemicarbazide, thiocarbazone, disulfide, hemiacetal, α-ketoalkylthioalkyl or α-keto-alkylaminoalkyl; or (ii)

$X_1$ and $X_2$, independently, are O or NH; and $L_1$—Y—$L_2$ together are NH—$L_3$—NH or NH—NH—$L_3$—NH—NH; and $L_3$ is $C_1$–$C_{20}$ straight chain alkyl, $C_1$–$C_{20}$ straight chain substituted alkyl, $C_3$–$C_{50}$ branched chain alkyl, $C_3$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne, $C_3$–$C_{50}$ branched chain alkyne, $C_3$–$C_{50}$ branched chain substituted alkyne, polyamine, polyamide, polyester, polyethylene glycol, polyether, aryl, aralkyl or heterocyclic; or (iii)

$X_1$ and $X_2$, independently, are O, S, NH, CH$_2$ or CO;

$L_1$ and $L_2$, independently, are $C_1$–$C_{20}$ straight chain alkylamino, $C_1$–$C_{20}$ straight chain substituted alkylamino, $C_3$–$C_{50}$ branched chain alkylamino, $C_3$–$C_{50}$ branched chain substituted alkylamino, $C_2$–$C_{20}$ straight chain alkenylamino, $C_2$–$C_{20}$ straight chain substituted alkenylamino, $C_3$–$C_{50}$ branched chain alkenylamino, $C_3$–$C_{50}$ branched chain substituted alkenylamino, $C_2$–$C_{20}$ straight chain alkynylamino, $C_2$–$C_{20}$ straight chain substituted alkynylamino, $C_3$–$C_{50}$ branched chain alkynylamino, $C_3$–$C_{50}$ branched chain substituted alkynylamino, $C_1$–$C_{20}$ straight chain alkylthio, $C_1$–$C_{20}$ straight chain substituted alkylthio, $C_3$–$C_{50}$ branched chain alkylthio, $C_3$–$C_{50}$ branched chain substituted alkylthio, $C_2$–$C_{20}$ straight chain alkenylthio, $C_2$–$C_{20}$ straight chain substituted alkenylthio, $C_3$–$C_{50}$ branched chain alkenylthio, $C_3$–$C_{50}$ branched chain substituted alkenylthio, $C_2$–$C_{20}$ straight chain alkynylthio, $C_2$–$C_{20}$ straight chain substituted alkynylthio, $C_3$–$C_{50}$ branched chain alkynylthio or $C_3$–$C_{50}$ branched chain substituted alkynylthio; and Y is a heterobifunctional or homobifunctional cross-linking reagent;

where said substituent of said substituted alkyl, substituted alkenyl and substituted alkyne moieties is an intercalator, a conjugate, polyamine, polyamide, or polyethylene glycol, provided that said linker does not include a nucleosidic base.

37. The cross-linked oligonucleotide of claim 36 wherein:

$X_1$ and $X_2$, independently, are O, S, NH, CH$_2$ or CO;

$L_1$ and $L_2$, independently, are $C_1$–$C_{20}$ straight chain alkyl, $C_1$–$C_{20}$ straight chain substituted alkyl, $C_3$–$C_{50}$ branched chain alkyl, $C_3$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne, $C_3$–$C_{50}$ branched chain alkyne, $C_3$–$C_{50}$ branched chain substituted alkyne, polyamine, polyamide, polyester, polyethylene glycol, aryl, aralkyl or heterocyclic; and Y is imine, amine, oxime, hydroxylamine, hydrazine, hydrazone, azine, hydrazide-hydrazone, amide, hydrazide, semicarbazide, semicarbazone, thiosemicarbazide, thiocarbazone, disulfide, hemiacetal, α-ketoalkylthioalkyl or α-keto-alkylaminoalkyl.

38. The cross-linked oligonucleotide of claim 37 wherein $X_1$ and $X_2$, independently, are O, S or NH.

39. The cross-linked oligonucleotide of claim 37 wherein Y is imine, amine, oxime, hydrazine, hydrazone or hydroxylamine.

40. The cross-linked oligonucleotide of claim 37 wherein Y is disulfide.

41. The cross-linked oligonucleotide of claim 39 wherein:

$X_1$ and $X_2$, independently, are O or NH;

together $L_1$—Y—$L_2$ are HN—$L_3$—NH; and $L_3$ is $C_1$–$C_{20}$ straight chain alkyl, $C_1$–$C_{20}$ straight chain substituted alkyl, $C_3$–$C_{50}$ branched chain alkyl, $C_3$–$C_{50}$ branched chain substituted alkyl, $C_2$–$C_{20}$ straight chain alkenyl, $C_2$–$C_{20}$ straight chain substituted alkenyl, $C_3$–$C_{50}$ branched chain alkenyl, $C_3$–$C_{50}$ branched chain substituted alkenyl, $C_2$–$C_{20}$ straight chain alkyne, $C_2$–$C_{20}$ straight chain substituted alkyne, $C_3$–$C_{50}$ branched chain alkyne, $C_3$–$C_{50}$ branched chain substituted alkyne, polyamine, polyamide, polyester, polyethylene glycol, aryl, aralkyl or heterocyclic.

42. The cross-linked oligonucleotide of claim 41 wherein $X_1$ and $X_2$ are O.

43. The cross-linked oligonucleotide of claim 41 wherein $L_3$ is polymethylene.

44. The cross-linked oligonucleotide of claim 36 wherein said first sequence region and said second sequence region are on a single oligonucleotide strand.

45. The cross-linked oligonucleotide of claim 36 wherein said first sequence region and said second sequence region are on different oligonucleotide strands.

46. The cross-linked oligonucleotide of claim 36 wherein:

$X_1$ and $X_2$, independently, are O, S, NH, CH$_2$ or CO;

$L_1$ and $L_2$, independently, are $C_1$–$C_{20}$ straight chain alkylamino, $C_1$–$C_{20}$ straight chain substituted alkylamino, $C_3$–$C_{50}$ branched chain alkylamino, $C_3$–$C_{50}$ branched chain substituted alkylamino, $C_2$–$C_{20}$ straight chain alkenylamino, $C_2$–$C_{20}$ straight chain substituted alkenylamino, $C_3$–$C_{50}$ branched chain alkenylamino, $C_3$–$C_{50}$ branched chain substituted alkenylamino, $C_2$–$C_{20}$ straight chain alkynylamino, $C_2$–$C_{20}$ straight chain substituted alkynylamino, $C_3$–$C_{50}$ branched chain alkynylamino, $C_3$–$C_{50}$ branched chain substituted alkynylamino, $C_1$–$C_{20}$ straight chain alkylthio, $C_1$–$C_{20}$ straight chain substituted alkylthio, $C_2$–$C_{50}$ branched chain alkylthio, $C_2$–$C_{50}$ branched chain substituted alkylthio, $C_2$–$C_{20}$ straight chain alkenylthio, $C_2$–$C_{20}$ straight chain substituted alkenylthio, $C_3$–$C_{50}$ branched chain alkenylthio, $C_3$–$C_{50}$ branched chain substituted alkenylthio, $C_2$–$C_{20}$ straight chain alkynylthio, $C_2$–$C_{20}$ straight chain substituted alkynylthio, $C_3$–$C_{50}$ branched chain alkynylthio or $C_3$–$C_{50}$ branched chain substituted alkynylthio; and Y is a heterobifunctional or homobifunctional cross-linking reagent.

47. The cross-linked oligonucleotide of claim 46 wherein Y is a heterobifunctional cross-linking reagent comprising two reactive moieties independently selected from maleimide, N-hydroxysuccinimide, N-hydroxysulfosuccinimide, imidoester, pyridyl disulfide, β-carbonyl alkylhalide or photoreactive aryl azide.

48. A cross-linked oligonucleotide comprising:

a first sequence region in an oligonucleotide;

a second sequence region in an oligonucleotide;

a first space-spanning group connected to the 2'-position of a nucleotide located in said first sequence region;

a second space-spanning group connected to the 2'-position of a nucleotide located on said second sequence region; and a linking moiety covalently bonding said first and second space-spanning groups.

49. The cross-linked oligonucleotide of claim 48 wherein: said linking moiety is —N=CH—, —N(R)—CH$_2$—N(R)—, —N(R)—, —O—N=CH—, —O—N(R)—, —N(R)—N(R)—, —HC=N—N(R)—, —HC=N—N=CH—, —C(O)—N(R)—N=CH—, —C(O)N(R)—, —C(O)—N(R)—N(R)—, —N(R)—C(O)—N(R)—N(R)—, —N(R)—C(O)—N(R)—N=CH—, —N(R)—C(S)—N(R)—N(R)—, —N(R)—C(S)—N(R)—N=CH—, —S—S—, —CH(OH)—O—CH$_2$—, —CH(OH)—S—CH$_2$—, —CH$_2$—S—CH$_2$—C(O)—CH$_2$— or —CH$_2$—NH—CH$_2$—C(O)—CH$_2$—; and R is H, alkyl, alkenyl, aralkyl, an intercalator, a conjugate, polyamine, polyamide, polyethylene glycol, a group that enhances the pharmacodynamic properties of oligonucleotides or a group that enhances the pharmacokinetic properties of oligonucleotides.

50. The cross-linked oligonucleotide of claim 49 wherein R is H.

51. A method of fixing an oligonucleotide comprising:

selecting a first site in said oligonucleotide, said first site having a first nucleotide sequence;

attaching a first bond precursor to the sugar moiety of a first nucleotide of said first site;

selecting a second site in said oligonucleotide, said second site having a second nucleotide sequence;

attaching a second bond precursor to the sugar moiety of a second nucleotide of said second site; and forming a covalent cross-linkage between said first and said second bond precursors, provided that at least one of the first and second bond means is located at a non-terminal nucleotide and further provided that that said cross-linkage:

is not between the 3' carbon of a sugar moiety of said first nucleotide and the 5' carbon of a sugar moiety of said second nucleotide;

is not between the 3' carbon of a sugar moiety of said second nucleotide and the 5' carbon of a sugar moiety of said first nucleotide; and does not include a nucleosidic base.

52. The method of claim 51 including:

selecting a nucleotide having an abasic site as said first bond precursor; and attaching said second bond precursor to the 2'-position of said second nucleotide.

53. The method of claim 51 including:

attaching said first bond precursor to the 2'-position of said first nucleotide; and attaching said second bond precursor to the 2'-position of said second nucleotide.

54. The method of claim 53 including selecting said cross-linkage from:

—N=CH—, —N(R)—, —N(R)—CH$_2$—NH—, —NH—CH$_2$—NH—, —O—N=CH—, —O—N(R)—, —N(R)—N(R)—, —C=N—N(R)—, —HC=N—N=CH—, —C(O)—N(R)—N=CH—, —C(O)N(R)—, —C(O)—N(R)—N(R)—, —N(R)—C(O)—N(R)—N(R)—, —N(R)—C(O)—N(R)—N=CH—, —N(R)—C(S)—N(R)—NH—, —N(R)—C(S)—N(R)—N=CH—, —S—S—, —CH(OH)—O—CH$_2$—, —CH(OH)—S—CH$_2$—, —CH$_2$—S—CH$_2$—C(O)—CH$_2$— or —CH$_2$—NH—CH$_2$—C(O)—CH$_2$—;

wherein R is H, alkyl, alkenyl, aralkyl, an intercalator, a conjugate, polyamine, polyamide, or polyethylene glycol.

55. The method of claim 53 including selecting said cross-linkage from imine, amine, aminoalkylamine, oxime, hydroxylamine, hydrazine, hydrazone, azine, hydrazide-hydrazone, amide, hydrazide, semicarbazide, semicarbazone, thiosemicarbazide, thiocarbazone, disulfide, hemiacetal, thiohemiacetal, α-keto-alkylthioalkyl or α-keto-alkylaminoalkyl linkages.

56. The method of claim 57 including selecting said sequence of nucleotides of said first site to be complementary to and specifically hybridizable with said sequence of nucleotides of said second site.

57. The method of claim 51 wherein:

said first nucleotide is covalently bound to at least a third nucleotide and a fourth nucleotide on said oligonucleotide; and said second nucleotide is covalently bound to at least a fifth nucleotide and a sixth nucleotide on said oligonucleotide, said fifth and sixth nucleotides being different from said first nucleotide.

58. A method for cross-linking a single oligonucleotide comprising:

selecting a first nucleotide sequence in an oligonucleotide;

selecting a second nucleotide sequence in said oligonucleotide;

incorporating a nucleotide that includes an abasic site within said first nucleotide sequence;

attaching a bond precursor on a nucleotide of said second sequence; and forming a covalent cross-linkage between said abasic site and said bond precursor, provided that said cross-linkage does not include a nucleosidic base.

59. The method of claim 58 including attaching said bond precursor on the sugar moiety of said second sequence nucleotide.

60. The method of claim 58 including attaching said bond precursor on the 2'-position of said second nucleotide.

61. The method of claim 58 including:

forming an aldehydic functional group at said abasic site; and selecting said bond precursor to include a functional group capable of forming one of an oxime, imine, hydrazone, hydrazide-hydrazone, semicarbazone, thiosemicarbazone, hemiacetal or thio-hemiacetal covalent linkage with said abasic site aldehydic functional group.

62. The method of claim 58 including selecting said first nucleotide sequence to be complementary to and specifically hybridizable with said second nucleotide sequence.

63. A method of cross-linking a single oligonucleotide strand comprising:

selecting a first nucleotide sequence in an oligonucleotide;

selecting a second nucleotide sequence in said oligonucleotide;

attaching a first bond precursor to the sugar moiety of a first nucleotide of said first nucleotide sequence;

attaching a second bond precursor to the sugar moiety of a second nucleotide of said second nucleotide sequence; and forming a covalent cross-linkage between said first and said second bond precursors, provided that at least one of the first and second bond means is located at a non-terminal nucleotide and further provided that said cross-linkage:

is not between the 3' carbon of a sugar moiety of said first nucleotide and the 5' carbon of a sugar moiety of said second nucleotide;

is not between the 3' carbon of a sugar moiety of said second nucleotide and the 5' carbon of a sugar moiety of said first nucleotide; and does not include a nucleosidic base.

64. The method of claim 63 including selecting said first nucleotide sequence to be complementary to and specifically hybridizable with said second nucleotide sequence.

65. The method of claim 63 including selecting said covalent cross-linkage from imine, amine, aminoalkylamine, oxime, hydroxylamine, hydrazine, hydrazone, azine, hydrazide-hydrazone, amide, hydrazide, semicarbazide, semicarbazone, thiosemicarbazide, thiocarbazone, disulfide, hemiacetal or thiohemiacetal linkages.

66. The method of claim 63 wherein:

said first nucleotide is covalently bound to a third nucleotide and a fourth nucleotide on said oligonucleotide; and said second nucleotide is covalently bound to at least a fifth nucleotide and a sixth nucleotide on said oligonucleotide, said fifth and sixth nucleotides being different from said first nucleotide.

67. A method of cross-linking first and second strands of oligonucleotides comprising:

selecting a first nucleotide sequence in a first oligonucleotide strand;

selecting a second nucleotide sequence in a second oligonucleotide strand;

incorporating a nucleotide that includes an abasic site within said first nucleotide sequence;

attaching a bond precursor to a nucleotide of said second nucleotide sequence; and forming a covalent cross-linkage between said abasic site and said bond precursor.

68. The method of claim 67 including selecting said first nucleotide sequence to be complementary to and specifically hybridizable with said second nucleotide sequence.

69. The method of claim 67 including attaching said sequence bond precursor to the sugar moiety of said second sequence nucleotide.

70. The method of claim 69 including attaching said bond precursor to the 2'-position of said second nucleotide.

71. The method of claim 67 including:

forming an aldehydic functional group at said abasic site; and selecting said bond precursor to include a functional group capable of forming one of an oxime, imine, hydrazone, semicarbazone, thiosemicarbazone, hydrazide-hydrazone, hemiacetal or thiohemiacetal linkage with said abasic site aldehydic functional group.

72. The method of claim 67 wherein:

said first nucleotide is covalently bound to at least two nucleotides on said first oligonucleotide strand; and said second nucleotide is covalently bound to at least two nucleotides on said second oligonucleotide strand.

73. A method of cross-linking first and second strands of oligonucleotides comprising:

selecting a first nucleotide sequence in a first oligonucleotide strand;

selecting a second nucleotide sequence in a second oligonucleotide strand;

attaching a first bond precursor to the sugar moiety of a selected nucleotide of said first nucleotide sequence;

attaching a second bond precursor to the sugar moiety of a nucleotide of said second nucleotide sequence; and forming a covalent cross-linkage between said first and said second bond precursors, provided that at least one of the first and second bond means is located at a non-terminal nucleotide and further provided that said cross-linkage:

is not between the 3' carbon of a sugar moiety of said first nucleotide and the 5' carbon of a sugar moiety of said second nucleotide;

is not between the 3' carbon of a sugar moiety of said second nucleotide and the 5' carbon of a sugar moiety of said first nucleotide; and does not include a nucleosidic base.

74. The method of claim 73 including selecting said first nucleotide sequence to be complementary to and specifically hybridizable with said second nucleotide sequence.

75. The method of claim 73 including choosing said covalent cross-linkage from imine, amine, aminoalkylamine, oxime, hydroxylamine, hydrazine, hydrazone, azine, hydrazide-hydrazone, amide, hydrazide, semicarbazide, semicarbazone, thiosemicarbazide, thiocarbazone, disulfide, hemiacetal or thiohemiacetal linkages.

76. The cross-linked oligonucleotide of claim 28 wherein said space-spanning group includes a hydroxylamine.

77. The cross-linked oligonucleotide of claim 36 wherein Y is thiohemiacetal.

\* \* \* \* \*

UNITED STATES PATENT AND TRADEMARK OFFICE
CERTIFICATE OF CORRECTION

PATENT NO.   : 5,543,507
DATED         : August 6, 1996
INVENTOR(S)  : Phillip D. Cook et al.

It is certified that error appears in the above-identified patent and that said Letters Patent is hereby corrected as shown below:

Column 1,
Line 8, after "Mar. 5, 1993" insert -- now U.S. Ser. No. 08/295,743, filed August 30, 1994 -- from the next line.

Column 2,
Line 5, change "adeninc" to -- adenine --.
Line 16, change "adenic" to -- adenine --

Column 3,
Line 32, change "be" to -- been --.

Column 5,
Line 50, in the equation after "NH-" the next part should be -- $L_3$ --.
Line 51, in the equation "LB" should be -- $L_3$ --.

Column 6,
Line 35, "$CH_2$ -N (R)" should be -- $CH_2$-N (R) --.
Line 40, " (N (R) =CH" should be -- N (R) -CH --.

Column 7,
Line 9, "hydrozone" should be -- hydrazone --.

Column 9,
Line 4, change "U.S. Pat. No. 5,223,618" to -- U.S Pat. No. 5,233,618 --.

Column 11,
Line 19, "hydroxyls" should be -- 2'hydroxyls --.

Column 42,
Line 24, "oligOnucleotides" should be -- oligonucleotides --.

Column 45,
Line 49, "[2amylenyl]" should be -- 2-amylenyl --.

Column 47,
Line 15, change "I←→" should be -- I --.

Column 50,
Line 18, change "2' -O-hexyl-O-N-" to -- 2' -O-hexyl-$\Omega$-N --.

UNITED STATES PATENT AND TRADEMARK OFFICE
CERTIFICATE OF CORRECTION

PATENT NO. : 5,543,507
DATED : August 6, 1996
INVENTOR(S) : Phillip D. Cook et al.

It is certified that error appears in the above-identified patent and that said Letters Patent is hereby corrected as shown below:

Column 54,
Line 50, change "aidehyde" to -- aldehyde --.

Column 56,
Line 36, change "desaired" to -- desalted --.

Column 57,
Line 3, change "acheive" to -- achieve --.
Line 64, "desaired" should be -- desalted --.

Column 58,
Line 36, after "this" insert -- S-trityl --

Signed and Sealed this

Twenty-third Day of April, 2002

*Attest:*

JAMES E. ROGAN
*Attesting Officer*   *Director of the United States Patent and Trademark Office*